(12) United States Patent
Fukumoto et al.

(10) Patent No.: US 9,378,457 B2
(45) Date of Patent: Jun. 28, 2016

(54) INFORMATION PROCESSING APPARATUS, INFORMATION PROCESSING METHOD, AND PROGRAM FOR DETERMINING A VEHICLE BOARDING STATE

(71) Applicant: SONY CORPORATION, Tokyo (JP)

(72) Inventors: Yasutaka Fukumoto, Tokyo (JP);
Makoto Murata, Tokyo (JP);
Masatomo Kurata, Tokyo (JP);
Masanori Katsu, Tokyo (JP)

(73) Assignee: Sony Corporation, Tokyo (JP)

( * ) Notice: Subject to any disclaimer, the term of this patent is extended or adjusted under 35 U.S.C. 154(b) by 239 days.

(21) Appl. No.: 14/045,074

(22) Filed: Oct. 3, 2013

(65) Prior Publication Data

US 2014/0032476 A1    Jan. 30, 2014

Related U.S. Application Data

(63) Continuation of application No. 12/693,888, filed on Jan. 26, 2010, now Pat. No. 8,566,272.

(30) Foreign Application Priority Data

Jan. 28, 2009   (JP) .................. 2009-017187
Oct. 2, 2009    (JP) .................. 2009-230580

(51) Int. Cl.
*G06N 5/04* (2006.01)
*G06N 5/02* (2006.01)
(Continued)

(52) U.S. Cl.
CPC ............... *G06N 5/02* (2013.01); *A61B 5/1116* (2013.01); *A61B 5/1123* (2013.01); *G06N 5/04* (2013.01); *A61B 5/1038* (2013.01); *A61B 2562/0219* (2013.01)

(58) Field of Classification Search
CPC ...................................................... G06K 9/62
See application file for complete search history.

(56) References Cited

U.S. PATENT DOCUMENTS 6,522,266 B1   2/2003  Soehren
2006/0284979 A1  12/2006  Clarkson
(Continued)

FOREIGN PATENT DOCUMENTS

CN   2006-1790235   6/2006
CN   2006-1877340   12/2006
(Continued)

OTHER PUBLICATIONS of Bieber et al ("Using Physical Activity for User Behavior Analysis" 2008).*

(Continued)

*Primary Examiner* — Lut Wong
(74) *Attorney, Agent, or Firm* — Paratus Law Group, PLLC

(57) ABSTRACT

There is provided an information processing apparatus including: a sensor data generator sensing a user behavior and generating sensor data corresponding to the user behavior; a behavior recognizing unit performing a predetermined threshold value process on the sensor data to recognize the behavior exhibited by the user and generating behavior information that is information indicating the behavior exhibited by the user; a behavior manager managing the behavior information generated by the behavior recognizing unit in correspondence with the time point at which the behavior corresponding to the behavior information is exhibited; and a behavior information post-processing unit performing a predetermined post-process on the behavior information managed by the behavior manager, wherein the behavior recognizing unit further includes a plurality of behavior determination units specified to specific behaviors exhibited by the user and generates the behavior information based on the determination results of the plurality of behavior determination units.

11 Claims, 27 Drawing Sheets

(51) Int. Cl.
*A61B 5/11* (2006.01)
*A61B 5/103* (2006.01)

(56) References Cited

U.S. PATENT DOCUMENTS

| | | | |
|---|---|---|---|
| 2007/0112922 A1 | 5/2007 | Kurata et al. | |
| 2009/0184849 A1 | 7/2009 | Nasiri et al. | |
| 2010/0217533 A1* | 8/2010 | Nadkarni et al. | 702/19 |

FOREIGN PATENT DOCUMENTS

| | | |
|---|---|---|
| CN | 2007-1941752 | 4/2007 |
| JP | 10-040068 | 2/1998 |
| JP | 10-113343 | 5/1998 |
| JP | 11-042220 | 2/1999 |
| JP | 2001-198110 | 7/2001 |
| JP | 2005-292730 | 10/2005 |
| JP | 2006-175206 | 7/2006 |
| JP | 2006-340903 | 12/2006 |
| JP | 2006-345269 | 12/2006 |

OTHER PUBLICATIONS

Juha et al ("Activity Classification Using Realistic Data From Wearable Sensors" 2006).*

Kawahara et al ("Recognizing User Context Using Mobile Handsets with Acceleration Sensors" Jun. 2007).*

Jul. 15, 2014, Japanese Office Action for related JP application No. 2013-216971.

Jul. 23, 2013, JP communication issued for related JP application No. 2009-230580.

Mar. 26, 2013, JP communication issued for related JP application No. 2009-230580.

Bao, Ling, et al.; "Activity Recognition from User-Annotated Acceleration Data"; 2004; Springer-Verlag; Pervasive 2004, LNCS 3001; pp. 1-17.

Yi, Ji Soo, et al.; "Context Awareness via a Single Device-Attached Accelerometer During Mobile Computing"; 2005; ACM; MobileHCI'05; pp. 303-306.

Ravi, Nishkam, et al.; "Activity Recognition from Accelerometer Data"; 2005; AAAI Press; Proceedings of the 17th conference on Innovative applications of artificial intelligence—vol. 3; pp. 1541-1546.

Eagle, Nathan, et al.; "Reality mining: sensing complex social systems"; 2006; Springer-Verlag; Pers Ubiquit Comput; pp. 255-268.

Jan. 6, 2015, JP communication issued for related JP application No. 2013-216971.

May 25, 2015, Japanese Office Action for related JP application No. 2013-216971.

* cited by examiner

FIG. 19
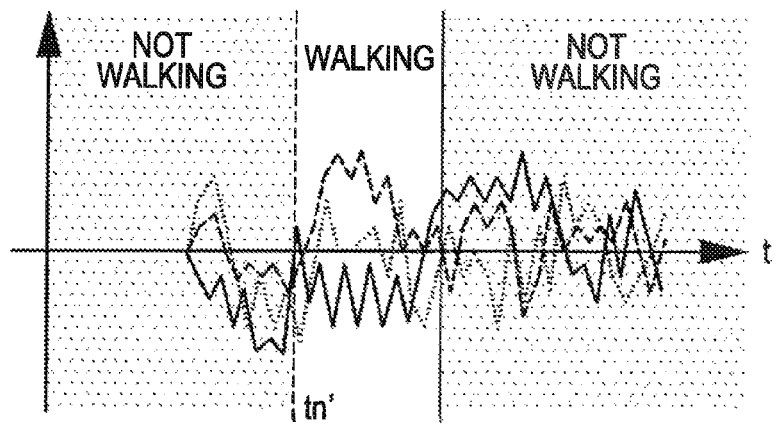
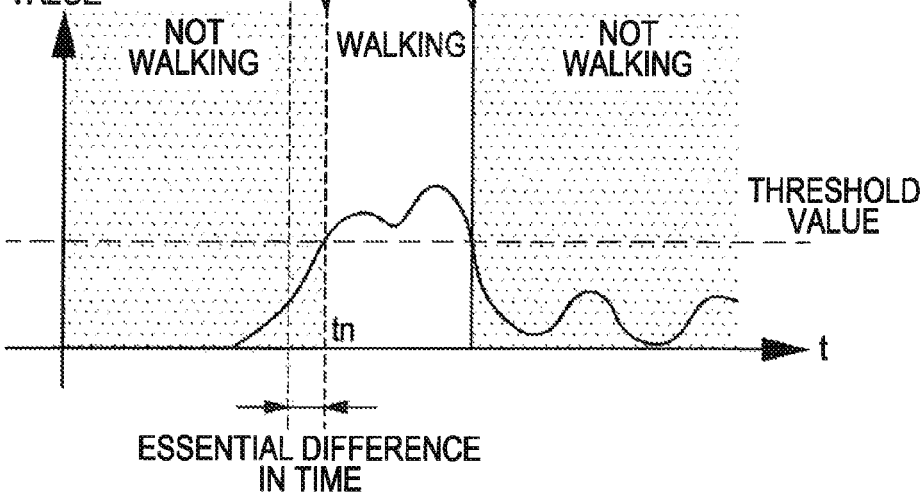

INFORMATION PROCESSING APPARATUS, INFORMATION PROCESSING METHOD, AND PROGRAM FOR DETERMINING A VEHICLE BOARDING STATE

CROSS REFERENCE TO PRIOR APPLICATION

The present application is a continuation of U.S. patent application Ser. No. 12/693,888 (filed on Jan. 26, 2010), which claims priority to Japanese Patent Application Nos. 2009-017187 (filed on Jan. 28, 2009) and 2009-230580 (filed on Oct. 2, 2009), which are all hereby incorporated by reference in their entirety.

BACKGROUND OF THE INVENTION

1. Field of the Invention

The present invention relates to an information processing apparatus, an information processing method, and a program therefor.

2. Description of the Related Art

Recently, information processing apparatuses such as mobile phones have multiple functions. Therefore, a user may obtain various types of information by using various functions provided to the information processing apparatus. As an example of a function provided to the information processing apparatus, there is a function of recognizing user behavior. For example, Japanese Unexamined Patent Application Publication No. 2006-340903 discloses a technology of recognizing user behavior such as walking, running, or stopping by using an acceleration sensor or a gyro sensor and displaying the behavior as an object.

However, in the aforementioned technology, a method of recognizing each behavior of the user with a good accuracy is not implemented. Therefore, for example, it is necessary to implement a filtering function and a calculation function for recognizing each behavior. In addition, it is also necessary to implement a method of optimizing results of behavior recognition.

SUMMARY OF THE INVENTION

It is desirable to provide a new, improved information processing apparatus, information processing method, and program capable of recognizing a user behavior with better accuracy.

According to an embodiment of the present invention, there is provided an information processing apparatus including: a sensor data generator that senses a user behavior and generates sensor data corresponding to the user behavior; a behavior recognizing unit that recognizes the behavior exhibited by the user by performing a predetermined threshold value process on the sensor data and generates behavior information that is information indicating the behavior exhibited by the user; a behavior manager that manages the behavior information generated by the behavior recognizing unit in correspondence with the time point at which the behavior corresponding to the behavior information is exhibited; and a behavior information post-processing unit that performs a predetermined post-process on the behavior information managed by the behavior manager, in which the behavior recognizing unit further includes a plurality of behavior determination units specified to specific behaviors exhibited by the user and generates the behavior information based on the determination results of the plurality of behavior determination units.

In the information processing apparatus, the behavior recognizing unit may at least include: a stopped state determination unit that determines whether or not the user is in the stopped state; a walking/running state determination unit that determines whether or not the user is in the walking state or in the running state; a jumping state determination unit that determines whether or not the user is in the jumping state; a posture change determination unit that determines whether or not the user is in the sitting state or in the standing state; an elevator boarding determination unit that determines whether or not the user is in the boarding-elevator state; an electric train boarding determination unit that determines whether or not the user is in the boarding-electric train state; and a turning-to-the-right/turning-to-the-left determination unit that determines whether or not the user turns to the right or to the left.

The behavior recognizing unit may include, as the behavior determination unit, a vehicle boarding determination unit that that determines by using the sensor data and a predetermined identification function set in advance whether or not the user boards a vehicle.

In the information processing apparatus, the behavior recognizing unit may further include a sensor data processing unit having: a sensor data storage unit that stores the sensor data in an FIFO manner; and a sensor data calculation unit that performs a predetermined calculation by using the sensor data, and in which each of the behavior determination units determines the behavior exhibited by the user based on the calculation result output from the sensor data processing unit.

In the information processing apparatus, the behavior information post-processing unit may further include an exclusive behavior information re-processing unit that detects whether or not an exclusive characteristic representing that the user exhibits exclusive behaviors that are difficult to simultaneously perform exists in the behavior information, and in which, in the case where two or more behaviors have the exclusive characteristic, the exclusive behavior information re-processing unit excludes behavior information corresponding to at least one behavior among the two or more behaviors.

In the information processing apparatus, the behavior information post-processing unit may include a false recognition behavior information re-processing unit that reprocesses the behavior information for each unit time based on a behavior information necessary condition necessary for the user to exhibit each behavior, and in which, in the case where the behavior information does not satisfy the behavior information necessary condition, the false recognition behavior information re-processing unit corrects the behavior information corresponding to the behavior.

In the information processing apparatus, the behavior information post-processing unit may include a behavior information real-time adjusting unit that determines that the user exhibits each behavior at the time point that is earlier than the time point at which the behavior recognizing unit transmits the behavior information to the behavior manager by the time necessary for the behavior recognizing unit to generate the behavior information corresponding to each behavior.

In the case where two or more behaviors performed within a predetermined time are similar to each other, the behavior information post-processing unit may compare summed times of the behavior information corresponding to the two or more behaviors and select the behavior information having the longest summed time as the behavior information for the predetermined time.

In the information processing apparatus, the sensor data may include first to third acceleration sensor data that are data regarding accelerations in predetermined coordinate axes, in which the sensor data calculation unit calculates variance values of the first to third acceleration sensor data in a first predetermined time stored in the sensor data storage unit, and in which, in the case where the maximum variance value that is the largest variance value is smaller than a stop recognition value for recognizing that the user stops and a time when the maximum variance value is smaller than the stop recognition value continues to be longer than a stop recognition time when the user is recognized as stopping, the stopped state determination unit generates the behavior information indicating that the user stops, and in the case where the maximum variance value is smaller than the stop recognition value and the time when the maximum variance value is smaller than the stop recognition value does not continue to be longer than the stop recognition time, the stopped state determination unit generates the behavior information indicating that the user temporarily stops.

In the information processing apparatus, the sensor data may include first to third acceleration sensor data that are data regarding accelerations in predetermined coordinate axes, in which the sensor data calculation unit calculates variance values of the first to third acceleration sensor data in a second predetermined time stored in the sensor data storage unit and the maximum variance value that is the largest variance value, calculates an autocorrelation function of the acceleration sensor data stored in the sensor data storage unit and a maximum value of the autocorrelation function to calculate walking/running frequency data at the time when the user walks or runs, and calculates walking/running determination data for determining whether or not the user walks or runs by multiplying the walking/running frequency data with the maximum variance value, and in which, in the case where a value of the walking/running determination data is larger than a minimum walking recognition value that is a lower limit value for recognizing that the user walks and smaller than a maximum walking recognition value that is an upper limit value for recognizing that the user walks, the walking/running state determination unit generates the behavior information indicating that the user walks, and in the case where the value of the walking/running determination data is larger than the maximum walking recognition value, the walking/running state determination unit generates the behavior information indicating that the user runs.

In the information processing apparatus, the sensor data calculation unit may integrate the walking/running frequency data, and the walking/running state determination unit may generate the behavior information corresponding to the number of steps of the user from the result of the integration.

In the information processing apparatus, the sensor data may include first to third acceleration sensor data that are data regarding accelerations in predetermined coordinate axes, in which the sensor data calculation unit calculates a jumping state determination value by calculating magnitudes of jumping accelerations represented by magnitudes of the first to third acceleration sensor data, and in which, in the case where the jumping state determination value is larger than a minimum jumping recognition value that is a lower limit value for recognizing that the user jumps, the jumping state determination unit generates the behavior information indicating that the user jumps.

In the information processing apparatus, the sensor data may include first to third acceleration sensor data that are data regarding accelerations in predetermined coordinate axes, in which the sensor data calculation unit calculates first to third gravity data in the predetermined coordinate axes based on the first to third acceleration sensor data, calculates first gravity change data representing how much the first gravity data are changed from the first gravity data that are previously stored in the storage unit, second gravity change data representing how much the second gravity data are changed from the second gravity data that are previously stored in the storage unit, and third gravity change data representing how much the third gravity data are changed from the third gravity data that are previously stored in the storage unit, and calculates a posture change determination value of determining whether or not the user changes the posture, which is represented by magnitudes of the first gravity change data, the second gravity change data, and the third gravity change data, and in which, in the case where the posture change determination value is larger than a minimum posture change recognition value that is a lower limit value for recognizing that the user changes the posture and in the case where the user is already standing, the posture change determination unit generates the behavior information indicating that the user sits, and in the case where the posture change determination value is larger than the minimum posture change recognition value and in the case where the user is already sitting, the posture change determination unit generates the behavior information indicating that the user stands.

In the information processing apparatus, the sensor data may include first to third acceleration sensor data that are data regarding accelerations in predetermined coordinate axes, in which the sensor data calculation unit calculates gravity direction acceleration sensor data that is information indicating the acceleration in the gravity direction based on the first acceleration sensor data, the second acceleration sensor data, and the third acceleration sensor data and calculates elevator rising determination data of determining whether or not the user boards the elevator by calculating a difference between the gravity direction acceleration sensor data and the gravity, in which in the case where the elevator rising determination data is larger than a predetermined value $D_\alpha$ at first and, after that, smaller than a predetermined value $D_\beta$, the elevator boarding determination unit generates the behavior information indicating that the user is rising at in the elevator, and in the case where elevator rising determination data is smaller than the predetermined value $D_\beta$ at first and, after that, larger than the predetermined value $D_\alpha$, the elevator boarding determination unit generates the behavior information indicating that the user is descending at in the elevator, wherein in which the $D_\alpha$ is a minimum elevator rising recognition value that is a lower limit value for recognizing that the user starts to rise at in the elevator, and wherein in which the $D_\beta$ is a maximum elevator descending recognition value that is an upper limit value for recognizing that the user starts to descend in the elevator.

In the information processing apparatus, the sensor data calculation unit may calculate gravity adjusting data represented by the magnitudes of the first acceleration sensor data, the second acceleration sensor data, and the third acceleration sensor data to allow the value of the gravity to be corrected, record the gravity adjusting data in the sensor data storage unit, and calculate a gravity adjusting variance value that is a variance value of the gravity adjusting data stored in the sensor data storage unit and a gravity adjusting average data that is an average value of the gravity adjusting data, and in which, in the case where the gravity adjusting variance value is smaller than a maximum allowable gravity adjusting variance value that is a maximum variance value for allowing the gravity to be adjusted, in the case where the gravity adjusting average data is larger than a minimum allowable gravity average value that is a minimum average value of allowing the gravity to be adjusted, and in the case where the gravity adjusting average data is smaller than a maximum allowable gravity average value that is a maximum average value of allowing the gravity to be adjusted, the sensor data calculation unit considers the value of the gravity adjusting average data as the gravity after correction and performs calculation by using the gravity after correction instead of the gravity.

In the information processing apparatus, the sensor data may include first to third acceleration sensor data that are data regarding accelerations in predetermined coordinate axes, in which the sensor data calculation unit calculates horizontal direction acceleration sensor data and vertical direction acceleration sensor data based on the first to third acceleration sensor data, records the horizontal direction acceleration sensor data and the vertical direction acceleration sensor data in the sensor data storage unit, calculates a horizontal direction variance value based on the horizontal direction acceleration sensor data recorded in the sensor data storage unit, calculates a vertical direction variance value based on the vertical direction acceleration sensor data recorded in the sensor data storage unit, and calculates electric train boarding determination data of determining whether or not the user boards the electric train by integrating the small variance value between the horizontal direction variance value and the vertical direction variance value, and in which, in the case where the electric train boarding determination data is larger than a minimum electric train boarding recognition value that is a lower limit value for recognizing that the user boards the electric train, the electric train boarding determination unit generates the behavior information indicating that the user boards the electric train.

In the information processing apparatus, in the case where the vertical direction variance value is equal to or smaller than a minimum allowable vertical variance value that is a minimum allowable vertical direction variance value, or in the case where the vertical direction variance value is equal to or larger than a maximum allowable vertical variance value that is a maximum allowable vertical direction variance value, the sensor data calculation unit may calculate the electric train boarding determination data as zero.

In the information processing apparatus, the sensor data may include first to third acceleration sensor data that are data regarding accelerations in predetermined coordinate axes and first to third gyro sensor data that are data regarding gyros in predetermined coordinate axes, in which the sensor data calculation unit calculates an angular velocity in the gravity direction based on the first to third acceleration sensor data, from which the frequency area is removed, and the first to third gyro sensor data, and in which, in the case where the angular velocity is smaller than a maximum turning-to-the-right recognition value that is an upper limit value for recognizing that the user turns to the right, the turning-to-the-right/turning-to-the-left determination unit generates the behavior information indicating that the user turns to the right, and in the case where angular velocity is larger than a minimum turning-to-the-left recognition value that is a lower limit value for recognizing that the user turns to the left, the turning-to-the-right/turning-to-the-left determination unit generates the behavior information indicating that the user turns to the left.

In the information processing apparatus, the sensor data may include first to third acceleration sensor data that are data regarding accelerations in predetermined coordinate axes, in which the sensor data calculation unit calculates a value of the identification function by using a characteristic vector generated based on the first to third acceleration sensor data and the identification function set according to the type of vehicle, and in which, in the case where the calculated value of the identification function is larger than a vehicle boarding recognition value that is used to recognize whether or not to board the vehicle corresponding to the identification function, the vehicle boarding determination unit generates the behavior information indicating that the user boards the vehicle corresponding to the identification function.

According to another embodiment of the present invention, there is provided an information processing method including the steps of: sensing a user behavior and generating sensor data corresponding to the user behavior; recognizing the behavior exhibited by the user by performing a predetermined threshold value process on the sensor data and generating behavior information that is information indicating the behavior exhibited by the user; managing the behavior information generated by the behavior recognizing unit in correspondence with the time point at which the behavior corresponding to the behavior information is exhibited; and performing a predetermined post-process on the behavior information managed by the behavior manager, in which, the behavior recognition further includes a plurality of steps of determining behaviors specified to the behaviors exhibited by the user and generating the behavior information based on the determination results of the plurality of steps of determining the behaviors.

According to still another embodiment of the present invention, there is provided a program causing a computer including a predetermined sensor to execute: a sensor data generation function of sensing a user behavior and generates sensor data corresponding to the user behavior; a behavior recognition function of recognizing the behavior exhibited by the user by performing a predetermined threshold value process on the sensor data and generating behavior information that is information indicating the behavior exhibited by the user; a behavior managing function of managing the behavior information generated by the behavior recognizing unit in correspondence with the time point at which the behavior corresponding to the behavior information is exhibited; and a behavior information post-process function of performing a predetermined post-process on the behavior information managed by the behavior manager, in which the behavior recognition function further includes a plurality of behavior determination functions specified to specific behaviors exhibited by the user and generates the behavior information based on the determination results of the plurality of behavior determination functions.

According to a further still another embodiment of the present invention, there is provided a computer-readable recording medium, on which the program is recorded.

As described above, according to the invention, the accuracy of the user behavior recognition function may be improved by the filtering function and the calculation function for each behavior and by adjusting the recognition result of the behavior.

BRIEF DESCRIPTION OF THE DRAWINGS

FIG. 19 is a diagram illustrating a behavior information post-processing method in the information processing apparatus according to the embodiment of the invention.

DESCRIPTION OF THE PREFERRED EMBODIMENTS

Figure 1:
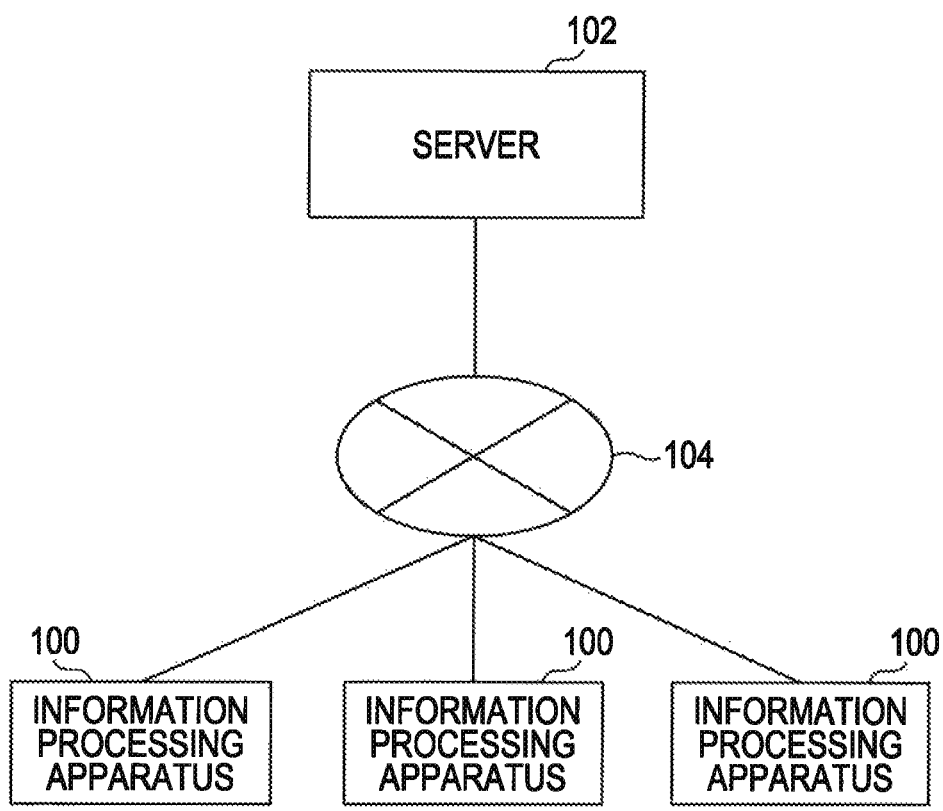
FIG. 1 is a diagram illustrating a network that is adaptable to technologies according to embodiments of the invention.

Hereinafter, exemplary embodiments of the invention will be described with reference to the accompanying drawings. In addition, in the specification and drawings, elements having the substantially same functional configurations are denoted by the same reference numerals, and description thereof is omitted.

Flow of Description

In the specification, the flow of description is as follows. First, a configuration of a network including an information processing apparatus according to embodiments of the invention will be described with reference to FIG. 1. Next, an example of a configuration of the information processing apparatus according to the embodiments will be described with reference to FIG. 2.

Figure 3:
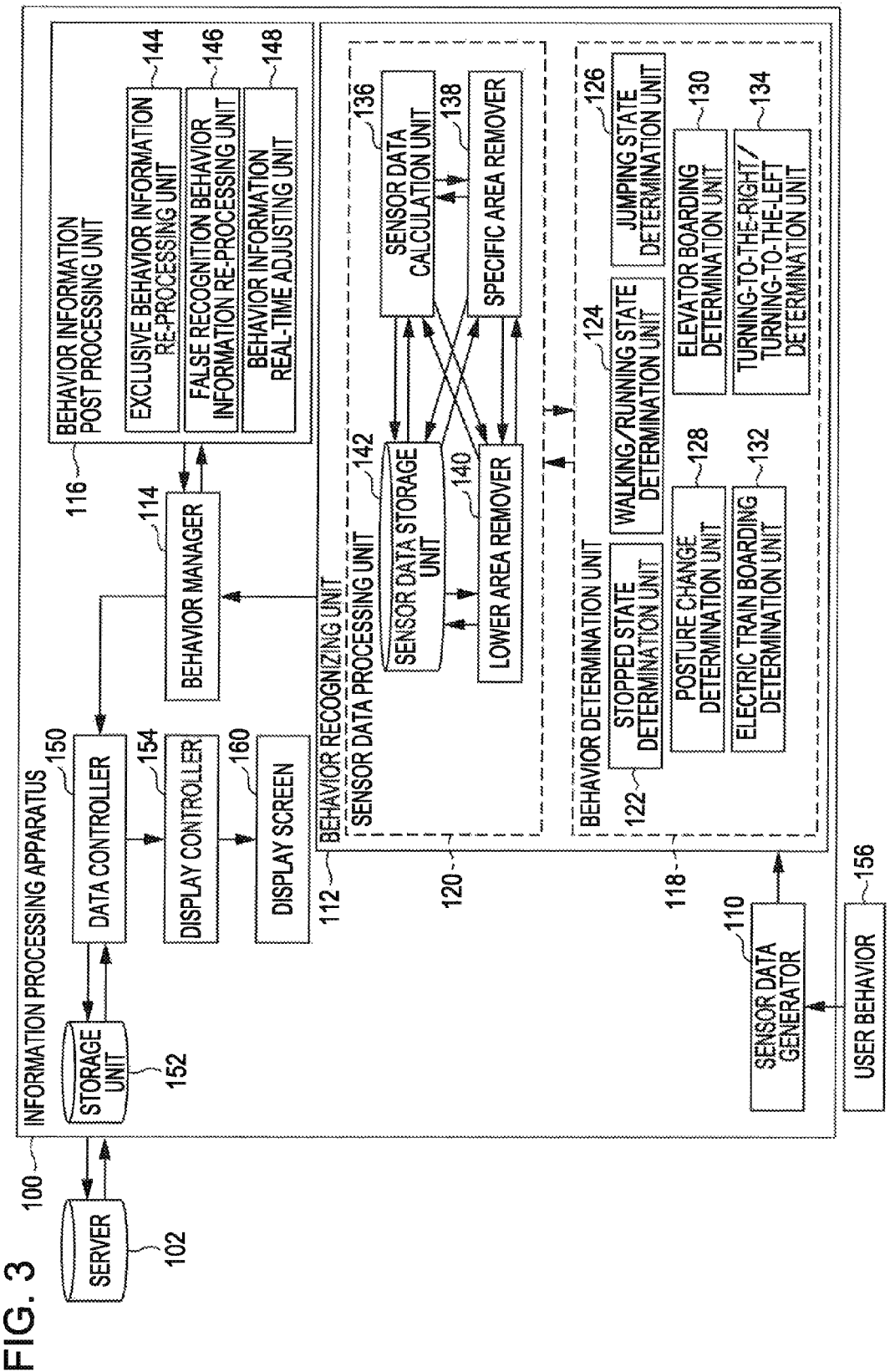
FIG. 3 is a diagram illustrating a functional configuration of the information processing apparatus according to a first embodiment of the invention.

Next, a functional configuration of an information processing apparatus according to a first embodiment of the invention will be described with reference to FIG. 3. Next, an overview and application examples of the information processing method according to the first embodiment of the invention will be described with reference to FIGS. 4 to 20. Next, modified examples of the information processing method according to the first embodiment of the invention will be described with reference to FIGS. 21 to 23.

Figure 24:
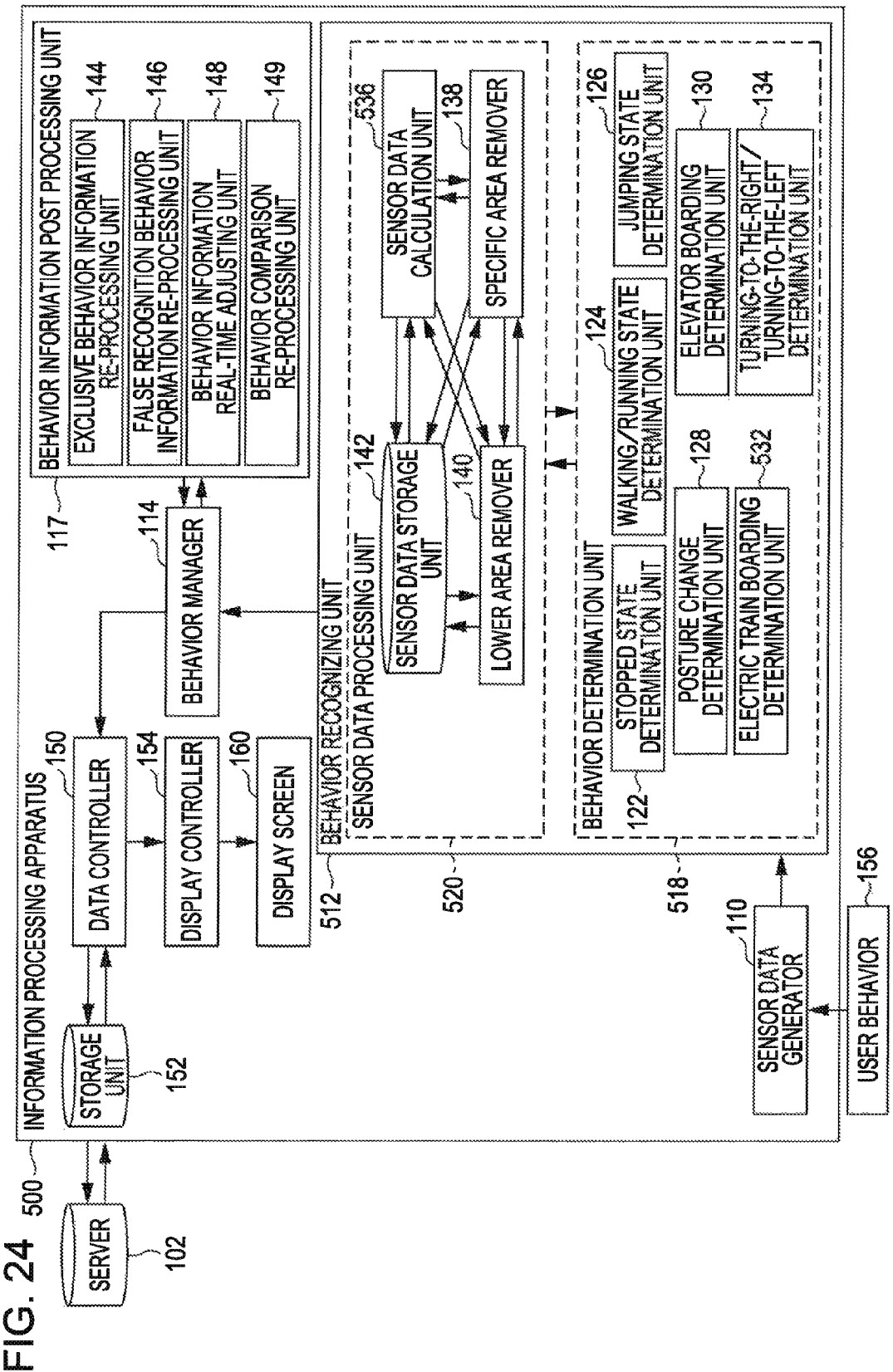
FIG. 24 is a diagram illustrating a functional configuration of an information processing apparatus according to a second embodiment of the invention.

Next, a functional configuration of an information processing method according to a second embodiment of the invention will be described with reference to FIG. 24. Next, an overview and application example of the information processing method according to the second embodiment of the invention will be described with reference to FIGS. 25 and 26.

Figure 27:
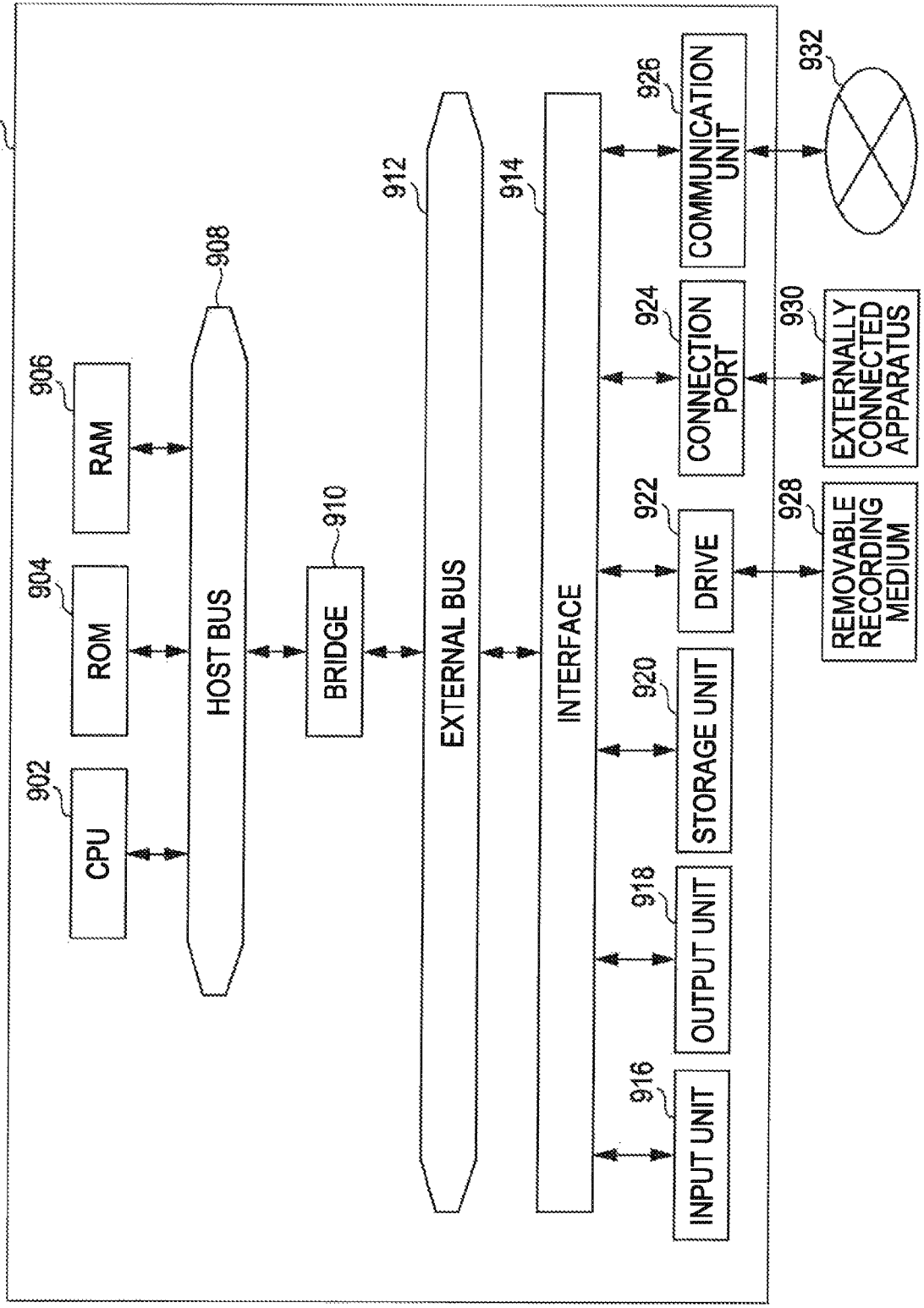
FIG. 27 is a diagram illustrating a hardware configuration of an information processing apparatus according to the embodiment of the invention.

In addition, a hardware configuration capable of implementing functions of the information processing apparatus according to the embodiments of the invention will be described with reference to FIG. 27. Finally, together with the technical concepts of the embodiments, functions and effects obtained from the technical concepts will be simply described.

1. Example of Configuration of Network

2. Example of Configuration of Information Processing Apparatus 100, 500

3. Functional Configuration of Information Processing Apparatus 100 according to First Embodiment of the Invention 4. Overview of Information Processing Method in Information Processing Apparatus 100

5. Application Examples of Information Processing Method in Information Processing Apparatus 100

6. Modified Examples of First Embodiment

7. Functional Configuration of Information Processing Apparatus 500 according to Second Embodiment of the Invention 8. Application Examples of Information Processing Method in Information Processing Apparatus 500

9. Example of Hardware Configuration of information Processing Apparatus 100, 500

10. Statistics

1. Example of Configuration of Network

First, a configuration of a network including an information processing apparatus according to embodiments of the invention will be described with reference to FIG. 1. FIG. 1 is a diagram illustrating an example of a system configuration of an information processing system 1 according to the embodiment.

As shown in FIG. 1, the information processing system 1 mainly includes an information processing apparatus 100 (information processing apparatus 500, hereinafter, this is the same in the description referring to FIGS. 1 and 2), a server 102, and a communication network 104.

The information processing apparatus 100 performs a process based on predetermined data in order to display behavior representing data received from the server 102 as an object on a display screen. In addition, the information processing apparatus 100 generates objects based on behavior information corresponding to user behavior and transmits the objects to the server 102. The information processing apparatus 100 can perform various processes as well as the above processes. Hereinafter, the information processing apparatus 100 will be described in detail again. In addition, as examples of predetermined data, there are acceleration sensor data and gyro sensor data based on behavior carried by the user. The predetermined data are described in detail as follows.

The server 102 supplies behavior information, which is transmitted from an information processing apparatus 100, to a different information processing apparatus 100. In addition, the server 102 supplies the behavior information, which is transmitted from the information processing apparatus 100, to the different information processing apparatus 100.

The communication network 104 is a communication line network that connects the information processing apparatus 100 and the server 102 so as to be bi-directionally communicatable or one-directionally communicatable. The communication network 104 includes, for example, the Internet, an NGN (Next Generation Network) net, a telephone network, a satellite communication network, a public line network such as a broadcast communication line, WAN (Wide Area Network), LAN (Local Area Network), IP-VPN (Internet Protocol-Virtual Private Network), Ethernet (registered trade mark), and a leased line network such as a wireless LAN. The communication network may be a wired or wireless network.

The server 102 supplies the behavior information acquired from the information processing apparatus 100 through the communication network 104 to the different information processing apparatus 100. The information processing apparatus 100 generates a picture signal, in which a plurality of users is displayed as objects, by processing the behavior information acquired from the server 102 and the behavior information generated by the apparatus 100.

2. Example of Configuration of Information Processing Apparatus 100, 500

Now, an example of a configuration of the information processing apparatus 100 will be described with reference to FIG. 2. FIG. 2 is a diagram illustrating an example of a configuration of the information processing apparatus 100. In FIG. 2, in order to obtain the effects of the invention, a mobile phone is exemplified as a preferred information processing apparatus 100. However, in FIG. 2, only the important keys used for input manipulations according to the embodiment are shown.

Figure 2:
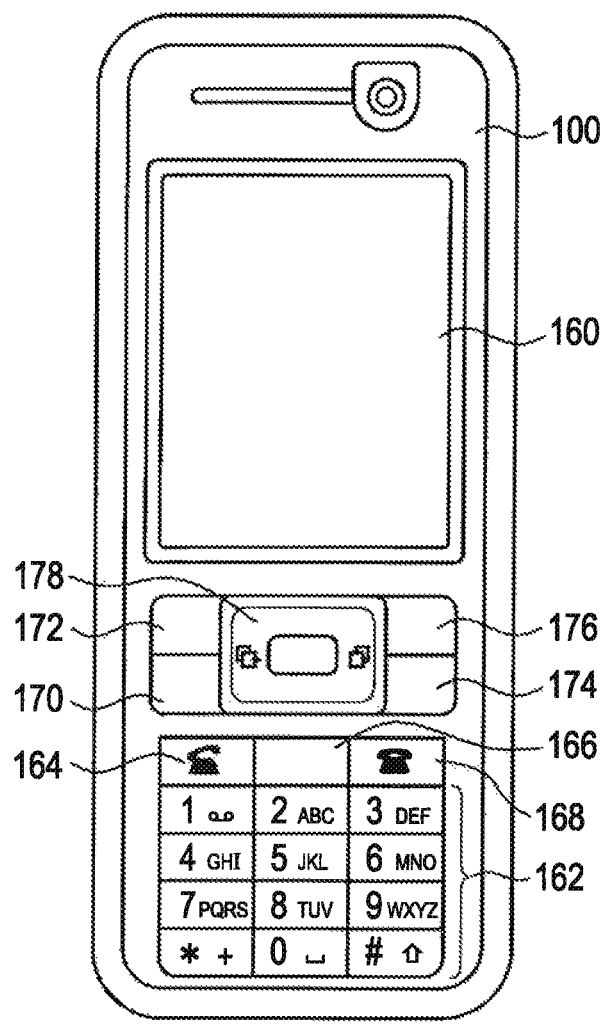
FIG. 2 is a diagram illustrating an apparatus configuration of an information processing apparatus according to the embodiments of the invention.

As shown in FIG. 2, the information processing apparatus 100 includes a display screen 160, an input key 162, a communication key 164, a clear key 166, a power key 168, a menu key 170, a mail key 172, and a memory key 174, a communication key 176, and an arrow key 178.

First, the information processing apparatus 100 is provided with the display screen 160. The display screen 160 is used to display a transmitted/received e-mail or to display various types of information. In addition, the display screen 160 may have a touch panel function.

In addition, the information processing apparatus 100 is provided with the input key 162. The input key 162 is used to input characters or the like in the case of generating the e-mail. In addition, the input key 162 is also used to input the number of the party being called in the case of making a phone call.

In addition, the information processing apparatus 100 is provided with the communication key 164. The communication key 164 is used to activate the call. In addition, the information processing apparatus 100 is provided with the clear key 166. The clear key 166 is used to clear various types of information. In addition, the information processing apparatus 100 is provided with the power key 168. The power key 168 is used to power on the information processing apparatus 100.

In addition, the information processing apparatus 100 is provided with the menu key 170. The menu key 170 is used to display various types of menu. In addition, the information processing apparatus 100 is provided with the mail key 172. The mail key 172 is used to make the display screen for generating a mail pop up. In addition, the information processing apparatus 100 is provided with the memory key 174. The memory key 174 is used to display, for example, other users' phone numbers or mail addresses that have been registered by the user.

In addition, the information processing apparatus 100 is provided with the communication key 176. The communication key 176 is used to activate, for example, the Internet connection. In addition, the information processing apparatus 100 is provided with the arrow key 178. The arrow key 178 is used to select, for example, various types of information output on the display screen with a cursor.

In addition, the mobile phone as the example of the information processing apparatus 100 is not limited to a specific one as long as it has the above-described form and functions.

3. Functional Configuration of Information Processing Apparatus 100 According to First Embodiment of the Invention Next, a functional configuration of the information processing apparatus 100 will be described with reference to FIG. 3. FIG. 3 is a diagram illustrating an example of a functional configuration of the information processing apparatus 100 according to the first embodiment of the invention. The information processing apparatus 100 has features in terms of a filtering function and calculation function for the sensor data depending on the user behavior and a post-process function for recognition results of each behavior.

The information processing apparatus 100 includes a sensor data generator 110, a behavior recognizing unit 112, a behavior manager 114, a behavior information post-processing unit 116, a data controller 150, a storage unit 152, a display controller 154, and a display screen 160. The behavior recognizing unit 112 includes a behavior determination unit 118 and a sensor data processing unit 120. The behavior determination unit 118 includes a stopped state determination unit 122, a walking/running state determination unit 124, a jumping state determination unit 126, a posture change determination unit 128, an elevator boarding determination unit 130, an electric train boarding determination unit 132, and a turning-to-the-right/turning-to-the-left determination unit 134. The sensor data processing unit 120 includes a sensor data calculation unit 136, a specific area remover 138, a lower area remover 140, and a sensor data storage unit 142. The behavior information post-processing unit 116 includes an exclusive behavior information re-processing unit 144, a false recognition behavior information re-processing unit 146, and a behavior information real-time adjusting unit 148.

The sensor data generator 110 senses the user behavior 156 and generates sensor data that is information corresponding to the user behavior. In addition, the herein-mentioned user behavior 156 denotes information regarding the user's walking, running, standing, sitting, jumping, stopping, boarding an electric train, boarding an elevator, turning to the right or left, or the like. The information on the user behavior 156 is, for example, information indicating the user behavior accompanied with the information processing apparatus 100. The sensor data is based on the behavior exhibited by the user, which is included in the information processing apparatus 100.

The behavior recognizing unit 112 acquires the sensor data from the sensor data generator 110. The behavior recognizing unit 112 recognizes the behavior exhibited by the user by performing a predetermined threshold value process on the sensor data and generates the behavior information that is the information indicating the behavior exhibited by the user. The behavior recognizing unit 112 further includes a plurality of behavior determination units 118 specified to the behaviors exhibited by the user to generate the behavior information based on the determination results of the plurality of behavior determination units 118. In addition, the sensor data includes, for example, acceleration sensor data and gyro sensor data.

In addition, the acceleration sensor data includes first acceleration sensor data, second acceleration sensor data, and third acceleration sensor data. The first acceleration sensor data are data regarding the acceleration in a predetermined coordinate axis. In addition, the second acceleration sensor data are data regarding the acceleration in a coordinate axis different from the coordinate axis of the first acceleration sensor data, for example, in a coordinate axis perpendicular to the coordinate axis of the first acceleration sensor data. In addition, the third acceleration sensor data are data regarding the acceleration in a coordinate axis different from the coordinate axes of the first acceleration sensor data and the second acceleration sensor data, for example, in a coordinate axis perpendicular to the coordinate axes of the first acceleration sensor data and the second acceleration sensor data.

The plurality of behavior determination units 118 includes a stopped state determination unit 122, a walking/running state determination unit 124, a jumping state determination unit 126, a posture change determination unit 128, an elevator boarding determination unit 130, an electric train boarding determination unit 132, and a turning-to-the-right/turning-to-the-left determination unit 134.

The stopped state determination unit 122 determines whether or not the user is in the stopped state. The walking/running state determination unit 124 determines whether the user is in the walking state or in the running state. The jumping state determination unit 126 determines whether or not the user is in the jumping state or in the non-jumping state. The posture change determination unit 128 determines whether the user is in the sitting state or in the standing state. The elevator boarding determination unit 130 determines whether or not the user is in the boarding-elevator state. The electric train boarding determination unit 132 determines whether or not the user is in the boarding-electric train state. The turning-to-the-right/turning-to-the-left determination unit 134 determines whether the user turns to the right or the left. In this manner, in the information processing apparatus 100 according to the embodiment, the behavior recognition functions specified to the behaviors are included, so that the behaviors may be recognized with a good accuracy. The behavior recognition functions for the behaviors will be described later.

The sensor data processing unit 120 receives a signal for performing the process based on the behaviors from the plurality of behavior determination units 118. The sensor data processing unit 120 performs the process on the sensor data based on the signal to generate the behavior information that is the information indicating the user behavior. More specifically, the sensor data calculation unit 136, the specific area remover 138, the lower area remover 140, and the sensor data storage unit 142 performs the above-described process by predetermined processing methods specified to the behaviors. The sensor data calculation unit 136 performs a predetermined calculation by using the sensor data. The specific area remover 138 removes a range excluding a specific area from the input data. The lower area remover 140 removes a range smaller than a predetermined threshold value from the input data. The sensor data storage unit 142 records the sensor data in the FIFO (First In First Out) manner. A predetermined processing method specified to each behavior will be described later in detail with reference to FIGS. 11 to 17.

The behavior manager 114 manages the behavior information generated by the behavior recognizing unit 112 in correspondence with the time point at which the behavior corresponding to behavior information is exhibited. More specifically, the behavior manager 114 transfers the managed behavior information to the behavior information post-processing unit 116. Next, the behavior information post-processing unit 116 performs a predetermined post-process on the behavior information, and after that, the behavior manager 114 acquires and manages the behavior information.

As described above, the behavior information post-processing unit 116 performs the predetermined post-process on the behavior information input by the behavior manager 114. The predetermined post-process is performed by the exclusive behavior information re-processing unit 144, the false recognition behavior information re-processing unit 146, and the behavior information real-time adjusting unit 148. On the basis of the exclusive characteristic in that the user is not allowed to exhibit two or more behaviors simultaneously, the exclusive behavior information re-processing unit 144 reprocesses the behavior information corresponding to each behavior for each unit time. More specifically, in the case where two or more behaviors have the exclusive characteristic, the exclusive behavior information re-processing unit 144 excludes the behavior information corresponding to at least one behavior among the two or more behaviors. In addition, the false recognition behavior information re-processing unit 146 reprocesses the behavior information for each unit time based on the behavior information necessary condition necessary for the user to exhibit each behavior. More specifically, in the case where the user behavior does not satisfy the behavior information necessary condition, the false recognition behavior information re-processing unit 146 excludes the behavior information corresponding to the behavior. In addition, the behavior information real-time adjusting unit 148 determines that the user exhibits each behavior at the time that is earlier than the time when the behavior recognizing unit 112 transmits the behavior information to the behavior manager 114 by the time necessary for the behavior recognizing unit 112 to generate the behavior information corresponding to each behavior. The predetermined post-process of the behavior information post-processing unit 116 will be described later with reference to FIGS. 18 to 21. In this manner, in the information processing apparatus 100 according to the embodiment, since the above-described post-process is performed on the behavior information, the behavior information specified to each behavior may be recognized with a good accuracy without false recognition.

The data controller 150 acquires the behavior information, which is subject to the post-process, from the behavior manager 114. The data controller 150 may generate a picture signal that is an object based on each behavior corresponding to the acquired behavior information.

In addition, the data controller 150 may acquire the behavior information generated by the information processing apparatus 100 of a different user from the server 102. The different user denotes a user different from the user having the information processing apparatus 100. Therefore, the data controller 150 may also generate a picture signal that is an object based on each behavior corresponding to the behavior information of the different user. Next, the data controller 150 transmits the picture signal to the display controller 154. The display controller 154 has a picture signal conversion control function. Therefore, after receiving the picture signal, the display controller 154 may display the picture signal on the display screen 160. As a result, for example, the information processing apparatus 100 disposes objects regarding the behavior information of different users as well as the user having the information processing apparatus 100 on the display screen 160 to display the objects as picture signals. In this manner, according to the information processing apparatus 100 according to the embodiment, the user may, for example, check other user behaviors.

The storage unit 152 may store the behavior information acquired by the data controller 150. Therefore, the data controller 150 may acquire the past behavior information from the display controller 154 to generate a picture signal that is an object based on each behavior corresponding to the past behavior information. In this manner, according to the information processing apparatus 100, the user may check the past behavior of the user and the behavior of the other users.

4. Overview of Information Processing Method in Information Processing Apparatus 100

Figure 4:
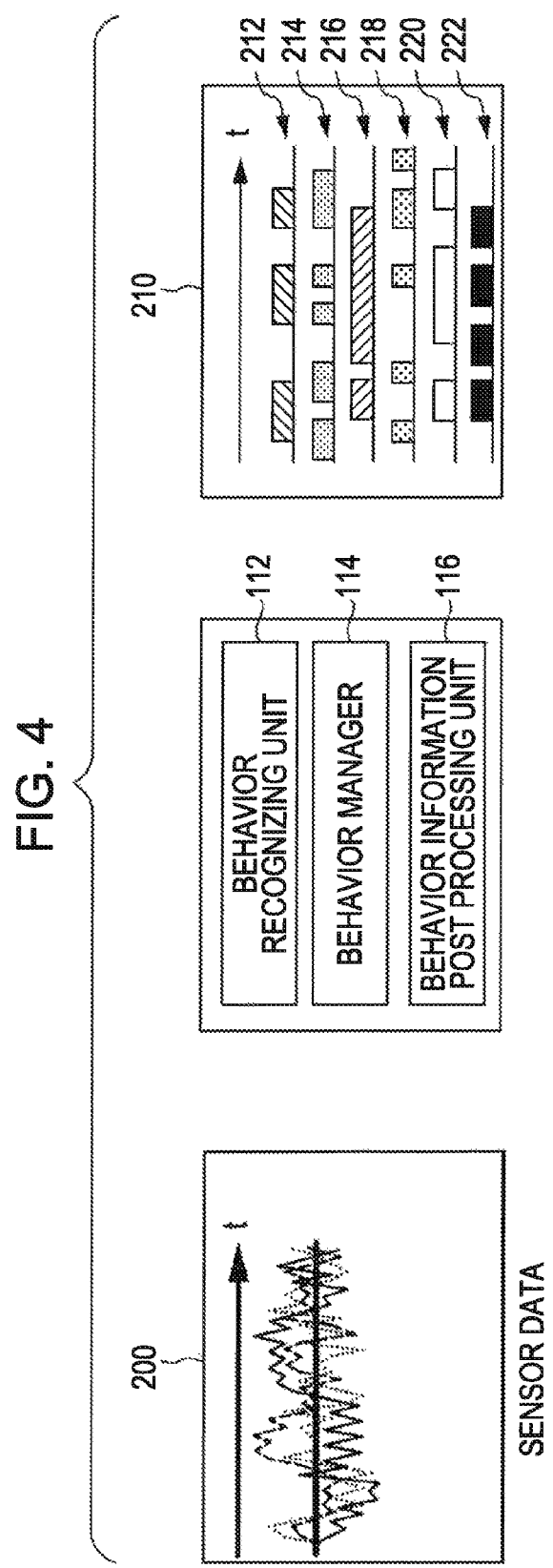
FIG. 4 is a diagram illustrating an overview of an information processing method of the information processing apparatus according to the embodiment of the invention.

4-1. Behavior Recognition Function and Behavior Information Post-Process Function Next, the behavior recognition function and the behavior information post-process function will be described with reference to FIG. 4. FIG. 4 is a diagram illustrating the overview of the behavior recognition function and the behavior information post-process function. First, the sensor data generator 110 generates the sensor data 200 based on the user behavior. The behavior recognizing unit 112, the behavior manager 114, and the behavior information post-processing unit 116 perform predetermined processes corresponding to the behaviors with respect to the sensor data. After the process, the behavior information 210 indicating which behavior the user performs every time is generated. Each of reference numerals 212, 214, 216, 218, 220, and 222 denotes whether or not each behavior is performed each time. Details will be described later.

Figure 5:
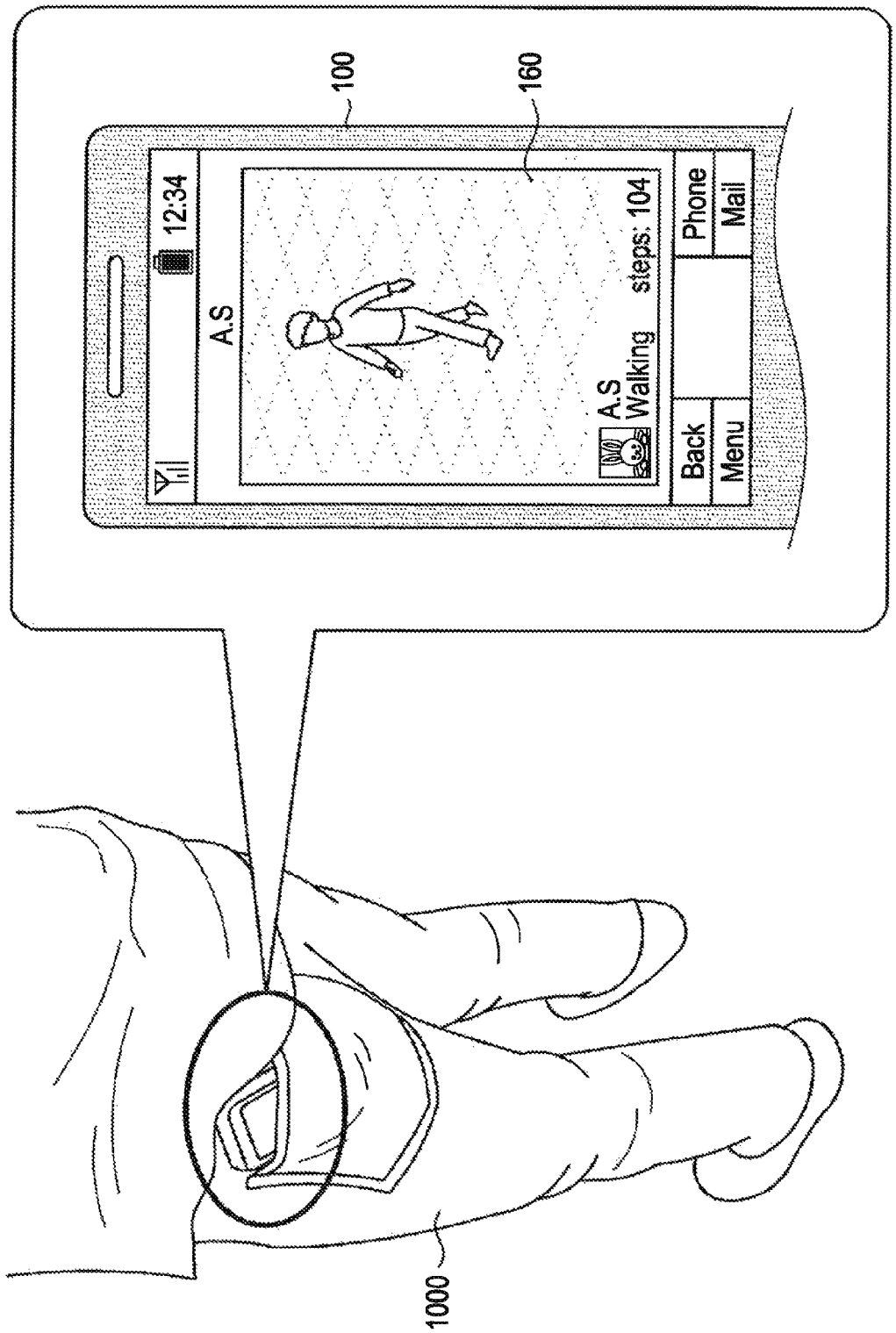
FIG. 5 is a diagram illustrating an overview of an information processing method of the information processing apparatus according to the embodiment of the invention.

FIG. 5 is a diagram illustrating an example of usage of the information processing apparatus 100 according to the embodiment. As shown in FIG. 5, for example, the information processing apparatus 100 is received in a pocket or the like of clothes that a user 1000 wears. The display screen 160 of the information processing apparatus 100 displays which behavior the user 1000 actually exhibits. The behavior state of the other persons as well as the behavior state of the user 1000 may be displayed through the server or the like.

Figure 6:
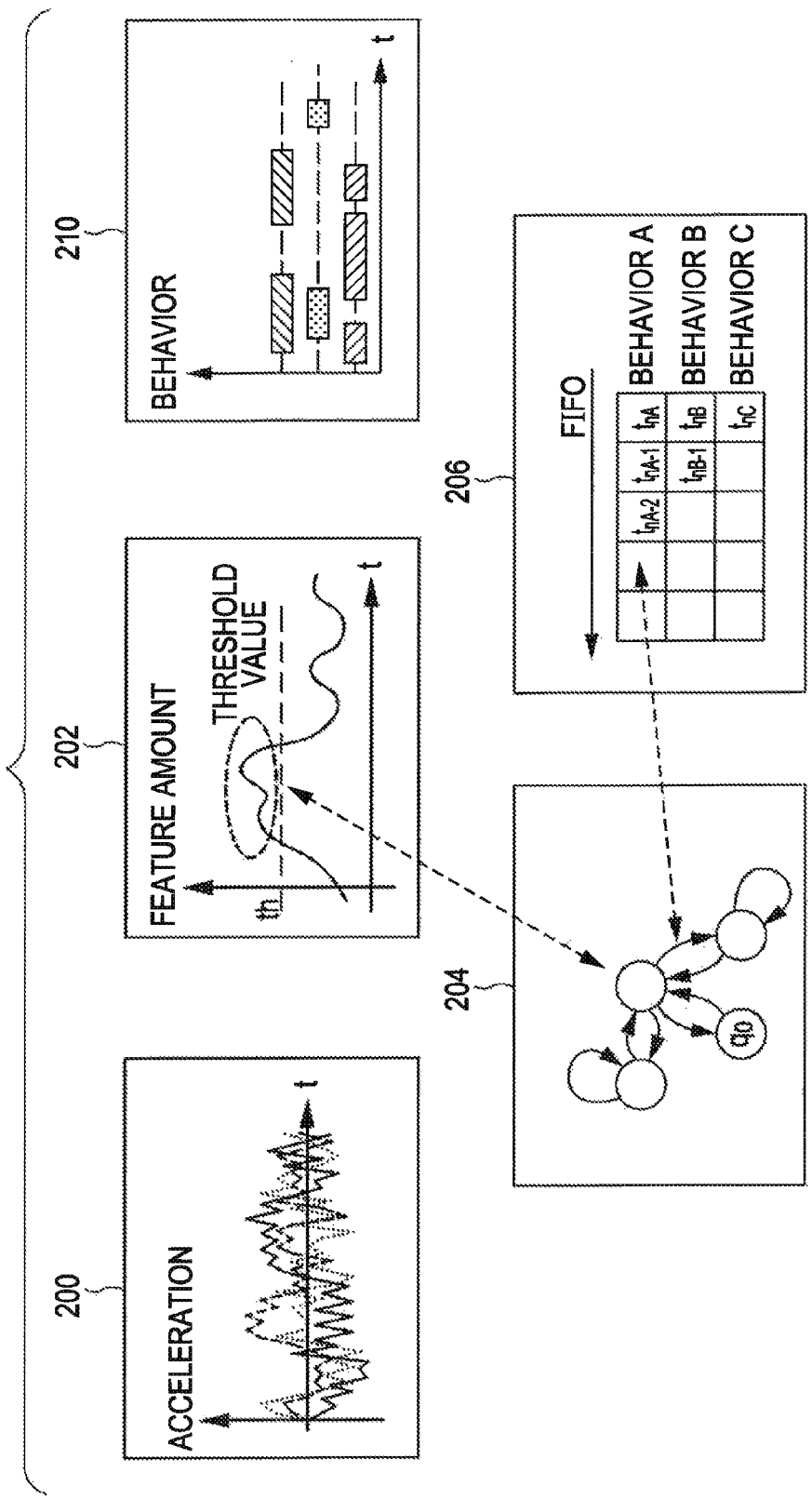
FIG. 6 is a diagram illustrating an overview of an information processing method of the information processing apparatus according to the embodiment of the invention.

FIG. 6 is a detailed diagram illustrating the behavior recognition function and the behavior information post-process function. First, the sensor data generator 110 generates the sensor data 200 based on the user behavior. Next, the behavior recognizing unit 112 recognizes the behavior exhibited by the user by performing a predetermined threshold value process on the sensor data 200 and generates the behavior information 202 that is the information indicating the behavior exhibited by the user. In addition, the behavior manager 114 manages the behavior information generated by the behavior recognizing unit 112 as data 206 in correspondence with the time point at which the behavior corresponding to the behavior information is exhibited. Next, the behavior information post-processing unit 116 performs a predetermined post-process on the behavior information managed by the behavior manager 114. The behavior information post-processing unit 116 performs a predetermined post-process on the data 206 of each behavior recorded in the FIFO manner. The detailed post-processing method will be described later. In this manner, the behavior information 210 that is subject to the post-process 204 is obtained, so that the accuracy of the behavior can be improved by the information processing apparatus 100.

4-2. Behavior Recognition Function

Figure 7:
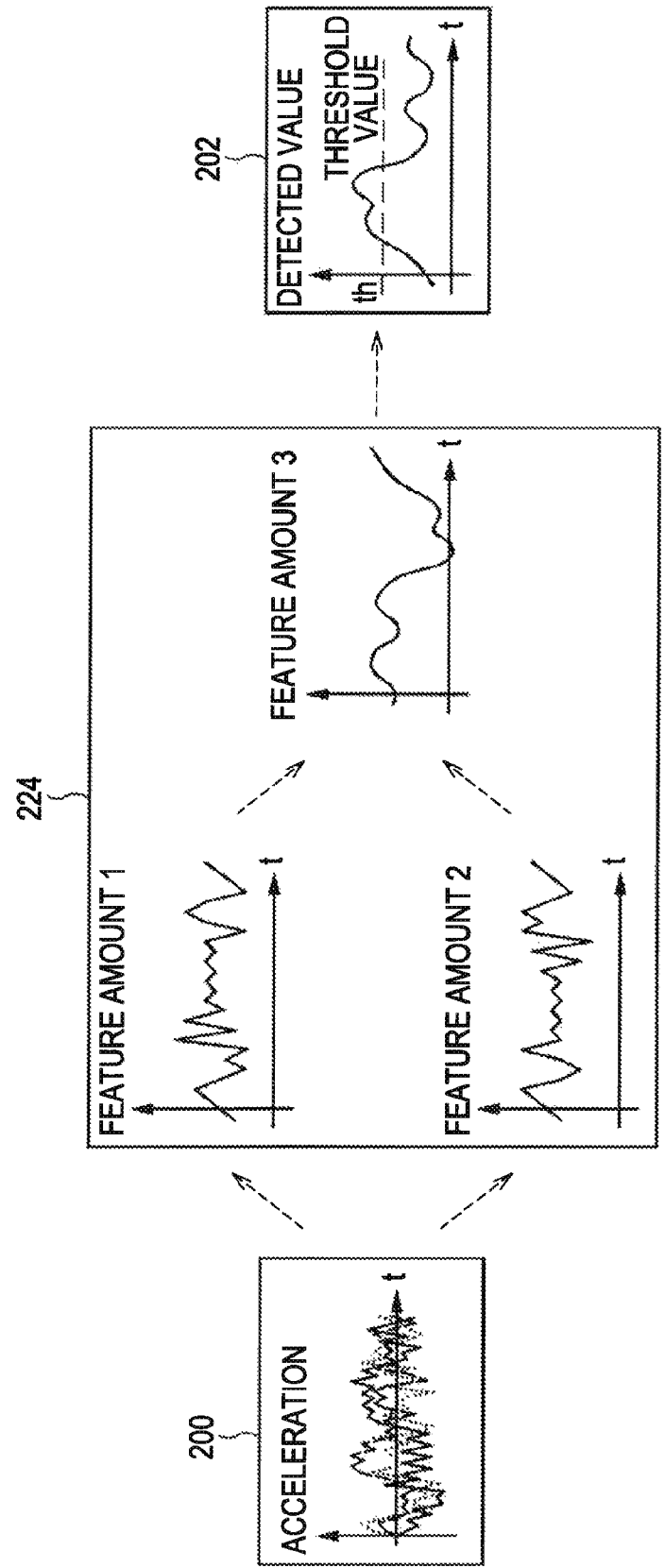
FIG. 7 is a diagram illustrating an overview of an information processing method of the information processing apparatus according to the embodiment of the invention.

FIG. 7 is a diagram illustrating the overview of the behavior recognition function. The behavior recognizing unit 112 generates the behavior information 202 for the sensor data 200 generated by the sensor data generator 110. More specifically, the behavior recognizing unit 112 that acquires the sensor data 200 allows the behavior determination unit 118 specified to each behavior to perform a unique process specified to each behavior in the sensor data processing unit 120. The sensor data processing unit 120 performs a predetermined process for each behavior (reference numeral 224) to generate the behavior information 202. The detailed method of the predetermined process will be described later. In this manner, the behavior recognizing unit 112 has the processing method specified to each behavior, so that each behavior may be recognized with a good accuracy.

4-3. Behavior Information Post-Process Function

Figure 8:
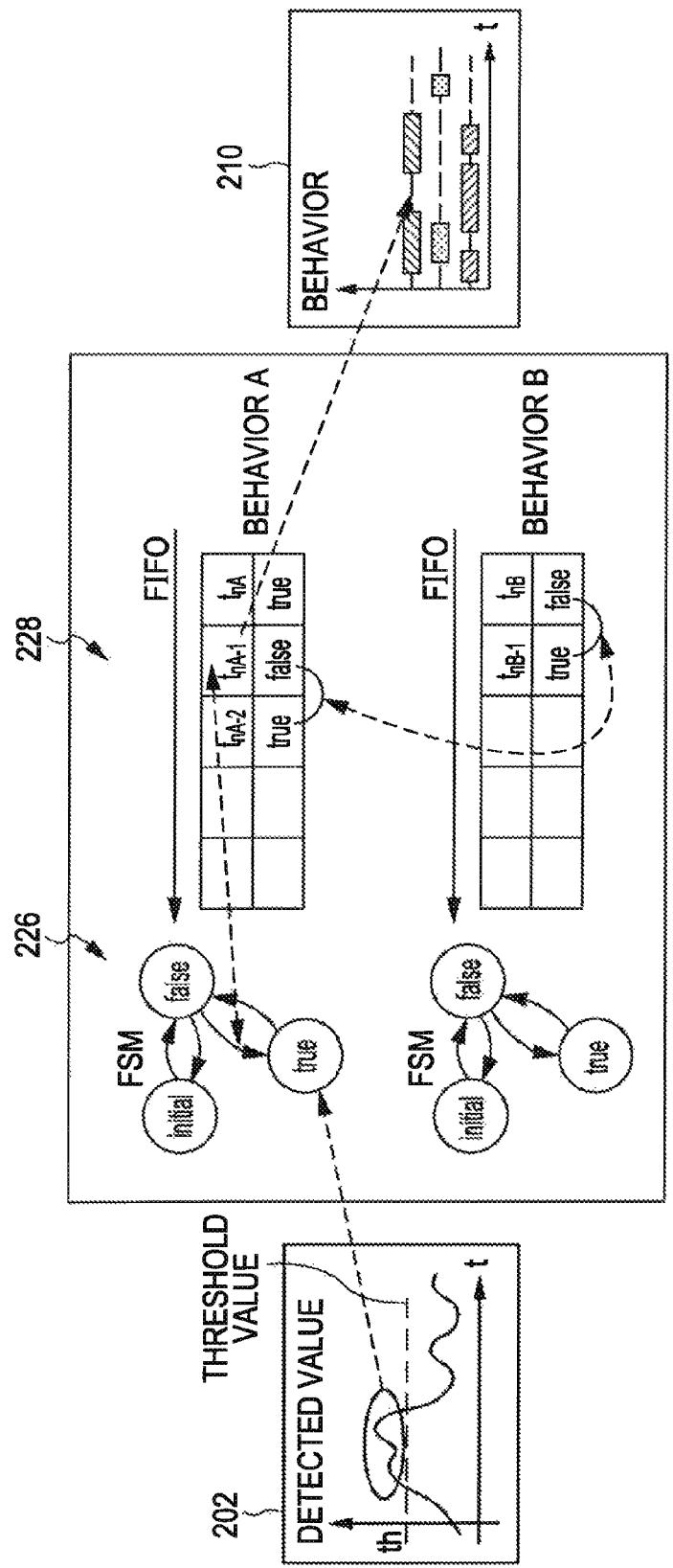
FIG. 8 is a diagram illustrating an overview of an information processing method of the information processing apparatus according to the embodiment of the invention.

FIG. 8 is a diagram illustrating the overview of the behavior information post-process function. The behavior manager 114 manages the behavior information generated by the behavior recognizing unit 112 as data 226 in correspondence with the time point at which the behavior corresponding to the behavior information is exhibited. Next, the behavior information post-processing unit 116 performs a predetermined post-process on the behavior information 226 managed by the behavior manager 114. The behavior information post-processing unit 116 performs a predetermined post-process on the data 228 of each behavior recorded in the FIFO manner. The post-process is performed by the exclusive behavior information re-processing unit 144, the false recognition behavior information re-processing unit 146, and the behavior information real-time adjusting unit 148. The detailed post-processing method will be described later. As a result, the behavior information 210 that is subject to the post-process may be obtained. In this manner, the predetermined post-process is performed on the behavior information generated by the behavior recognizing unit 112, so that the behavior information may be generated without false recognition in comparison with the real behavior of the user.

5. Application Examples of Information Processing Method in Information Processing Apparatus 100

Next, application examples of the information processing method will be described with reference to FIGS. 9 to 20. The information processing apparatus 100 according to the embodiment includes a behavior recognizing unit 112. The behavior recognizing unit 112 includes a behavior determination unit 118 and a sensor data processing unit 120. The behavior recognizing unit 112 includes a plurality of behavior determination units 118 that are specified to a specific behavior exhibited by the user. More specifically, the behavior determination units 118 include a stopped state determination unit 122, a walking/running state determination unit 124, a jumping state determination unit 126, a posture change determination unit 128, an elevator boarding determination unit 130, an electric train boarding determination unit 132, and a turning-to-the-right/turning-to-the-left determination unit 134. In the information processing apparatus 100 according to the embodiment, the behavior recognition functions specified to the behaviors are included, so that the behaviors may be recognized with a good accuracy. The sensor data processing unit 120 includes a sensor data calculation unit 136, a specific area remover 138, a lower area remover 140, and a sensor data storage unit 142 so as to perform predetermined processes for the behaviors according to instructions of the behavior determination units 118.

The sensor data calculation unit 136 performs a predetermined calculation on the sensor data. The specific area remover 138 removes a range excluding a predetermined area of the sensor data. The lower area remover 140 removes an area equal to or smaller than a predetermined value of the sensor data. The sensor data storage unit 142 records the sensor data in the FIFO manner. Hereinafter, the behavior recognition method for each behavior will be described in detail.

In addition, the sensor data that are generated by the sensor data generator 110 included in the information processing apparatus 100 according to the embodiment include acceleration sensor data and gyro sensor data. The acceleration sensor data include first acceleration sensor data, second acceleration sensor data, and third acceleration sensor data. The first acceleration sensor data are the data regarding acceleration according to a predetermined coordinate axis. In addition, the second acceleration sensor data are the data regarding acceleration according to a coordinate axis different from that of the first acceleration sensor data, for example, according to a coordinate axis perpendicular to the coordinate axis of the first acceleration sensor data. In addition, the third acceleration sensor data are the data regarding acceleration according to a coordinate axis different from those of the first acceleration sensor data and the second acceleration sensor data, for example, according to a coordinate axis perpendicular to the coordinate axes of the first acceleration sensor data and the second acceleration sensor data. Herein, as marked in FIGS. 11 to 17 referred to in the hereinafter description, the x-acc is an example of the first acceleration sensor data and indicates the acceleration sensor data in the X axis direction of the coordinate axes including three axes of the X axis, the Y axis, and the Z axis. In addition, the y-acc is an example of the second acceleration sensor data and indicates the acceleration sensor data in the Y axis direction. In addition, the z-acc is an example of the third acceleration sensor data and indicates the acceleration sensor data in the Z axis direction. In addition, the x-gyro is an example of the first gyro sensor data and indicates the gyro sensor data in the X axis direction of the coordinate axes including three axes of the X axis, the Y axis, and the Z axis. In addition, the y-gyro is an example of the second gyro sensor data and indicates the gyro sensor data in the Y axis direction. In addition, the z-gyro is an example of the third gyro sensor data and indicates the gyro sensor data in the Z axis direction.

Figure 9:
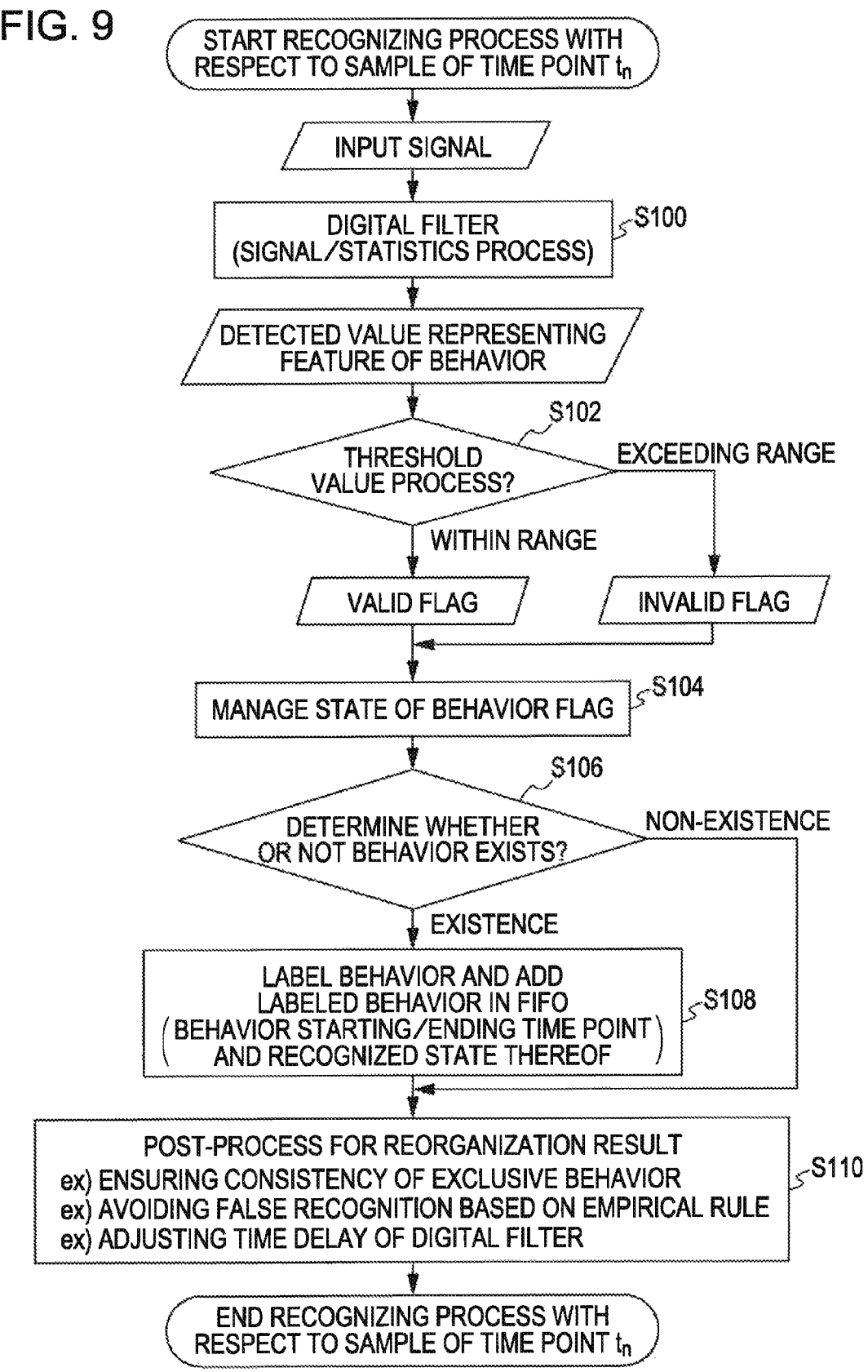
FIG. 9 is a diagram illustrating a flow of an information processing method of the information processing apparatus according to the embodiment of the invention.

5-1. Behavior Recognition Function and Behavior Information Post-Process Function First, a flow of a behavior recognition method and a behavior information post-processing method are described with reference to FIG. 9. FIG. 9 is a diagram illustrating a flow of the behavior recognition method and the behavior information post-processing method according to the embodiment. With respect to a sample (user behavior) at a time point $t_n$, the sensor data generator 110 generates sensor data as an input signal. The behavior recognizing unit 112 performs a digital filter process (signal/statistic process) on the sensor data (S100). As a result, the behavior recognizing unit 112 calculates a detected value representing a feature of each behavior to perform a threshold value process (S102). As the result thereof, in the case where the behavior recognizing unit 112 determines that the detected value exceeds a threshold value range, the behavior manager 114 erects an invalid flag to perform the flag state management for each behavior (S104). In addition, in the case where the behavior recognizing unit 112 determines that the detected value is within the threshold value range, the behavior manager 114 erects a valid flag to perform the flag state management for each behavior (S104). In addition, the behavior manager 114 determines whether or not a behavior exists (S106), and if the behavior exists, behavior is labeled and recorded in the FIFO manner (S108). The behavior manager 114 records starting/ending time points of behavior and a recognition state thereof. Next, the behavior information post-processing unit 116 performs a post-process for the recognition result (S110). As an example of the post-process, there is a process of ensuring the consistency of an exclusive behavior, which is performed by the exclusive behavior information re-calculation unit 144 of the behavior information post-processing unit 116. In addition, there is a process of avoiding a false recognition based on the empirical rule, which is performed by the false recognition behavior information re-calculation unit 146 of the behavior information post-processing unit 116. In addition, there is a process of adjusting a time delay of a digital filter, which is performed by the behavior information real-time adjusting unit 148 of the behavior information post-processing unit 116. In this manner, the recognition process for the sample at the time point $t_n$ is carried out. Particularly, a behavior recognition method having a digital filtering function corresponding to each behavior is described later in detail.

Figure 10:
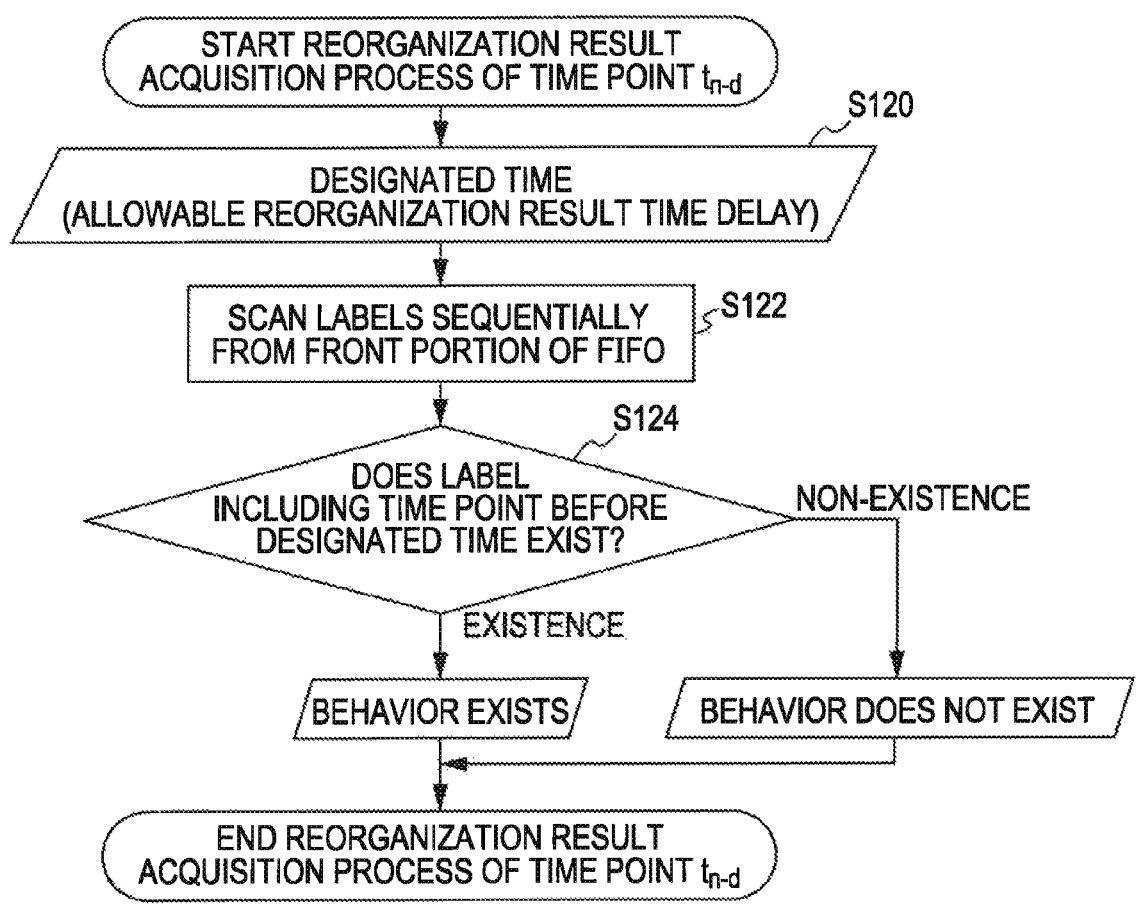
FIG. 10 is a diagram illustrating a flow of an information processing method of the information processing apparatus according to the embodiment of the invention.

In addition, the function of acquiring the recognition result of the past time point $t_{n-d}$ will be described with reference to FIG. 10. FIG. 10 is a diagram illustrating a flow of the behavior information post-process function. The behavior manager 114 calculates a time delay as a designated time for the recognition result of the time point $t_{n-d}$ (S120). The behavior manager 114 scans labels sequentially from the head of the data recorded in the FIFO manner (S122). Next, the behavior manager 114 determines whether or not the label exists at the time point before the designated time (S124).

As a result, it may be recognized whether or not the behavior exists at the time point $t_{n-d}$.

5-2. Method of Recognizing Whether or not the User Stops or Temporarily Stops

Figure 11:
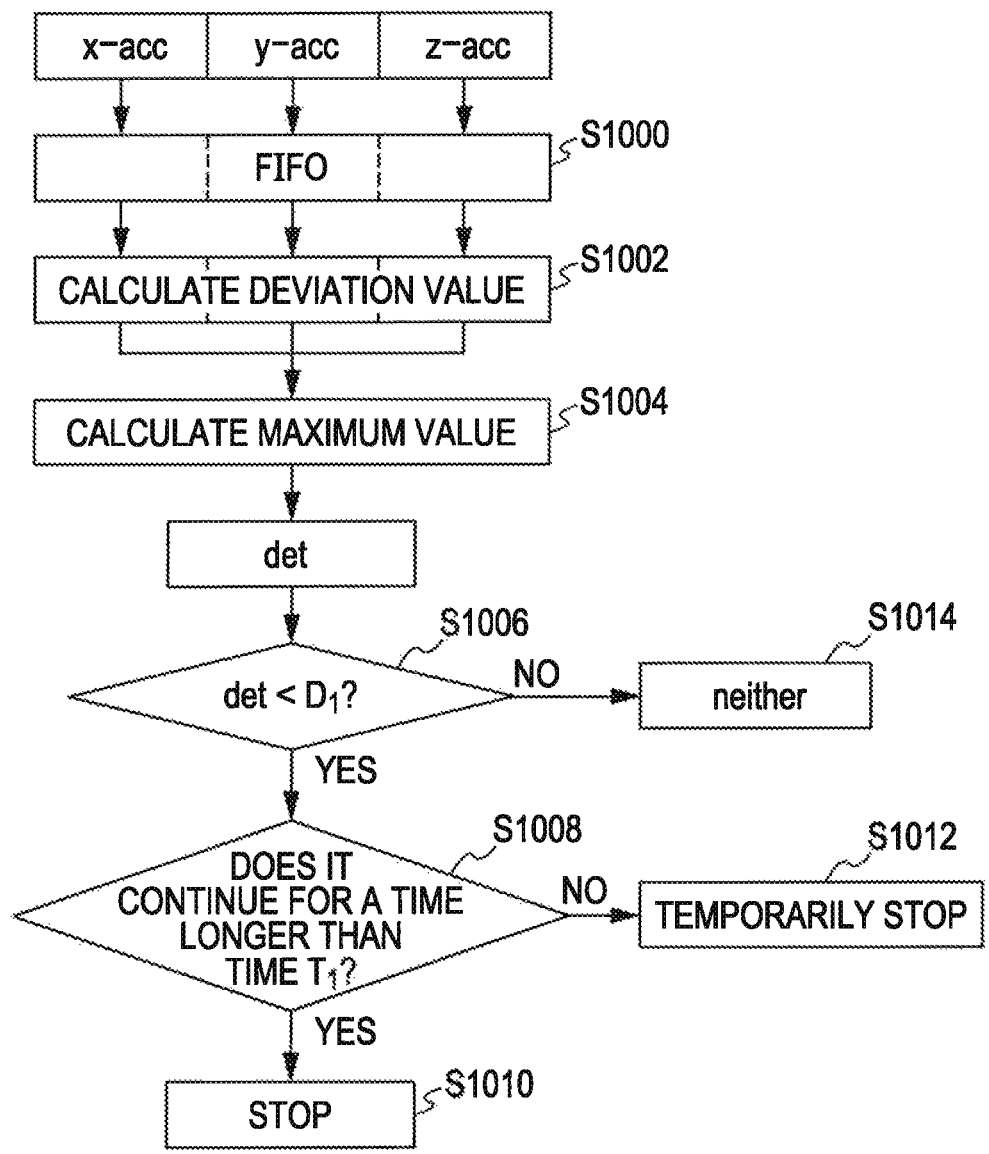
FIG. 11 is a diagram illustrating a flow of a method of recognizing stopping and temporary stopping in the information processing apparatus according to the embodiment of the invention.

First, a method of recognizing whether the user temporarily stops or stops will be described with reference to FIG. 11. FIG. 11 is a diagram illustrating a flow of the method of recognizing whether the user temporarily stops or stops in the behavior recognizing unit 112. First, the sensor data generator 110 senses the user behavior 156 and generates sensor data. Next, the behavior recognizing unit 112 acquires the sensor data from the sensor data generator 110. In order to recognize whether the user temporarily stops or stops, first, the stopped state determination unit 122 in the behavior determination unit 118 transmits to the sensor data processing unit 120 a signal for recognizing whether the user temporarily stops or stops. In addition, the sensor data processing unit 120 acquires the sensor data from the sensor data generator 110.

Next, the sensor data storage unit 142 records the x-acc, the y-acc, and the z-acc in the FIFO manner (S1000). After a predetermined amount of the data is recorded in the sensor data storage unit 142, the sensor data calculation unit 136 acquires the x-acc, the y-acc, and the z-acc from the sensor data storage unit 142. Herein, the predetermined data may be set to, for example, data corresponding to only a time set by the information processing apparatus 100 or data corresponding to only a time set by the user. Next, the sensor data calculation unit 136 calculates variance values of the x-acc, the y-acc, and the z-acc (S1002). In addition, next, the sensor data calculation unit 136 extracts the maximum variance value (det) for determining stopping, that is, the largest variance value among the variance values (S1004).

Next, the stopped state determination unit 122 acquires the maximum variance value for determining stopping from the sensor data processing unit 120. The stopped state determination unit 122 determines whether or not the maximum variance value for determining stopping is smaller than the stop recognition value $D_1$ in which the user is recognized as stopping (S1006). In the case where the maximum variance value for determining stopping is not smaller than the $D_1$, that is, equal to or larger than the $D_1$, the stopped state determination unit 122 determines that the user does not stop. In other words, the user exhibits some behavior. The stopped state determination unit 122 generates the behavior information indicating that the user does not stop (S1014).

On the other hand, in the case where the maximum variance value for determining stopping is smaller than $D_1$, the stopped state determination unit 122 determines whether or not the time smaller than $D_1$ in the maximum variance value continues to be longer than the stop recognition time $T_1$ (S1008). Herein, the stop recognition time $T_1$ is the minimum time in which the user is recognized as stopping by the stopped state determination unit 122. In the case where the time smaller than $D_1$ in the maximum variance value for determining stopping continues to be longer than $T_1$, the stopped state determination unit 122 determines that the user stops and generates the behavior information indicating that the user stops (S1010). On the other hand, in the case where the time smaller than $D_1$ in the maximum variance value for determining stopping does not continue to be longer than $T_1$, the stopped state determination unit 122 determines that the user temporarily stops and generates the behavior information indicating that the user temporarily stops (S1012). In addition, the $D_1$ and the $T_1$ may be set in advance by the information processing apparatus 100, or the $D_1$ and the $T_1$ may be set in the information processing apparatus 100 by the user. In this manner, in the information processing apparatus 100 according to the embodiment, by the sensor data process function specified to each user behavior, it may be recognized with a good accuracy whether the user stops, temporarily stops, or exhibits a behavior other than these two behaviors.

5-3. Method of Recognizing Whether or not the User Walks or Runs

Figure 12:
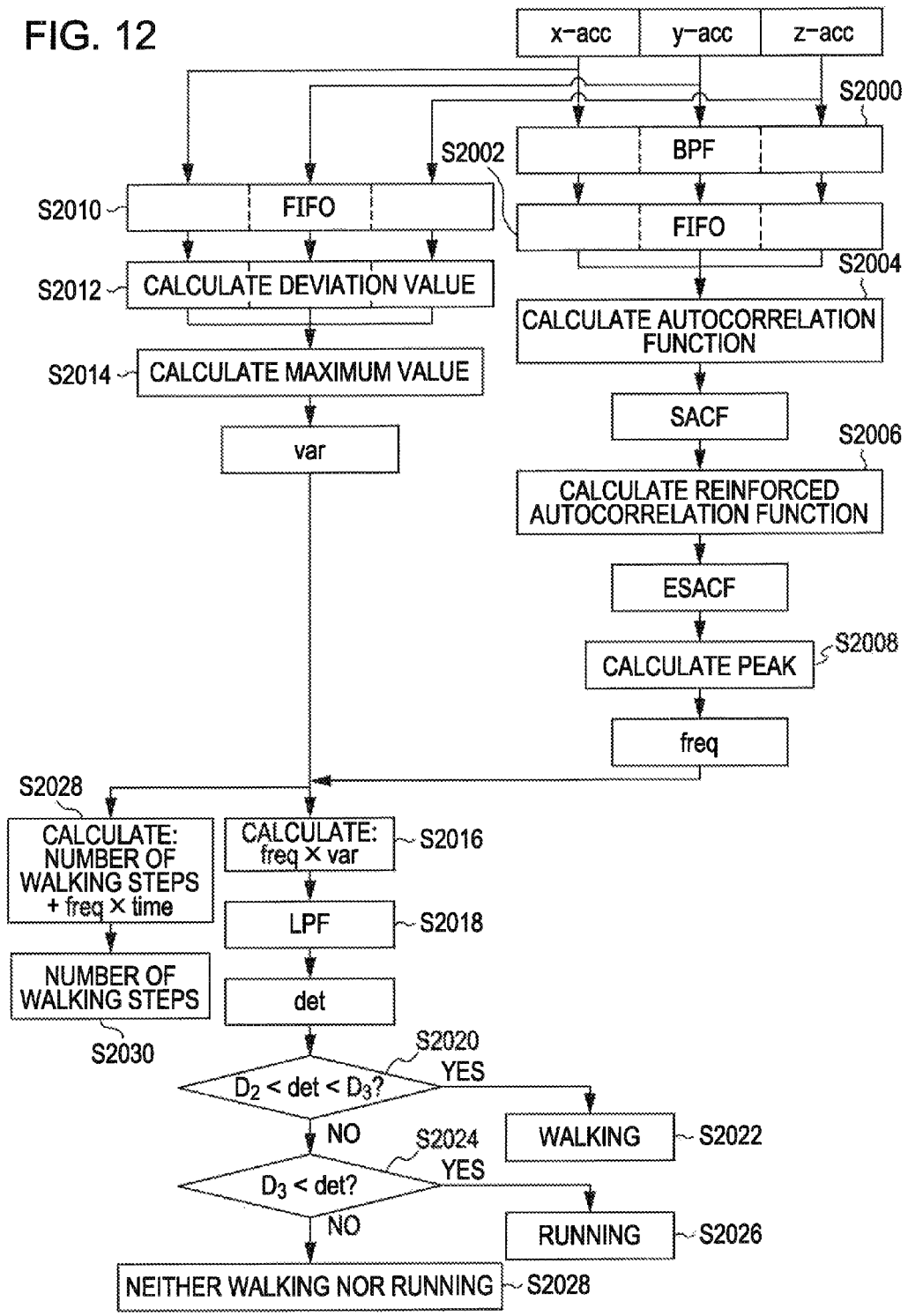
FIG. 12 is a diagram illustrating a flow of a method of recognizing walking and running in the information processing apparatus according to the embodiment of the invention.

Next, a method of recognizing whether a user walks or runs will be described with reference to FIG. 12. FIG. 12 is a diagram illustrating a flow of the method of recognizing whether the user walks or runs in the behavior recognizing unit 112. First, the sensor data generator 110 senses the user behavior 156 and generates sensor data. Next, the behavior recognizing unit 112 acquires the sensor data from the sensor data generator 110. In order to recognize whether to walk or to run, first, the walking/running state determination unit 124 in the behavior determination unit 118 transmits to the sensor data processing unit 120 a signal for recognizing whether the user walks or runs. In addition, the sensor data processing unit 120 acquires the sensor data from the sensor data generator 110.

Next, the specific area remover 138 removes a frequency in a range excluding a walking/running recognition frequency area, in which the user is recognized as walking or running, in the x-acc, the y-acc, and the z-acc (S2000). In other words, the specific area remover 138 may function as a bandpass filter (BPF). In addition, the walking/running recognition frequency area may be set by the information processing apparatus 100 in advance. Otherwise, the information processing apparatus 100 acquires the behavior pattern independent of the user, and the walking/running recognition frequency area may be set according to the user behavior. Next, the sensor data storage unit 142 records the x-acc, the y-acc, and the z-acc, which are subject to the above-described process, in the FIFO manner (S2002). Next, after a predetermined amount of the data is recorded in the sensor data storage unit 142, the sensor data calculation unit 136 acquires the x-acc, the y-acc, and the z-acc from the sensor data storage unit 142. Herein, the predetermined data may be set to, for example, data corresponding to only a time set by the information processing apparatus 100.

Next, the sensor data calculation unit 136 calculates a summary autocorrelation function (SACF) for the x-acc, the y-acc, and the z-acc, of which a predetermined amount of the data is recorded in the FIFO manner. In addition, the sensor data calculation unit 136 calculates an enhanced simplified autocorrelation function (ESACF) based on the simplified autocorrelation function (SACF) (S2006). The occurrence of the peak of the SACF according to the time elapse corresponds to the periodic motion of the walking and running in the sensor data. However, the SACF also includes data having a frequency that is an integral multiple of the frequency representing the actual walking and running. Therefore, the sensor data calculation unit 136 may remove redundant peak data and obtain only the frequency representing the actual walking and running by calculating the ESACF. As a result, the sensor data calculation unit 136 may calculate the frequency (freq) for determining the walking/running by calculating the peak based on the ESACF (S2008).

In addition, after the sensor data processing unit 120 acquires the sensor data from the sensor data generator 110, the sensor data storage unit 142 records the x-acc, the y-acc, and the z-acc in the FIFO manner (S2010). Next, after a predetermined amount of the data is recorded in the sensor data storage unit 142, the sensor data calculation unit 136 acquires the x-acc, the y-acc, and the z-acc from the sensor data storage unit 142. Herein, the predetermined data may be set to, for example, data corresponding only to a time set by the information processing apparatus 100.

Next, the sensor data calculation unit 136 calculates variance values of the x-acc, the y-acc, and the z-acc, of which a predetermined amount of the data is recorded in the FIFO manner (S2012). In addition, next, the sensor data calculation unit 136 extracts the maximum variance value (var) for determining the walking/running that is the largest variance value among the variance values (S2014).

Next, the sensor data calculation unit 136 calculates a product of the frequency (freq) for determining the walking/running and the maximum variance value (var) for determining the walking/running (S2016). In other words, to give a brief description, the number of steps per unit time corresponding to the walking/running is represented by the freq, and the magnitude of the motion corresponding to the walking/running is represented by the var. In other words, the walking/running may be determined by the number of steps and the magnitude of the motion, and as described later, in the case where the product of the freq and the var is within a range of a predetermined area, it is determined that the user walks. In addition, in the case where the product exceeds the predetermined area, it is determined that the user runs. In addition, in the case where the product does not reach the predetermined area, it is determined that the user neither walks nor runs.

Next, the lower area remover 140 removes a frequency area, in which the user may be falsely recognized to walk or run, from the product and calculates the walking/running determination data for determining whether the user walks or runs (S2018). In other words, the lower area remover 140 may function as a lowpass filter (LPF). In addition, the removed frequency area may be set by the information processing apparatus 100 in advance. Otherwise, the information processing apparatus 100 acquires the behavior pattern independent of the user, and the frequency area may be set according to the user behavior.

Next, the walking/running state determination unit 124 acquires the walking/running determination data from the sensor data processing unit 120. The walking/running state determination unit 124 determines whether or not the value of the walking/running determination data is larger than the minimum walking recognition value $D_2$ that is a lower limit value for recognizing that the user walks (S2020). In addition, the walking/running state determination unit 124 determines whether or not the value of the walking/running determination data is smaller than the maximum walking recognition value $D_3$ that is an upper limit value for recognizing that the user walks (S2020). In the case where the value of the walking/running determination data is larger than the $D_2$ and smaller than the $D_3$, the walking/running state determination unit 124 generates the behavior information indicating that the user walks (S2022). In addition, the walking/running state determination unit 124 determines whether or not the value of the walking/running determination data is larger than the $D_3$ (S2024). In the case where the value of the walking/running determination data is larger than the $D_3$, the walking/running state determination unit 124 generates the behavior information indicating that the user runs (S2026). In addition, in the case where the value of the walking/running determination data is equal to or smaller than the $D_2$, the walking/running state determination unit 124 generates the behavior information indicating that the user neither walks nor runs (S2028). In this manner, in the information processing apparatus 100 according to the embodiment, by the sensor data process function specified to each user behavior, it may be recognized with a good accuracy whether the user walks, runs, or exhibits a behavior other than the two behaviors.

On the other hand, the sensor data calculation unit 136 may integrate the freq (S2028). In addition, according to the result of the integration, the walking/running state determination unit 124 may generate the behavior information about the number of steps for a predetermined time. In other words, according to the information processing apparatus 100, it may be recognized how long the user walks for a predetermined time. In addition, the predetermined time may be, for example, a time set by the information processing apparatus 100 or a time set by the user.

5-4. Method of Recognizing Whether or not the User Jumps

Figure 13:
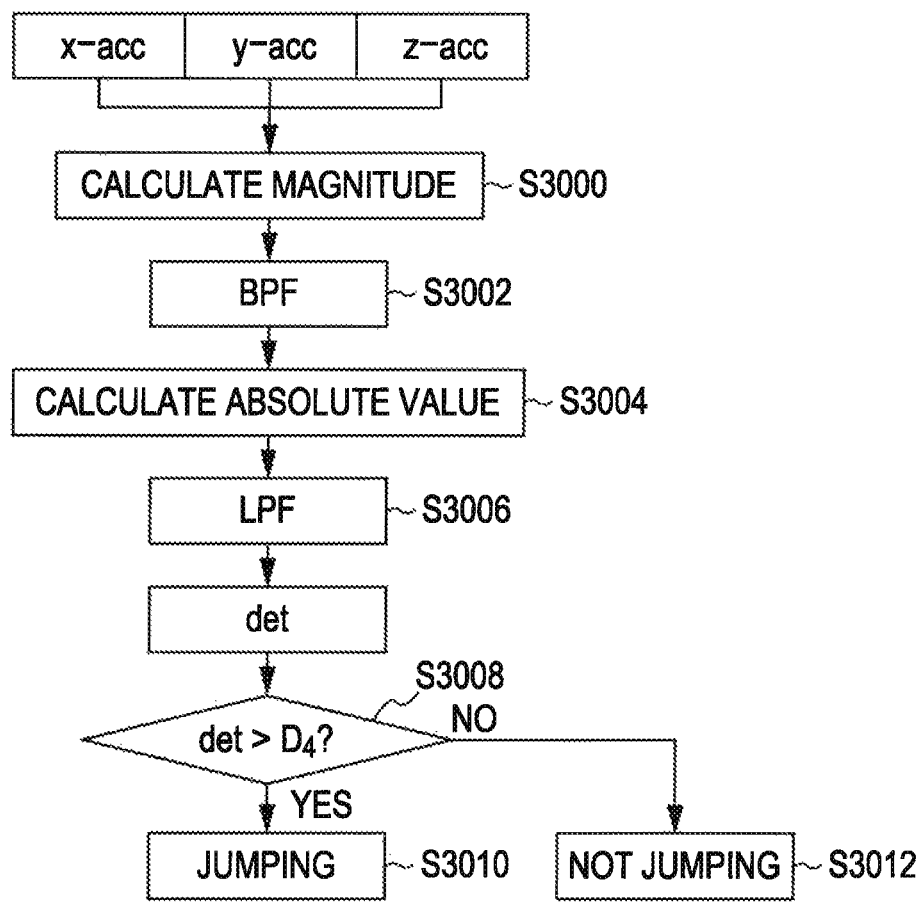
FIG. 13 is a diagram illustrating a flow of a method of recognizing jumping in the information processing apparatus according to the embodiment of the invention.

Next, a method of recognizing whether or not the user jumps will be described with reference to FIG. 13. FIG. 13 is a diagram illustrating a flow of the method of recognizing whether or not the user jumps in the behavior recognizing unit 112. First, the sensor data generator 110 senses the user behavior 156 and generates sensor data. Next, the behavior recognizing unit 112 acquires the sensor data from the sensor data generator 110. In order to recognize whether or not the user jumps, first, the jumping state determination unit 126 in the behavior determination unit 118 transmits to the sensor data processing unit 120 a signal for recognizing whether or not the user jumps. In addition, the sensor data processing unit 120 acquires the sensor data from the sensor data generator 110.

Next, the sensor data calculation unit 136 calculates a jumping acceleration that is expressed by magnitudes in the x-acc, the y-acc, and the z-acc (S3000). Next, the specific area remover 138 removes a frequency in a range excluding the jumping recognition value area, in which the user is recognized as jumping at the jumping acceleration (S3002). In other words, the specific area remover 138 may perform a function as a band pass filter (BPF). In addition, the jumping recognition value area may be set by the user or set by the information processing apparatus 100 in advance. Otherwise, the information processing apparatus 100 acquires the behavior pattern independently of the user, and the jumping recognition value area may be set according to the user behavior. In addition, as a result, the specific area remover 138 calculates a corrected jumping acceleration that is an absolute value for recognizing whether or not the user jumps (S3004). More specifically, for example, in comparison with the jumping acceleration, in the corrected jumping acceleration, the data component caused by the shaking or the vibration of the information processing apparatus 100, which may occur at the time of jumping, is removed. Next, the lower area remover 140 removes a frequency area, in which the user may be falsely recognized to jump at the corrected jumping acceleration (S3006). In other words, the lower area remover 140 may perform a function as a lowpass filter (LPF). In addition, the removed frequency area may be set by the user or set by the information processing apparatus 100 in advance. Otherwise, the information processing apparatus 100 acquires the behavior pattern independently of the user, and the frequency area may be set according to the user behavior. In addition, as a result, the lower area remover 140 calculates a jumping state determination value (det) for determining whether or not the user jumps.

Next, the jumping state determination unit 126 acquires the jumping state determination value from the sensor data processing unit 120. The jumping state determination unit 126 determines whether or not the jumping state determination value is larger than the minimum jumping recognition value $D_4$ that is a lower limit value for recognizing that the user jumps (S3008). In the case where the value of the jumping state determination value is larger than the minimum jumping recognition value $D_4$, the jumping state determination unit 126 generates the behavior information indicating that the user jumps (S3010). On the other hand, in the case where the value of the jumping state determination value is equal to or smaller than the minimum jumping recognition value $D_4$, the jumping state determination unit 126 generates the behavior information indicating that the user does not jump (S3012). In this manner, in the information processing apparatus 100 according to the embodiment, by the sensor data process function specified to each user behavior, it may be recognized with a good accuracy whether or not the user jumps.

5-5. Method of Recognizing Whether or not the User Sits or Stands

Figure 14:
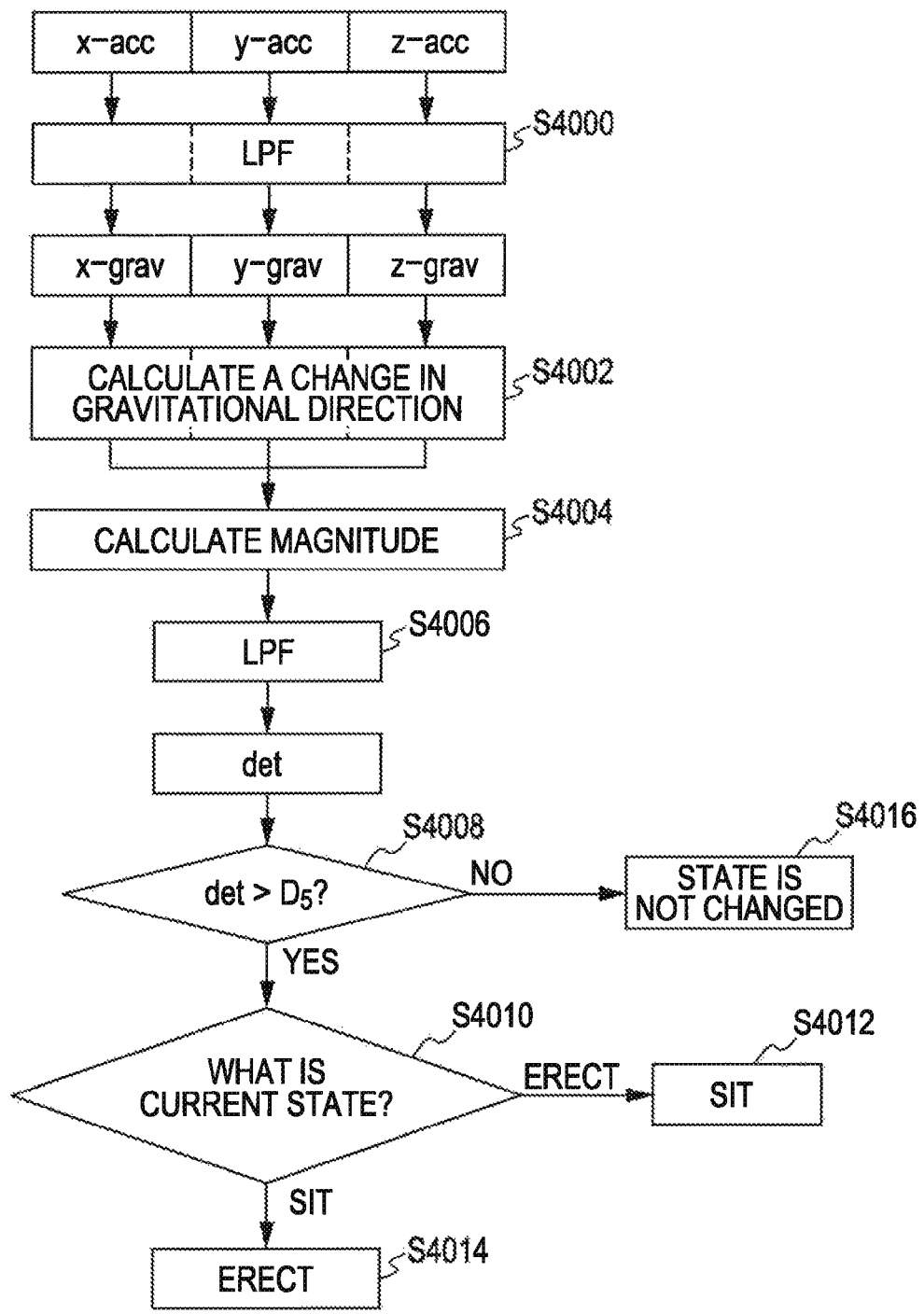
FIG. 14 is a diagram illustrating a flow of a method of recognizing posture change in the information processing apparatus according to the embodiment of the invention.

Next, a method of recognizing whether the user sits or stands will be described with reference to FIG. 14. FIG. 14 is a diagram illustrating a flow of the method of recognizing whether the user sits or stands in the behavior recognizing unit 112. First, the sensor data generator 110 senses the user behavior 156 and generates sensor data. Next, the behavior recognizing unit 112 acquires the sensor data from the sensor data generator 110. The recognition of the sitting or the standing includes the recognition of the standing of the user who did sit and the recognition of the sitting of the user who did stand. In other words, it is to recognize the change in the user's posture. In this manner, in order to recognize whether or not the user changes posture, first, the posture change determination unit 128 in the behavior determination unit 118 transmits to the sensor data processing unit 120 a signal for recognizing whether or not the user changes posture. In addition, the sensor data processing unit 120 acquires the sensor data from the sensor data generator 110.

Next, the lower area remover 140 removes a frequency area, in which the user may be falsely recognized as changing posture in the x-acc, the y-acc, and the z-acc (S4000). The lower area remover 140 may function as a lowpass filter (LPF). In addition, the removed first frequency area may be set by the information processing apparatus 100 in advance. Otherwise, the information processing apparatus 100 acquires the behavior pattern independently of the user, and the first frequency area may be set according to user behavior. As a result, the lower area remover 140 calculates the x-grav based on the x-acc, the y-grav based on the y-acc, and the z-grav based on the z-acc. The x-grav is an example of the first gravity data based on the first acceleration sensor data and indicates the acceleration sensor data in the X axis direction of the coordinate axes including three axes of the X axis, the Y axis, and the Z axis. The y-grav is an example of the second gravity data based on the second acceleration sensor data and indicates the acceleration sensor data in the Y axis direction of the coordinate axes including three axes of the X axis, the Y axis, and the Z axis. The z-grav is an example of the third gravity data based on the third acceleration sensor data and indicates the acceleration sensor data in the Z axis direction of the coordinate axes including three axes of the X axis, the Y axis, and the Z axis.

Next, the sensor data calculation unit 136 calculates the value $\delta(\text{x-grav})$ representing how much the calculated x-grav is changed from the x-grav before a predetermined time (S4002). The $\delta(\text{x-grav})$ is an example of the first gravity change data. In addition, the sensor data calculation unit 136 calculates the $\delta(\text{y-grav})$ representing how much the calculated y-grav is changed from the y-grav before a predetermined time (S4002). The $\delta(\text{y-grav})$ is an example of the second gravity change data. In addition, the sensor data calculation unit 136 calculates the $\delta(\text{z-grav})$ representing how much the calculated z-grav is changed from the z-grav before a predetermined time (S4002). The $\delta(\text{z-grav})$ is an example of the first gravity change data. Next, the sensor data calculation unit 136 calculates posture changed values representing the magnitudes of the $\delta(\text{x-grav})$, the $\delta(\text{y-grav})$, and the $\delta(\text{z-grav})$ (S4004). The posture changed value allows the change in user posture to be recognized.

Next, the lower area remover 140 removes an area of the posture changed value, in which the user may be falsely recognized as changing posture (S4006). The lower area remover 140 may function as a lowpass filter (LPF). As a result, the lower area remover 140 calculates the posture change determination value (det) for determining whether or not the user changes posture. In addition, the removed area may be set by the information processing apparatus 100 in advance. Otherwise, the information processing apparatus 100 acquires the behavior pattern independently of the user, and the area may be set according to the user behavior.

Next, the posture change determination unit 128 acquires the posture change determination value from the sensor data processing unit 120. In the case where the minimum posture change recognition value $D_5$ that is a lower limit value for recognizing that the user changes the posture is larger than the posture change determination value, the posture change determination unit 128 determines that the user changes the posture (S4008). In the case where the user changes the posture, the posture change determination unit 128 determines whether the user is already standing or sitting (S4010). In the case where the user is already standing, the user changes posture to sitting, the posture change determination unit 128 generates the behavior information indicating that the user sits (S4012). In addition, in the case where the user is already sitting, the user changes posture into standing, and the posture change determination unit 128 generates the behavior information indicating that the user stands (S4014). In other words, on the other hand, in the case where the posture change determination value is equal to or smaller than the $D_5$, the user does not change posture, and the posture change determination unit 128 generates the behavior information indicating that there is no change in the state with respect to the change in posture (S4016). In this manner, in the information processing apparatus 100 according to the embodiment, by the sensor data process function specified to each user behavior, it may be recognized with a good accuracy whether or not the user changes posture. In other words, it may be recognized based on the determination of the change in user posture whether the user is in the sitting state or in the standing state.

Figure 15:
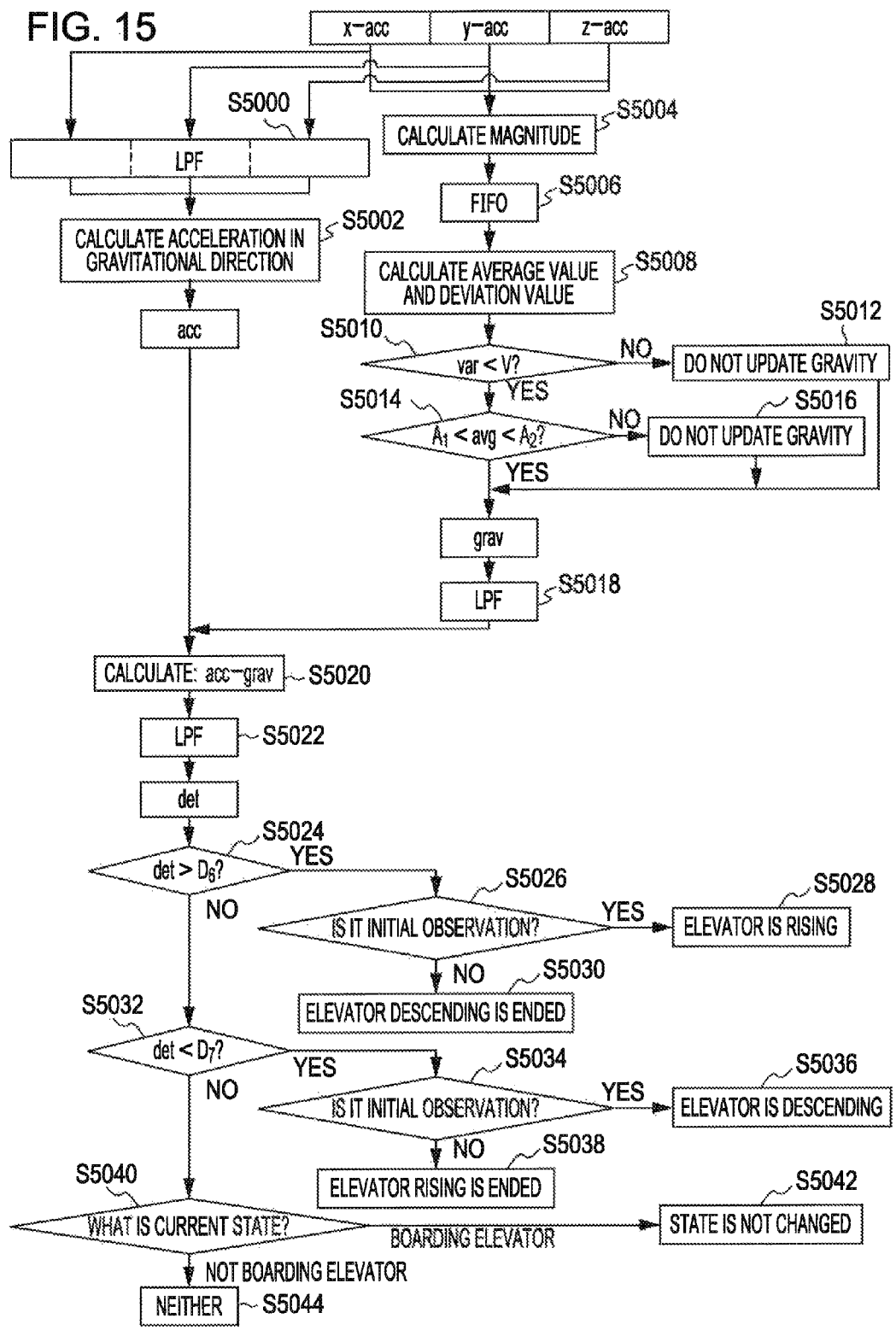
FIG. 15 is a diagram illustrating a flow of a method of recognizing boarding an elevator in the information processing apparatus according to the embodiment of the invention.

5-6. Method of Recognizing Whether or not the User Rises or Descends in Elevator Next, a method of recognizing whether or not the user boards an elevator will be described with reference to FIG. 15. FIG. 15 is a diagram illustrating a flow of the method of recognizing whether or not the user boards an elevator in the behavior recognizing unit 112. First, the sensor data generator 110 senses the user behavior 156 and generates sensor data. Next, the behavior recognizing unit 112 acquires the sensor data from the sensor data generator 110. In this manner, in order to recognize whether or not the user boards the elevator, first, the elevator boarding determination unit 130 in the behavior determination unit 118 transmits to the sensor data processing unit 120 a signal for recognizing whether or not the user boards an elevator. In addition, the sensor data processing unit 120 acquires the sensor data from the sensor data generator 110.

Next, the lower area remover 140 removes a frequency area, in which the acceleration in the gravity direction may be falsely recognized, based on the x-acc, the y-acc, and the z-acc (S5000). The lower area remover 140 may function as a lowpass filter (LPF). In addition, the removed frequency area may be set by the information processing apparatus 100 in advance. Otherwise, the information processing apparatus 100 acquires the behavior pattern independently of the user, and the frequency area may be set according to the user behavior. Next, the sensor data calculation unit 136 calculates the gravity direction acceleration sensor data (acc) based on the x-acc, the y-acc, and the z-acc, from which the frequency area is removed (S5002).

On the other hand, the sensor data calculation unit 136 calculates the gravity adjusting data represented by the magnitudes of the x-acc, the y-acc, and the z-acc of allowing the value of the gravity to be adjusted (S5004) and records the gravity adjusting data in the sensor data storage unit 142 (S5006). The sensor data calculation unit 136 calculates the gravity adjusting variance value (var) that is the variance value of the gravity adjusting data, of which a predetermined data amount is recorded (S5008). In addition, the sensor data calculation unit 136 calculates the gravity adjusting average data that are the average value of the gravity adjusting data, of which a predetermined data amount is recorded (S5008).

Next, the sensor data calculation unit 136 determines whether or not the gravity adjusting variance value is smaller than the maximum allowable gravity adjusting variance value $V_1$ that is the maximum variance value of allowing the gravity adjusting (S5010). In the case where the gravity adjusting variance value is equal to or larger than the $V_1$, the sensor data calculation unit 136 does not update the value of gravity (S5012). The function is performed in the case where fine adjustment for gravity is necessary in the direction of the information processing apparatus 100 accompanying the user. This is because the change in the gravity after the adjustment is too large and the difference from the actual phenomenon is too large in the case where the gravity adjusting variance value is equal to or larger than the $V_1$.

On the other hand, the case where the gravity adjusting variance value is smaller than maximum allowable gravity adjusting variance value $V_1$ that is the maximum variance value of allowing the gravity adjusting will be described. Sequentially, the sensor data calculation unit 136 determines whether or not the gravity adjusting average data is larger than the minimum allowable gravity average value $A_1$ that is the minimum average value of allowing the gravity adjusting and determines whether or not the gravity adjusting average data is smaller than the maximum allowable gravity average value $A_2$ that is the maximum average value of allowing the gravity adjusting (S5014). In the case where the value of the gravity adjusting average data is larger than the $A_1$ and smaller than the $A_2$, the value of the gravity adjusting average data is considered to be the gravity after the adjusting. On the other hand, in the case where the value of the gravity adjusting average data is equal to or smaller than the $A_1$ or equal to or larger than the $A_2$, the sensor data calculation unit 136 does not update the value of gravity (S5016).

Next, the lower area remover 140 removes a lower area, in which the gravity may be falsely recognized, from the gravity adjusting average data (S5018). The lower area remover 140 may function as a lowpass filter (LPF). In addition, the removed frequency area may be set by the information processing apparatus 100 in advance. Otherwise, the information processing apparatus 100 acquires the behavior pattern independently of the user, and the frequency area may be set according to the user behavior. As a result, the lower area remover 140 calculates the corrected gravity adjusting average data.

Next, the sensor data calculation unit 136 calculates a difference between the gravity direction acceleration sensor data and the corrected gravity adjusting average data (S5020).

In other words, it is determined based on the change in the gravity due to the user behavior whether or not the user boards the elevator. Next, the lower area remover 140 removes a frequency area, in which the user may be falsely recognized to board the elevator, from the difference and calculates elevator rising determination data for determining whether or not the user boards the elevator. The removed frequency area may be set by the information processing apparatus 100 in advance. Otherwise, the information processing apparatus 100 acquires the behavior pattern independently of the user, and the frequency area may be set according to the user behavior.

Next, the elevator boarding determination unit 130 acquires the elevator rising determination data from the sensor data processing unit 120. The elevator boarding determination unit 130 determines whether the elevator rising determination data is larger or smaller than the predetermined value $D_6$ (S5024) and determines whether the elevator rising determination data is larger or smaller than the predetermined value $D_7$ (S5032). The predetermined value $D_6$ is the lower limit value for recognizing that the user starts to rise in the elevator and an example of the $D_\alpha$. The predetermined value $D_7$ is the upper limit value for recognizing that the user starts to descend in the elevator and an example of the $D_\beta$. More specifically, in the case where elevator rising determination data is larger than the predetermined value $D_6$ at first and, after that, smaller than the predetermined value $D_7$, the elevator boarding determination unit 130 determines that the user is rising in the elevator. Next, the elevator boarding determination unit 130 generates the behavior information indicating that the user is rising in the elevator (S5024, S5026, S5028, S5032, S5034, and S5038). In addition, in the case where the elevator rising determination data is larger than the predetermined value $D_7$ at first and, after that, smaller than the predetermined value $D_6$, the elevator boarding determination unit 130 determines that the user is descending in the elevator. Next, the elevator boarding determination unit 130 generates the behavior information indicating that the user is descending in the elevator (S5024, S5026, S5030, S5032, S5034, and S5036). According to this method, since the user behavior is recognized based on the acceleration sensor data corresponding to, for example, the situation where the user is rising in the elevator or the situation after that, the false recognition by a behavior that is performed by the user during the boarding of the elevator may be avoided.

In addition, in the case where the elevator rising determination data is equal to or smaller than the predetermined value $D_6$ and equal to or larger than the predetermined value $D_7$, the elevator boarding determination unit 130 determines the user behavior (S5040). In the case where the user boards the elevator, the elevator boarding determination unit 130 generates the behavior information indicating that the elevator is not in the accelerated and decelerated states (S5042). In other words, according to the behavior information, it may be recognized that the elevator is stopped or in a uniform velocity motion. In addition, in the case where the user does not board the elevator, the elevator boarding determination unit 130 generates the behavior information indicating that the user does not board the elevator (S5044). In this manner, in the information processing apparatus 100 according to the embodiment, by the sensor data process function specified to each user behavior, it may be recognized with a good accuracy whether the user boards the elevator to be rising or descending. In other words, by detecting the acceleration or deceleration in the up and down directions of the user, it may be recognized whether or not to board the elevator.

5-7. Method of Recognizing Whether or not the User Boards Electric Train

Figure 16:
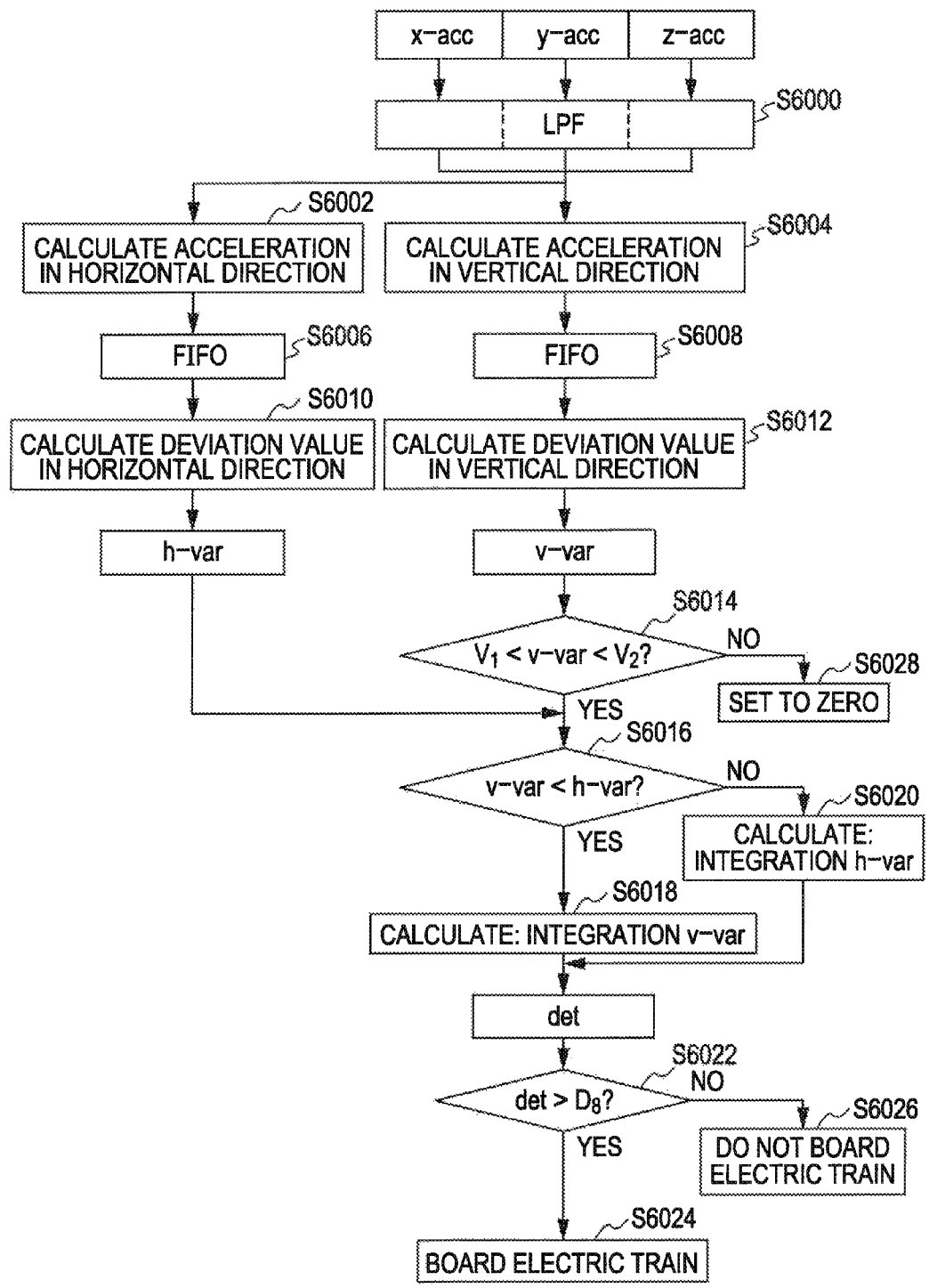
FIG. 16 is a diagram illustrating a flow of a method of recognizing boarding an electric train in the information processing apparatus according to the embodiment of the invention.

Next, a method of recognizing whether or not the user boards an electric train will be described with reference to FIG. 16. FIG. 16 is a diagram illustrating a flow of the method of recognizing whether or not the user boards an electric train in the behavior recognizing unit 112. First, the sensor data generator 110 senses the user behavior 156 and generates sensor data. Next, the behavior recognizing unit 112 acquires the sensor data from the sensor data generator 110. In this manner, in order to recognize whether or not the user boards the electric train, first, the electric train boarding determination unit 132 in the behavior determination unit 118 transmits to the sensor data processing unit 120 a signal for recognizing whether or not to board the electric train. In addition, the sensor data processing unit 120 acquires the sensor data from the sensor data generator 110.

Next, the lower area remover 140 removes a frequency area, in which the user may be falsely recognized to board the electric train, based on the x-acc, the y-acc, and the z-acc (S6000). The lower area remover 140 may function as a lowpass filter (LPF). In addition, the removed frequency area may be set by the information processing apparatus 100 in advance. Otherwise, the information processing apparatus 100 acquires the behavior pattern independently of the user, and the frequency area may be set according to the user behavior. Next, the sensor data calculation unit 136 calculates the horizontal direction acceleration sensor data and the vertical direction acceleration sensor data based on the x-acc, the y-acc, and the z-acc, from which the frequency area is removed (S6002 and S6004). Herein, the horizontal direction is the direction parallel to the ground on which the electric train drives. In addition, the vertical direction is the direction perpendicular to the horizontal direction.

Next, the sensor data storage unit 142 records a predetermined data amount of the horizontal direction acceleration sensor data and a predetermined data amount of the vertical direction acceleration sensor data in the FIFO manner (S6006 and S6008). Herein, the predetermined data may be set to, for example, data corresponding only to a time set by the information processing apparatus 100 or data corresponding to a time set by the user. The sensor data calculation unit 136 calculates the horizontal direction variance value (h-var) from the horizontal direction acceleration sensor data which are recorded in the FIFO manner (S6010). In addition, the sensor data calculation unit 136 calculates the vertical direction variance value (v-var) from the vertical direction acceleration sensor data which are recorded in the FIFO manner (S6012). The horizontal direction variance value (h-var) represents the degree of shaking, that is, vibration in the horizontal direction when the electric train drives. In addition, the vertical direction variance value (v-var) represents the degree of shaking, that is, vibration in the vertical direction when the electric train drives.

In addition, it is determined whether or not the vertical direction variance value (v-var) is larger than the minimum allowable vertical variance value $V_1$ that is the vertical direction variance value that is the minimum allowable and smaller than the maximum allowable vertical variance value $V_2$ that is the vertical direction variance value that is the maximum allowable (S6014). In the case where vertical direction variance value (v-var) is equal to or smaller than the $V_1$ or in the case where the vertical direction variance value is equal to or larger than the $V_2$, the sensor data calculation unit 136 sets the later-described electric train boarding determination data (det) to zero. In other words, in the case where the vertical direction variance value (v-var) is equal to or smaller than $V_1$ or in the case where the vertical direction variance value is equal to larger than the $V_2$, since the vertical direction variance value is not suitable for representing the degree of shaking, that is, the vibration when the electric train drives, the sensor data calculation unit 136 corrects the electric train boarding determination data (det) as zero. In addition, the $V_1$ and the $V_2$ are, for example, values set by the information processing apparatus 100.

Next, the sensor data calculation unit 136 determines which one of the vertical direction variance value and the horizontal direction variance value is smaller (S6016). In the case where the vertical direction variance value (v-var) is small, the sensor data calculation unit 136 calculates an integration value of a predetermined amount of the vertical direction variance value (v-var) (S6018). The predetermined amount may be, for example, only an amount set by the information processing apparatus 100 or only an amount set by the user. In addition, in the case where the horizontal direction variance value (h-var) is small, the sensor data calculation unit 136 calculates an integration value of a predetermined amount of the horizontal direction variance value (h-var) (S6020). The predetermined amount may be, for example, only an amount set by the information processing apparatus 100 or only an amount set by the user. By using the integration, the sensor data calculation unit 136 calculates electric train boarding determination data (det) for determining whether or not the user boards the electric train. In addition, as described above, in the case where the vertical direction variance value (v-var) is equal to or smaller than the $V_1$, or in the case where the vertical direction variance value (v-var) is equal to or larger than the $V_2$, the sensor data calculation unit 136 sets the later-described electric train boarding determination data (det) to zero (S6028).

Next, the electric train boarding determination unit 132 acquires the electric train boarding determination data from the sensor data processing unit 120. The electric train boarding determination unit 132 determines whether or not the electric train boarding determination data is larger than the minimum electric train boarding recognition value $D_8$ that is a lower limit value for recognizing that the user boards the electric train (S6022). In the case where the electric train boarding determination data is larger than the $D_8$, the electric train boarding determination unit 132 determines that the user boards the electric train. In this case, the electric train boarding determination unit 132 generates the behavior information indicating that the user boards the electric train (S6024). On the other hand, in the case where the electric train boarding determination data is equal to or smaller than the $D_8$, the electric train boarding determination unit 132 determines that the user does not board the electric train (S6026). In this case, the electric train boarding determination unit 132 generates the behavior information indicating that the user does not board the electric train (S6026). In this manner, in the information processing apparatus 100 according to the embodiment, by the sensor data process function specified to each user behavior, it may be recognized with a good accuracy whether the user boards the electric train.

In addition, similarly to the method of recognizing whether or not the user boards an elevator, in the recognizing whether or not the user boards an electric train, the information processing apparatus 100 considers the state from the accelerated state to the decelerated state of the electric train. In other words, in the case where the user boards the electric train and the electric train stops at a station, as described later, a flag "false" may be erected as a result of the recognition. In other words, in the case where the electric train stops or in the case where the electric train arrives and the user gets off the electric train to walk, the electric train boarding determination unit 132 determines that the user does not board the electric train. In this case, as described later, the behavior information post-processing unit 116 performs a predetermined post-process. In other words, in the case where a predetermined condition is satisfied, if the user boards the electric train or is boarding the electric train, a post-process may be performed based on the state from the accelerated state to the decelerated state of the electric train.

Figure 17:
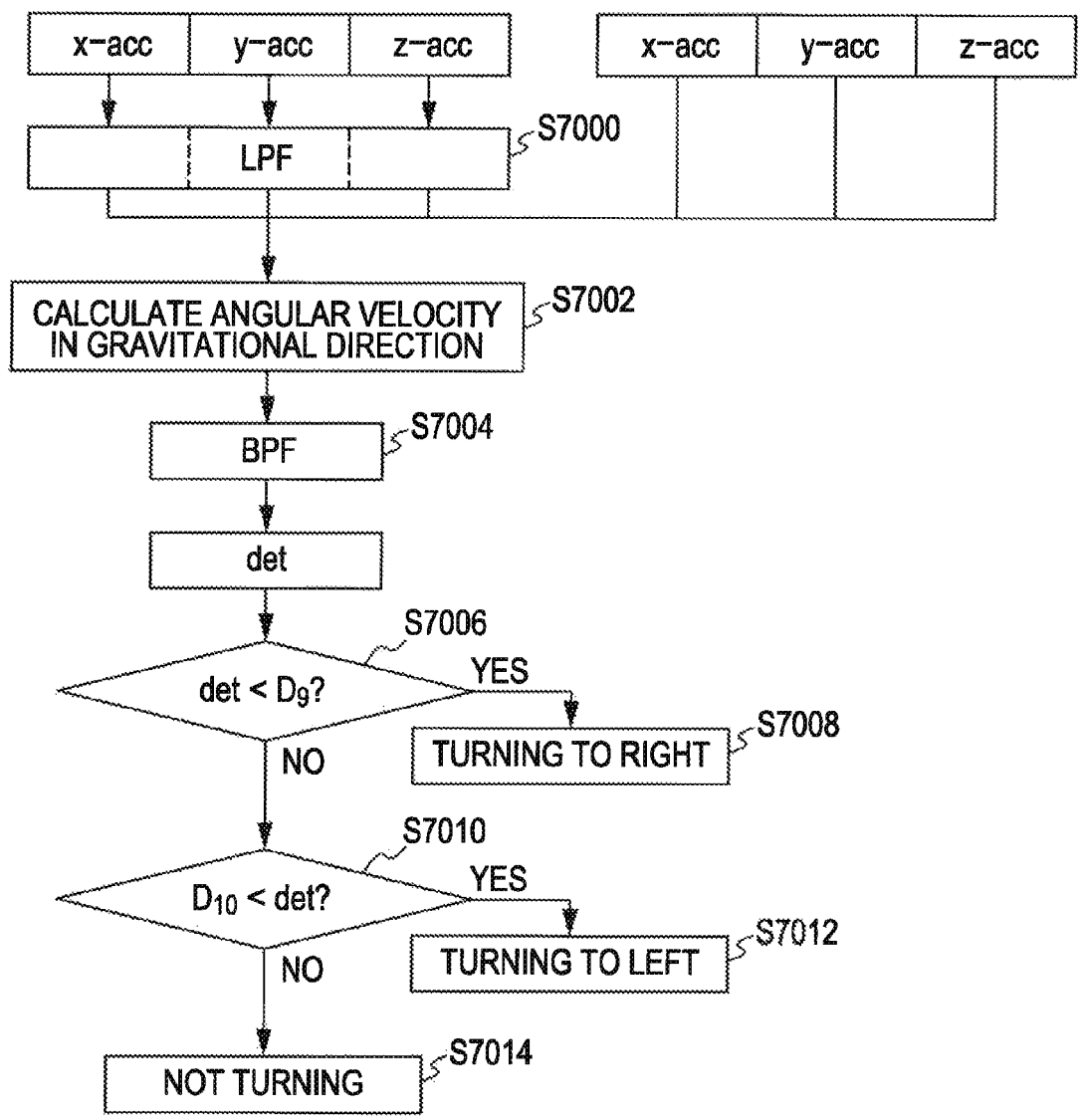
FIG. 17 is a diagram illustrating a flow of a method of recognizing turning-to-the-right or turning-to-the-left in the information processing apparatus according to the embodiment of the invention.

5-8. Method of Recognizing Whether or not the User Turns to the Right or to the Left Next, a method of recognizing whether the user turns to the right or the left will be described with reference to FIG. 17. FIG. 17 is a diagram illustrating a flow of the method of recognizing whether the user turns to the right or the left in the behavior recognizing unit 112. First, the sensor data generator 110 senses the user behavior 156 and generates sensor data. Next, the behavior recognizing unit 112 acquires the sensor data from the sensor data generator 110. In this manner, in order to recognize whether the user turns to the right or the left, first, the turning-to-the-right/turning-to-the-left determination unit 134 in the behavior determination unit 118 transmits to the sensor data processing unit 120 a signal for recognizing whether the user turns to the right or the left. In addition, the sensor data processing unit 120 acquires the sensor data from the sensor data generator 110.

Next, the lower area remover 140 removes a frequency area, in which the user may be falsely recognized as turning to the right or to the left, based on the x-acc, the y-acc, and the z-acc (S7000). The lower area remover 140 may function as a lowpass filter (LPF). In addition, the removed frequency area may be set by the user or set by the information processing apparatus 100 in advance. Otherwise, the information processing apparatus 100 acquires the behavior pattern independently of the user, and the frequency area may be set according to the user behavior.

The sensor data calculation unit 136 calculates the angular velocity in the gravity direction based on the x-acc, the y-acc, the z-acc, the x-gyro, the y-gyro, and the z-gyro, from which the frequency area is removed (S7002). Next, the specific area remover 138 removes a value in a range excluding the curve recognition area, in which the user is recognized as turning to the right or to the left, from the angular velocity and calculates the corrected angular velocity (det) (S7004). The specific area remover 138 may function as a bandpass filter (BPF). In addition, the curve recognition area may be set by the user or set by the information processing apparatus 100 in advance. Otherwise, the information processing apparatus 100 acquires the behavior pattern independently of the user, and the curve recognition area may be set according to the user behavior.

Next, the turning-to-the-right/turning-to-the-left determination unit 134 acquires the corrected angular velocity from the sensor data processing unit 120. The turning-to-the-right/turning-to-the-left determination unit 134 determines whether or not the corrected angular velocity is smaller than the maximum turning-to-the-right recognition value $D_9$ that is an upper limit value for recognizing that the user turns to the right (S7006). In the case where the corrected angular velocity is smaller than the $D_9$, the turning-to-the-right/turning-to-the-left determination unit 134 generates the behavior information indicating that the user turns to the right (S7008). On the other hand, in the case where the corrected angular velocity is equal to or larger than the $D_9$ and larger than the minimum turning-to-the-left recognition value $D_{10}$ that is a lower limit value for recognizing that the user turns to the left, the turning-to-the-right/turning-to-the-left determination unit 134 determines that the user turns to the left (S7010). In the case where the corrected angular velocity is larger than the $D_{10}$, the turning-to-the-right/turning-to-the-left determination unit 134 generates the behavior information indicating that the user turns to the left (S7012). In addition, in the case where the corrected angular velocity is equal to or larger than the $D_9$ and equal to or smaller than the $D_{10}$, the turning-to-the-right/turning-to-the-left determination unit 134 generates the behavior information indicating that the user neither turns to the right nor turns to the left (S7014). Herein, in the embodiment, the $D_9$ has a negative value, and the $D_{10}$ has a positive value. In this manner, in the information processing apparatus 100 according to the embodiment, by the sensor data process function specified to each user behavior, it may be recognized with a good accuracy whether the user turns to the right or to the left.

5-9. Behavior Information Post-Processing Method

Figure 18:
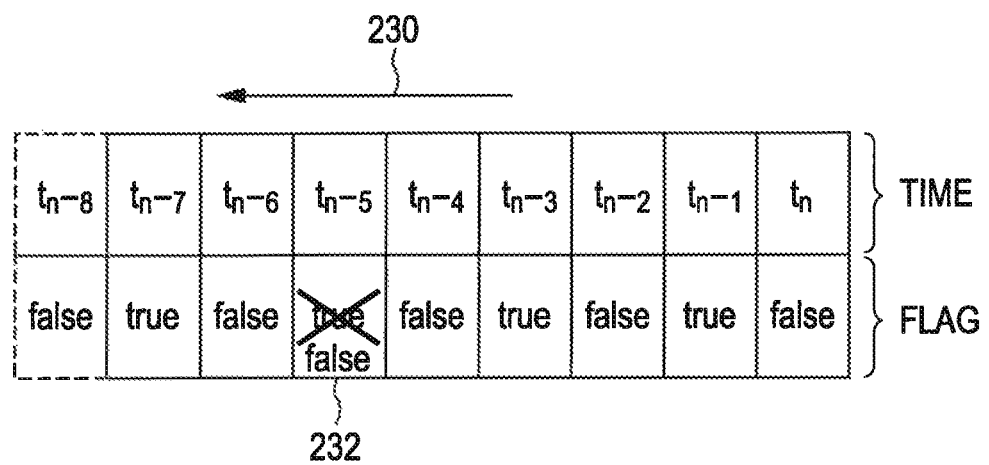
FIG. 18 is a diagram illustrating a behavior information managing method in the information processing apparatus according to the embodiment of the invention.

Next, the behavior information post-process function will be described with reference to FIGS. 18 to 20. FIG. 18 is a diagram illustrating a concept representing a state that, after the behavior information is managed by the behavior manager 114, the result of the behavior recognition is determined by the behavior information post-processing unit 116 and labeled. The arrow 230 indicates a scan direction of the FIFO. The behavior manager 114 manages the behavior information in correspondence with the time point at which the behavior corresponding to the behavior information is exhibited. Next, the behavior information post-processing unit 116 may erect a flag "true" indicating that the behavior is exhibited or a flag "false" indicating that the behavior is not exhibited every predetermined sampling rate. The predetermined sampling rate may be, for example, 32 Hz.

The behavior information post-processing unit 116 may perform a re-process for changing the content of the flag into content different from the original content. For example, the exclusive behavior information re-processing unit 144 included in the behavior information post-processing unit 116 re-processes the behavior information corresponding to each behavior every unit time based on an exclusive characteristic in that the user is not allowed to exhibit two or more behaviors simultaneously. Next, the exclusive behavior information re-processing unit 144 may change the content of the flag into content different from the original content. The exclusive characteristics are described more in detail. As shown in the following Table 1, for example, the user is not allowed to perform walking, running, and jumping simultaneously. However, in the behavior information generating process of the behavior recognizing unit 112 described above, it may be determined that walking, running, and jumping are simultaneously exhibited by the user. Herein, the exclusive behavior information re-processing unit 144 re-processes the behavior information corresponding to the behaviors that have an exclusive relationship every unit time. As shown in Table 1, the state "stopped" and the state "temporarily stopped", of which the exclusive relationship is denoted by A, have an exclusive relationship. In other words, these behavior states do not simultaneously occur. In addition, the state "walking", the state "running", and the state "jumping", of which the exclusive relationship is denoted by B, have an exclusive relationship. In other words, these behavior states do not simultaneously occur. In addition, the state "sitting" and the state "standing", of which the exclusive relationship is denoted by C, have an exclusive relationship. In other words, these behavior states do not simultaneously occur. In addition, the state "rising in elevator", the state "descending in elevator", and the state "boarding an electric train", of which the exclusive relationship is denoted by D, have an exclusive relationship. In other words, these behavior states do not simultaneously occur. In addition, the state "turning-to-the-right" and the state "turning-to-the-left", of which the exclusive relationship is denoted by E, have an exclusive relationship. In other words, these behavior states do not simultaneously occur. In this case, as to which one of the behavior states is selected, the exclusive behavior information re-processing unit 144 may perform a statistical process on which one of the behavior states may be easily selected with respect to the relationship between the previous and next behaviors, for example, based on the user's previous behavior information managed by the behavior manager 114. In addition, the other selection method may be used. The non-selected behavior information is excluded by the exclusive behavior information re-processing unit 144. The exclusive behavior information re-processing unit 144 may generate behavior information indicating that there is no behavior. In any case, the exclusive behavior information re-processing unit 144 corrects the portion denoted by the flag "true" shown by reference numeral 232 to be denoted by the flag "false".

TABLE 1

| Exclusive Relation | Type of Behavior | Type of Sensor |
| --- | --- | --- |
| A | Stop | Only Acceleration Sensor |
| A | Temporarily Stop | Only Acceleration Sensor |
| B | Walk | Only Acceleration Sensor |
| B | Run | Only Acceleration Sensor |
| B | Jump | Only Acceleration Sensor |
| C | Sit | Only Acceleration Sensor |
| C | Stand | Only Acceleration Sensor |
| D | Rise in Elevator | Only Acceleration Sensor |
| D | Descend in Elevator | Only Acceleration Sensor |
| D | Board Electric Train | Only Acceleration Sensor |
| E | Turn to the Right | Acceleration Sensor And Gyro Sensor |
| E | Turn to the Left | Acceleration Sensor And Gyro Sensor |

In addition, FIG. 19 shows that time delay for the process occurs in the behavior information obtained by the process of the behavior recognizing unit 112 with respect to the sensor data. For example, the behavior processed at the time point $t_n$ is actually the behavior performed at the time point $t_n'$. The behavior information post-processing unit 116 includes a behavior information real-time adjusting unit 148. The behavior information real-time adjusting unit 148 recognizes the time delay of each behavior, so that the behavior information real-time adjusting unit 148 may obtain the accurate recognition time point of each behavior by correcting the $t_n$ with the $t_n'$.

In addition, the behavior information post-processing unit 116 also includes a false recognition behavior information re-processing unit 146. In the case where the time necessary to exhibit a behavior is extremely short, the false recognition behavior information re-processing unit 146 treats the behavior information corresponding to the behavior as noise to consider that the actual behavior is not exhibited. For example, even in the case where the behavior recognizing unit 112 generates the behavior information indicating that the user "runs", if the time necessary to run is extremely short, the false recognition behavior information re-processing unit 146 performs a re-process of treating the behavior information as noise. In addition, the false recognition behavior information re-processing unit 146 treats the behavior information corresponding to the behavior that is not allowed to be exhibited originally as the behavior that is not exhibited actually. For example, if the behavior recognizing unit 112 recognizes the "walking" state from the "sitting" state of the user, it is determined again that the user is not "sitting" but "standing". In this manner, in the case where the behavior information corresponding to each behavior does not satisfy a behavior information necessary condition necessary to exhibit each behavior, the false recognition behavior information re-processing unit 146 corrects the behavior information corresponding to the behavior.

Figure 20:
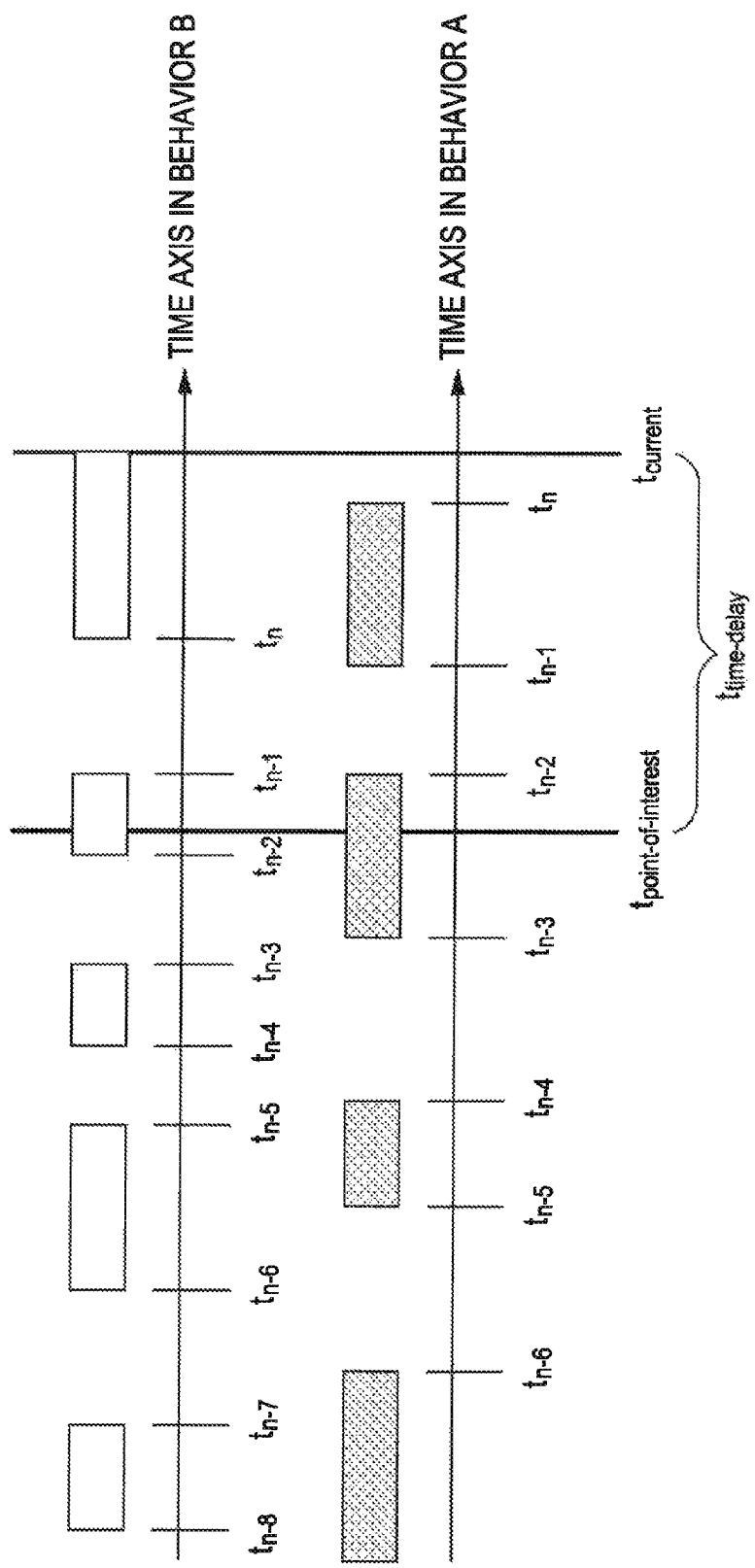
FIG. 20 is a diagram illustrating a behavior information post-processing method in the information processing apparatus according to the embodiment of the invention.

Next, FIG. 20 conceptually illustrates a state where the behavior manager 114 acquires the existence of the behavior at a time point ($t_{point-of-interest}$) before a designated time ($t_{time-delay}$) from the current time point ($t_{current}$) with respect to the result of the recognition of the two pieces of behavior information stored in the FIFO manner. As shown in FIG. 20, for example, the existence position of the to is different between the behavior A and the behavior B in the time axis. More specifically, after the process described with reference to FIG. 18 and the process described with reference to FIG. 19 are performed by the behavior information post-processing unit 116, each piece of behavior information in the state shown in FIG. 20 is recorded in the FIFO. In this manner, since each piece of behavior information is recorded and since time adjustment is performed on each piece of past behavior information, for example, the behavior manager 114 can easily transmit the past behavior information to the data controller 150.

6. Modified Examples of First Embodiment

Figure 22:
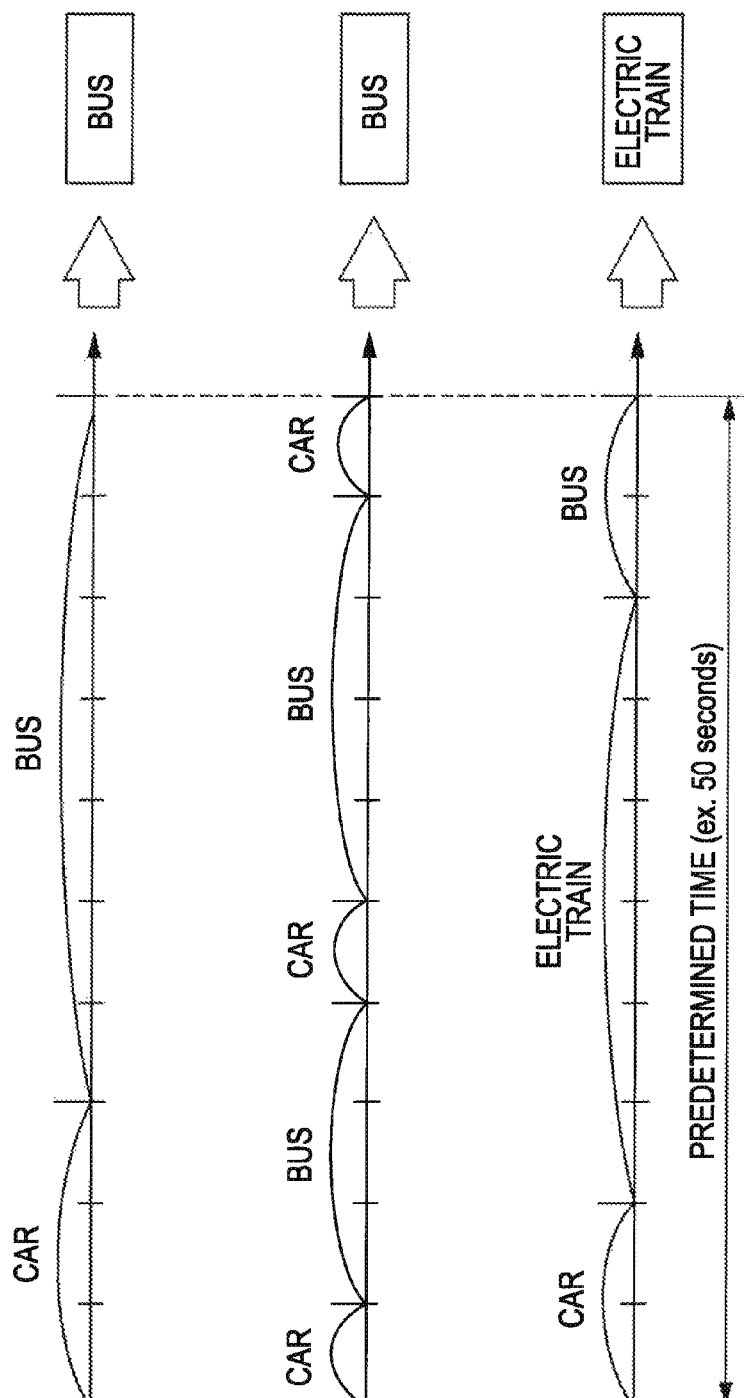
FIGS. 22A to 22C are diagrams illustrating examples of an information processing method in the modified example of the information processing apparatus according to the embodiment of the invention.
Figure 23:
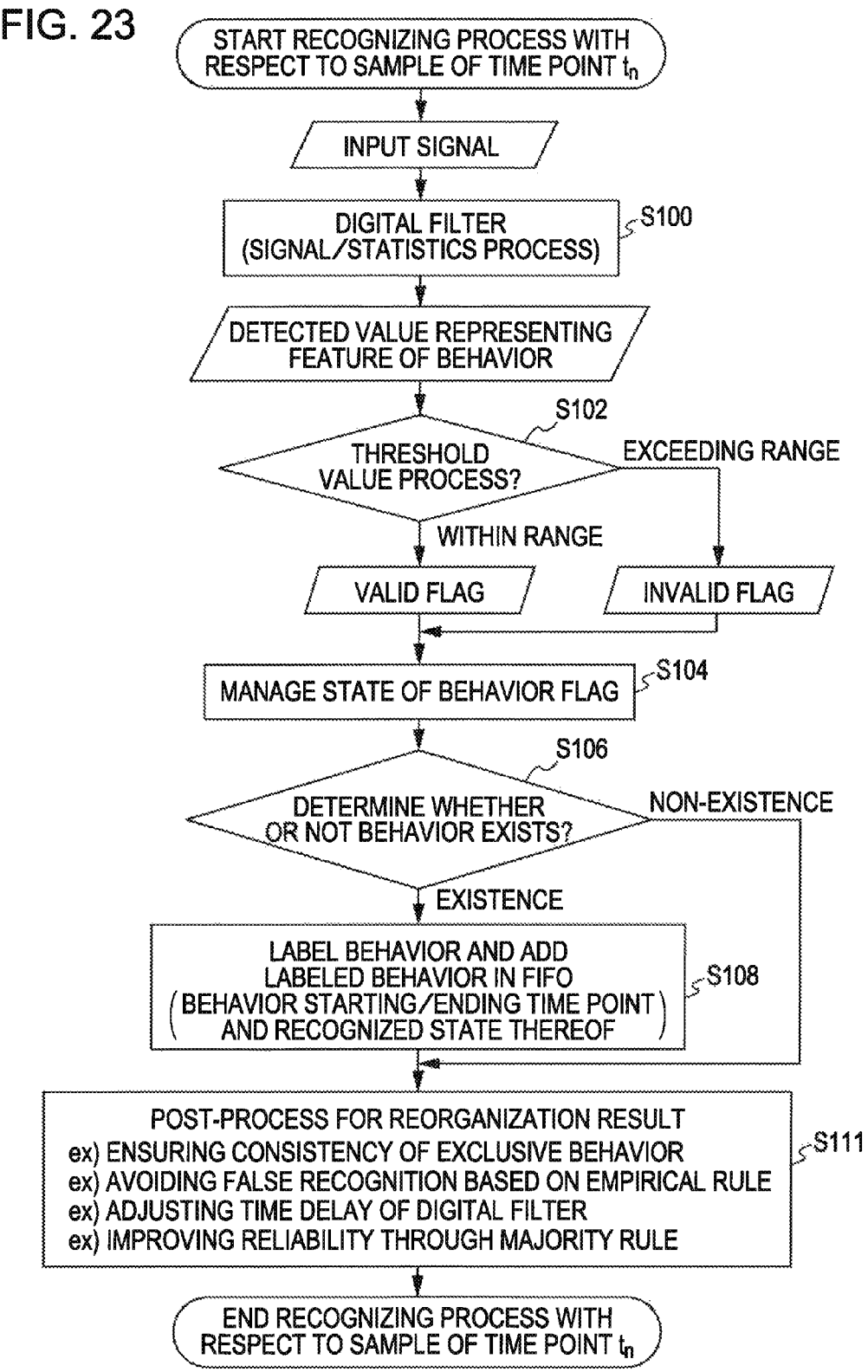
FIG. 23 is a diagram illustrating a flow of an information processing method in the modified example of the information processing apparatus according to the embodiment of the invention.

Next, a modified example of the first embodiment of the invention will be described with reference to FIGS. 21 to 23. In addition, the overview of the information processing method in the information processing apparatus 101 is substantially the same as the overview of the information processing method in the information processing apparatus 100 described with reference to FIGS. 4 to 8, and thus, the description thereof will be omitted.

First, a functional configuration of the information processing apparatus 101 according to the modified example will be described with reference to FIG. 21. FIG. 21 is a diagram illustrating an example of the functional configuration of the information processing apparatus 101 according to the modified example.

The information processing apparatus 101 includes a sensor data generator 110, a behavior recognizing unit 112, a behavior manager 114, a behavior information post-processing unit 117, a data controller 150, a storage unit 152, a display controller 154, and a display screen 160. The behavior determination unit 118 includes a stopped state determination unit 122, a walking/running state determination unit 124, a jumping state determination unit 126, a posture change determination unit 128, an elevator boarding determination unit 130, an electric train boarding determination unit 132, and a turning-to-the-right/turning-to-the-left determination unit 134. The sensor data processing unit 120 includes a sensor data calculation unit 136, a specific area remover 138, a lower area remover 140, and a sensor data storage unit 142. The behavior information post-processing unit 117 includes an exclusive behavior information re-processing unit 144, a false recognition behavior information re-processing unit 146, a behavior information real-time adjusting unit 148, and a behavior comparison re-processing unit 149.

The sensor data generator 110, the behavior recognizing unit 112, and the behavior manager 114 in the information processing apparatus 101 are substantially the same as the sensor data generator 110, the behavior recognizing unit 112, and the behavior manager 114 in the information processing apparatus 100 according to the first embodiment. In addition, the data controller 150, the storage unit 152, the display controller 154, and the display screen 160 are also substantially the same as the data controller 150, the storage unit 152, the display controller 154, and the display screen 160 in the information processing apparatus 100. In addition, the exclusive behavior information re-calculation unit 144, the false recognition behavior information re-calculation unit 146, and the behavior information real-time adjusting unit 148 are also substantially the same as the exclusive behavior information re-calculation unit 144, the false recognition behavior information re-calculation unit 146, and the behavior information real-time adjusting unit 148 in the information processing apparatus 100. Therefore, in the embodiment, the behavior comparison re-processing unit 149 of the behavior information post-processing unit 117 will be mainly described, and description of the same configuration as the first embodiment will be omitted.

The behavior information post-processing unit 117 performs a predetermined post-process on the behavior information input by the behavior manager 114. In the modified example, the behavior comparison re-processing unit 149 performs a portion of the post-process. With respect to the behaviors performed within a predetermined time, the behavior comparison re-processing unit 149 compares summed times of the behavior information corresponding to two or more predetermined behaviors that are determined to be similar to each other based on similar behavior information as to whether or not the behaviors are similar to each other. In addition, the behavior comparison re-processing unit 149 selects the behavior information having the longest summed time as the behavior information for the predetermined time. The similar behavior information is information indicating whether or not the behaviors are similar to each other and is stored, for example, in the sensor data storage unit 142 or other database.

The process of the behavior comparison re-processing unit 149 will be described in more detail with reference to examples shown in FIGS. 22A to 22C. FIGS. 22A to 22C are diagrams illustrating examples of the information processing method according to the modified example.

First, as shown in FIG. 22A, the case where the user is determined to board a car for a first half of the predetermined time and to board a bus for a second half of the predetermined time by the process of the behavior recognizing unit is described as an example. In the example, the predetermined time is set to 50 seconds. In this case, first, the behavior comparison re-processing unit 149 determines based on the similar behavior information whether or not the behavior of boarding the car and the behavior of boarding the bus are similar to each other and determines that the associated two behaviors are similar to each other. In the example shown in FIG. 22A, the time of boarding the car corresponds to three memories (15 seconds), and the time of boarding the bus corresponds to seven memories (35 seconds). In other words, since the time of boarding the bus is longer than the time of boarding the car, the behavior comparison re-processing unit 149 performs a process such that the user boards only the bus within the predetermined time.

Next, as shown in FIG. 22B, the case where the user is determined to board a car, a bus, a car, a bus, and a car for a predetermined time in this order by the process of the behavior recognizing unit is described as an example. In this case, first, the behavior comparison re-processing unit 149 determines based on the similar behavior information whether or not the behavior of boarding the car and the behavior of boarding the bus are similar to each other and determines that the associated two behaviors are similar to each other. In the example shown in FIG. 22B, the time of boarding the car corresponds to three memories (15 seconds) since there are three sites each of which corresponds to one memory, and the time of boarding the bus corresponds to seven memories (35 seconds) since there is one site which corresponds to three memories and one site which corresponds to four memories. In other words, since the summed time of boarding the bus is longer than the summed time of boarding the car, the behavior comparison re-processing unit 149 performs a process such that the user boards only the bus within the predetermined time.

Next, as shown in FIG. 22C, the case where the user is determined to board a car, an electric train, and a bus in this order by the process of the behavior recognizing unit is described as an example. In this manner, even in the case where the boarding of the three vehicles is recognized, first, the behavior comparison re-processing unit 149 determines based on the similar behavior information whether or not the behaviors of boarding the vehicles are similar to each other and determines that the associated three behaviors are similar to each other. In the example shown in FIG. 22C, the time of boarding the car corresponds to two memories (10 seconds); the time of boarding the electric train corresponds to six memories (30 seconds); and the time of boarding the bus corresponds to two memories (10 seconds). In other words, since the time of boarding the electric train is longest, the behavior comparison re-processing unit 149 performs a process such that the user boards only the electric train within the predetermined time.

The examples shown in FIGS. 22A to 22C are the cases where the user is determined to board a car or the like. Although the result of the behavior recognition by the vehicle boarding determination unit 532 according to a second embodiment described later is exemplified, the process of the behavior comparison re-processing unit 149 is not limited thereto. In other words, like behaviors of boarding a car, a bus, and an electric train, two or more behaviors that are determined to be similar to each other based on similar behavior information may be used.

In this manner, although it is actually difficult to assume that the user boards a plurality of vehicles such as a car, a bus, and an electric train for a short time of about 50 seconds, the behavior comparison re-processing unit 149 performs the aforementioned post-process, so that the result of the behavior recognition may reflect an actual user behavior with a better accuracy. In addition, the predetermined time is set to 50 seconds in the above example, but it is not limited thereto. In addition, the predetermined time may be set in advance or set by the user. In general, a time for boarding a vehicle such as a car, a bus, and an electric train is at least several minutes. In other words, the predetermined time is shorter than the actual time for boarding the vehicle. Therefore, since the time of performing the post-process in the behavior comparison re-processing unit 149 corresponds to a range of error in comparison with the actual time of the user's boarding of the vehicle, although the behavior comparison re-processing unit 149 performs the post-process as described above, the accuracy of the result of the behavior recognition may not deteriorate.

Next, a flow of the behavior recognition method and the behavior information post-processing method will be described with reference to FIG. 23. FIG. 23 is a diagram illustrating a flow of the behavior recognition method and the behavior information post-processing method according to the modified example. In the modified example, the processing method performed by the Steps S100, S102, S104, S106, and S108 is substantially the same as the behavior recognition method according to the first embodiment of the invention described with reference to FIG. 9 and the processing method performed by the Steps S100, S102, S104, S106, and S108 in the flow of the behavior information post-processing method. Therefore, in the modified example, the processing method performed by the Step S111 will be mainly described, and thus, description of the same processing method as that of the first embodiment will be omitted.

In Step S111, the behavior information post-processing unit 117 performs the post-process on the result of the behavior recognition obtained by the processes performed in Steps S100 to S108. As the post-process, there is, for example, a process of ensuring the consistency of the exclusive behavior, which is performed by the exclusive behavior information re-calculation unit 144 of the behavior information post-processing unit 116. In addition, there is a process of avoiding false recognition based on the empirical rule, which is performed by the false recognition behavior information re-calculation unit 146 of the behavior information post-processing unit 116. In addition, there is a process of adjusting the time delay of a digital filter, which is performed by the behavior information real-time adjusting unit 148 of the behavior information post-processing unit 116. There is a process of improving the reliability of the majority rule, which is performed by the behavior comparison re-processing unit 149 of the behavior information post-processing unit 116. The process of the majority rule denotes the process of comparing the predetermined evaluated values on the behavior information corresponding to two or more behaviors for the predetermined time and determining that the behavior corresponding to the behavior information having the large evaluated value is performed for the predetermined time as described with reference to FIGS. 22A to 22C. For example, the behavior comparison re-processing unit 149 calculates the summed times of the behaviors within a predetermined time with respect to the labeled result of the behavior recognition and treats the behavior having the longest time as the valid behavior and the other behaviors as invalid behaviors. Since the post-process of the behavior information post-processing unit 117 is described with reference to FIGS. 18 to 22C, the detailed description thereof is omitted. Due to the post-process, the reliability of the result of the behavior recognition calculated by the information processing apparatus 101 may be further improved.

7. Functional Configuration of Information Processing Apparatus 500 According to Second Embodiment of the Invention Next, a functional configuration of the information processing apparatus 500 according to a second embodiment of the invention will be described with reference to FIG. 24. FIG. 24 is a diagram illustrating an example of the functional configuration of the information processing apparatus 500 according to the second embodiment of the invention. The information processing apparatus 500 includes a characteristic vector calculation function for the sensor data depending on the user behavior, an identification function calculation function, and a threshold value determination function as one of the features.

The information processing apparatus 500 includes a sensor data generator 110, a behavior recognizing unit 512, a behavior manager 114, a behavior information post-processing unit 117, a data controller 150, a storage unit 152, a display controller 154, and a display screen 160. The behavior recognizing unit 512 includes a behavior determination unit 518 and a sensor data processing unit 520. The sensor data processing unit 520 includes a sensor data calculation unit 536 and a sensor data storage unit 142. The behavior information post-processing unit 117 includes an exclusive behavior information re-processing unit 144, a false recognition behavior information re-processing unit 146, a behavior information real-time adjusting unit 148, and a behavior comparison re-processing unit 149. The behavior determination unit 518 includes a stopped state determination unit 122, a walking/running state determination unit 124, a jumping state determination unit 126, a posture change determination unit 128, an elevator boarding determination unit 130, a vehicle boarding determination unit 532, and a turning-to-the-right/turning-to-the-left determination unit 134. The sensor data processing unit 120 includes a sensor data calculation unit 536, a specific area remover 138, a lower area remover 140, and a sensor data storage unit 142.

The sensor data generator 110, the behavior manager 114, and the data controller 150 in the information processing apparatus 500 are substantially the same as the sensor data generator 110, the behavior manager 114, and the data controller 150 in the information processing apparatus 100 according to the first embodiment. In addition, the behavior information post-processing unit 117 is substantially the same as the behavior information post-processing unit 117 in the information processing apparatus 101 according to the modified example of the first embodiment. In addition, the storage unit 152, the display controller 154, and the display screen 160 are also substantially the same as the storage unit 152, the display controller 154, and the display screen 160 in the information processing apparatus 100 according to the first embodiment. In addition, the stopped state determination unit 122 and the walking/running state determination unit 124 are also substantially the same as the stopped state determination unit 122 and the walking/running state determination unit 124 in the information processing apparatus 100. In addition, the jumping state determination unit 126 and the posture change determination unit 128 are also substantially the same as the jumping state determination unit 126 and the posture change determination unit 128 in the information processing apparatus 100. In addition, the elevator boarding determination unit 130 and the turning-to-the-right/turning-to-the-left determination unit 134 are also substantially the same as the elevator boarding determination unit 130 and the turning-to-the-right/turning-to-the-left determination unit 134 in the information processing apparatus 100 according to the first embodiment. Therefore, in the embodiment, the vehicle boarding determination unit 518 of the behavior recognizing unit 512 and the sensor data calculation unit 536 of the sensor data processing unit 520 will be mainly described, and thus, description of the same configuration as that of the first embodiment and the modified example will be omitted.

The behavior recognizing unit 512 acquires the sensor data from the sensor data generator 110. The behavior recognizing unit 512 recognizes the behavior exhibited by the user by performing a predetermined threshold value process on the sensor data and generates the behavior information that is the information indicating the behavior exhibited by the user. The behavior recognizing unit 512 includes a sensor data processing unit 520 having a sensor data calculation unit 536. The sensor data calculation unit 536 calculates the characteristic vector based on the acceleration sensor data that is an example of the sensor data. Next, the sensor data calculation unit 536 substitutes the characteristic vector for the identification function set for each type of the vehicle to calculate the value of the identification function. The behavior recognizing unit 512 further includes a vehicle boarding determination unit 518 that determines whether or not the user boards a predetermined vehicle and generates the behavior information based on the determination result of the vehicle boarding determination unit 518. The vehicle boarding determination unit 518 determines whether or not the value of the identification function calculated by the sensor data calculation unit 536 is larger than the vehicle boarding recognition value that is used to recognize whether the user boards the vehicle corresponding to the identification function.

The characteristic vector includes, for example, physical properties necessary to represent the boarding of the vehicle, such as an average value, a variance value, and a frequency in the vertical or horizontal direction generated from the sensor data. The identification function is set in advance according to each vehicle based on data of a number having statistical meaning with a reference to a general mechanical learning mechanism. The data is an actually-measured characteristic vector at the time of boarding a defined vehicle. In addition, the identification function is stored in the sensor data storage unit 142 in advance, but it may be updated by the user's input. The vehicle is not limited thereto, but, for example, may be adapted to an electric train, a car, a bus, and a bicycle.

In this manner, in the information processing apparatus 500, since the identification function according to the vehicle is set in the sensor data storage unit 142, the identification function may be simply and easily designed in the design of the digital filter. Therefore, there is no problem that the apparatus has to have a large size, and types of the vehicles to be determined may be increased. For example, as listed in the following Table 2, it may be easily determined based on the acceleration sensor whether or not the user boards a plurality of vehicles marked by asterisk. In addition, since the vehicle boarding determination unit 532 determines based on the identification function specified to each vehicle whether or not the vehicle is boarded, although the change in the acceleration of the vehicle that the user boards is not large, it may be determined with a better accuracy whether or not each vehicle is boarded. In addition, since the method of calculating the characteristic vector is common to the vehicles and only the settings of the identification functions are different among the vehicles, it may be determined by a much simpler method whether or not the user boards the vehicles. In addition, since the identification function that is set in advance may be learned and updated later by the user, the identification function may be updated according to the change in motion of the vehicle involved in the change of the times. In addition, since the behavior information post-processing unit 116 of the behavior comparison re-processing unit 149 or the like performs the post-process, there is no problem in that the result of the behavior recognition of exchanging a plurality of the vehicles any number of times for a short time of about tens of seconds is generated, and the result of the behavior recognition may be obtained with a better accuracy.

TABLE 2

| Type of Behavior | Type or Sensor |
| --- | --- |
| Stop | Only Acceleration Sensor |
| Temporarily Stop | Only Acceleration Sensor |
| Walk | Only Acceleration Sensor |
| Run | Only Acceleration Sensor |
| Jump | Only Acceleration Sensor |
| Sit | Only Acceleration Sensor |
| Stand | Only Acceleration Sensor |
| Rise in Elevator | Only Acceleration Sensor |
| Descend in Elevator | Only Acceleration Sensor |

TABLE 2-continued

| Type of Behavior | Type or Sensor |
| --- | --- |
| * Board Electric Train | Only Acceleration Sensor |
| * Board Bus | Only Acceleration Sensor |
| * Board Car | Only Acceleration Sensor |
| * Board Bicycle | Only Acceleration Sensor |
| Turn to the Right | Acceleration Sensor and Gyro Sensor |
| Turn to the Left | Acceleration Sensor and Gyro Sensor |

8. Application Examples of Information Processing Method in Information Processing Apparatus 500

Figure 25:
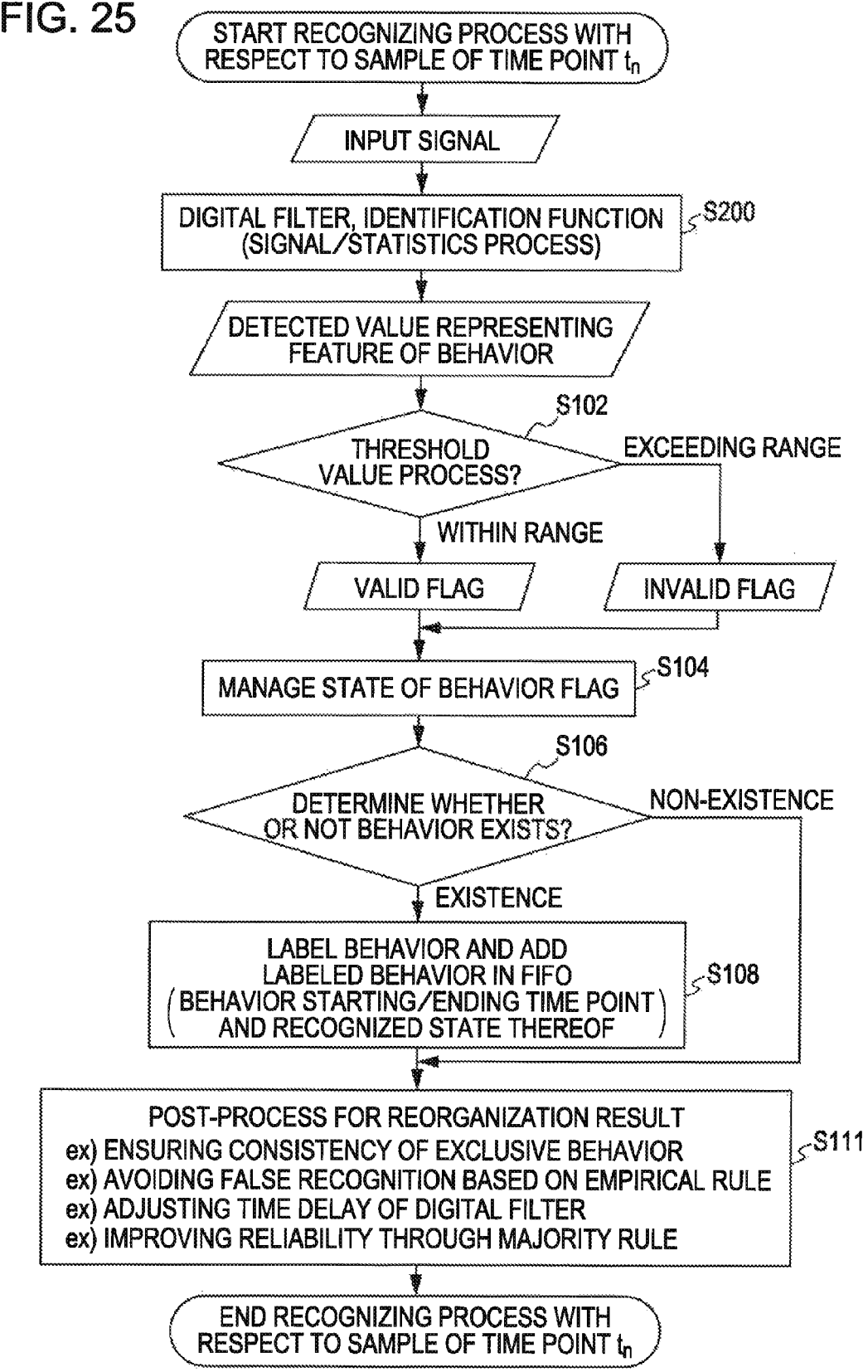
FIG. 25 is a diagram illustrating a flow of an information processing method in the information processing apparatus according to the embodiment of the invention.
Figure 26:
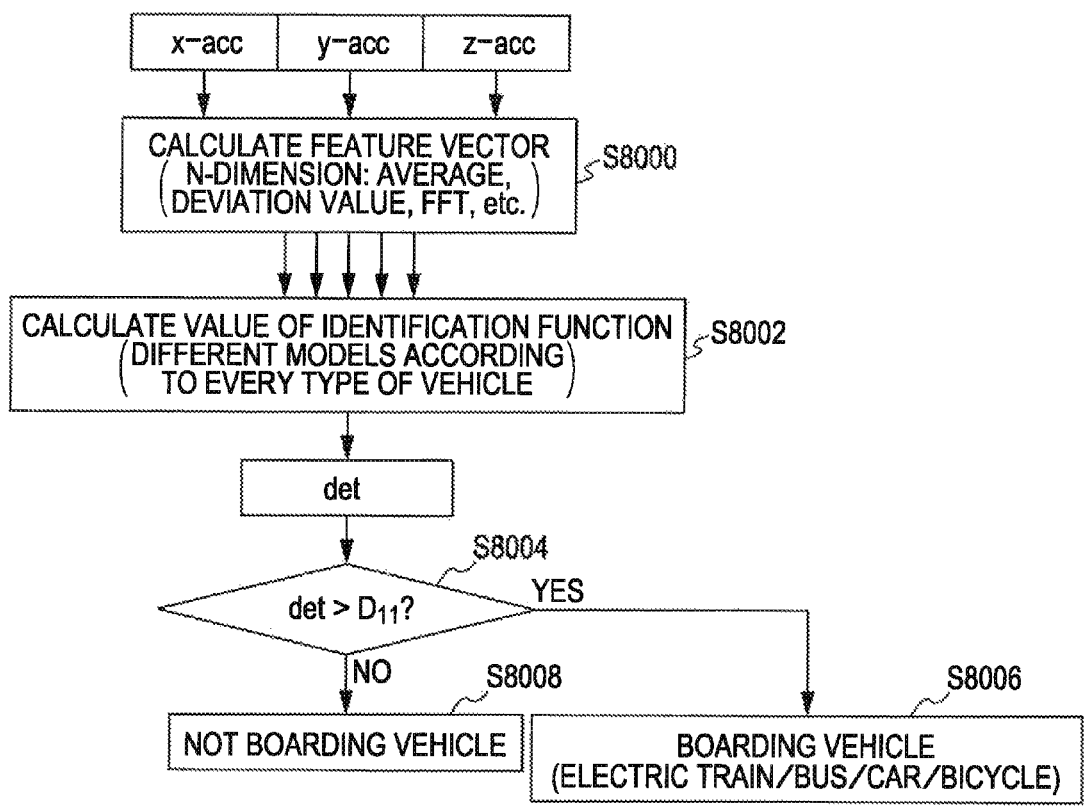
FIG. 26 is a diagram illustrating a flow of a method of recognizing boarding a vehicle in the information processing apparatus according to the embodiment of the invention.

Next, application examples of the information processing method will be described with reference to FIGS. 25 and 26. In addition, the overview of the information processing method in the information processing apparatus 500 is substantially the same as the overview of the information processing method in the information processing apparatus 100, and thus, the description thereof will be omitted.

8-1. Behavior Recognition Function and Behavior Information Post-Process Function FIG. 25 is a diagram illustrating a flow of an information processing method in the information processing apparatus 500. The processing methods performed by the steps S102, S104, S106, and S108 of FIG. 25 are substantially the same as the processing methods performed by the steps S102, S104, S106, and S108 described with reference to FIG. 9. In addition, the processing method performed by the step S111 is substantially the same as the processing method performed by the step S111 described with reference to FIG. 23. Therefore, herein, description will be made of the processing method performed by the step S200, and the description of processes described with reference to FIGS. 9 and 23 will be omitted. In addition, since the same function as the function of acquiring the recognition result of the past time point $t_{n-d}$ described with reference to FIG. 10 is also performed in this embodiment, the description thereof will be omitted.

In Step S200, the behavior recognizing unit 512 calculates a characteristic vector corresponding to the sensor data generated by the sensor data generator 110 as an input signal and outputs the value of the identification function by using the identification function set according to the type of vehicle. Hereinafter, the process performed by the Step S200 will be described in detail with reference to FIG. 26.

8-2. Method of Recognizing Whether or not the User Boards Vehicle

Next, a method of recognizing whether or not a user boards a vehicle will be described with reference to FIG. 26. FIG. 26 is a diagram illustrating a flow of a method of recognizing whether or not a user boards a vehicle by the behavior recognizing unit 512.

First, the sensor data generator 110 senses the user behavior 156 and generates sensor data. Next, the behavior recognizing unit 512 acquires the sensor data from the sensor data generator 110. In order to recognize whether or not a user boards a vehicle, first, the vehicle boarding determination unit 518 transmits to the sensor data processing unit 520 a signal for recognizing whether or not a vehicle is boarded. In addition, the sensor data processing unit 520 acquires the sensor data from the sensor data generator 110.

The sensor data calculation unit 536 calculates characteristic vectors for the x-acc, the y-acc, and the z-acc (S8000). The characteristic vector includes, for example, a plurality of characteristic amounts such as an average value, a variance value, and a frequency in the horizontal or vertical direction, which are derived from the sensor data. The characteristic vector may be calculated by the same method irrespective of the type of vehicle that the user boards.

Next, the sensor data calculation unit 536 substitutes the characteristic vector for the identification function acquired from the sensor data storage unit 142 to output a value of the identification function (S8002). Herein, the predetermined identification function is a non-linear or linear function set according to the type of vehicle. The identification function may be stored in the sensor data storage unit 142 in advance or updated according to the user input. In addition, the vehicle includes, for example, an electric train, a car, a bus, and a bicycle.

Next, the vehicle boarding determination unit 518 determines that the user boards the vehicle corresponding to the identification function and determines whether or not the output value of the identification function is larger than the vehicle boarding recognition value $D_{11}$ for recognizing that the user boards the vehicle (S8004). The vehicle boarding recognition value $D_{11}$ may be different according to the type of vehicle.

Next, in the case where the value of the identification function is larger than the vehicle boarding recognition value $D_{11}$, the vehicle boarding determination unit 518 generates the behavior information indicating that the user boards the predetermined vehicle (S8006). For example, in the case where the process is to determine whether or not the user boards an electric train, the vehicle boarding determination unit 518 generates the behavior information indicating that the user boards the electric train. In addition, for example, in the case where the process is to determine whether or not the user boards a bus, the vehicle boarding determination unit 518 generates the behavior information indicating that the user boards the bus. In addition, for example, in the case where the process is to determine whether or not the user boards a car, the vehicle boarding determination unit 518 generates the behavior information indicating that the user boards the car. In addition, for example, in the case where the process is to determine whether or not the user boards a bicycle, the vehicle boarding determination unit 518 generates the behavior information indicating that the user boards the bicycle.

The determination whether or not the user boards the vehicles may be simultaneously performed. Accordingly, the result of behavior recognition indicating that the user boards a car or a bus may be obtained in a short time, for example, in about 50 seconds. However, in this case, for example, as described with reference to FIGS. 21 to 23, the behavior comparison re-processing unit 149 performs a re-process indicating that the user boards only the vehicle which is determined to be boarded for a longer time, among the car and the bus, for the time. Whether or not the behavior comparison re-processing unit 149 is to perform the post-process may be set by the information processing apparatus 500 in advance or input by user manipulation.

On the other hand, in the case where the value of the identification function is equal to or smaller than the vehicle boarding recognition value $D_{11}$, the vehicle boarding determination unit 518 generates the behavior information indicating that the user does not board the predetermined vehicle (S8008). For example, in the case where the process is to determine whether or not the user boards an electric train, the vehicle boarding determination unit 518 generates the behavior information indicating that the user does not boards the electric train. In addition, for example, in the case where the process is to determine whether or not the user boards a bus, the vehicle boarding determination unit 518 generates the behavior information indicating that the user does not board the bus. In addition, for example, in the case where process is to determine whether or not the user boards a car, the vehicle boarding determination unit 518 generates the behavior information indicating that the user does not board the car. In addition, for example, in the case where process is to determine whether or not the user boards a bicycle, the vehicle boarding determination unit 518 generates the behavior information indicating that the user does not board the bicycle.

9. Example of Hardware Configuration of Information Processing Apparatuses 100 and 500

Figure 21:
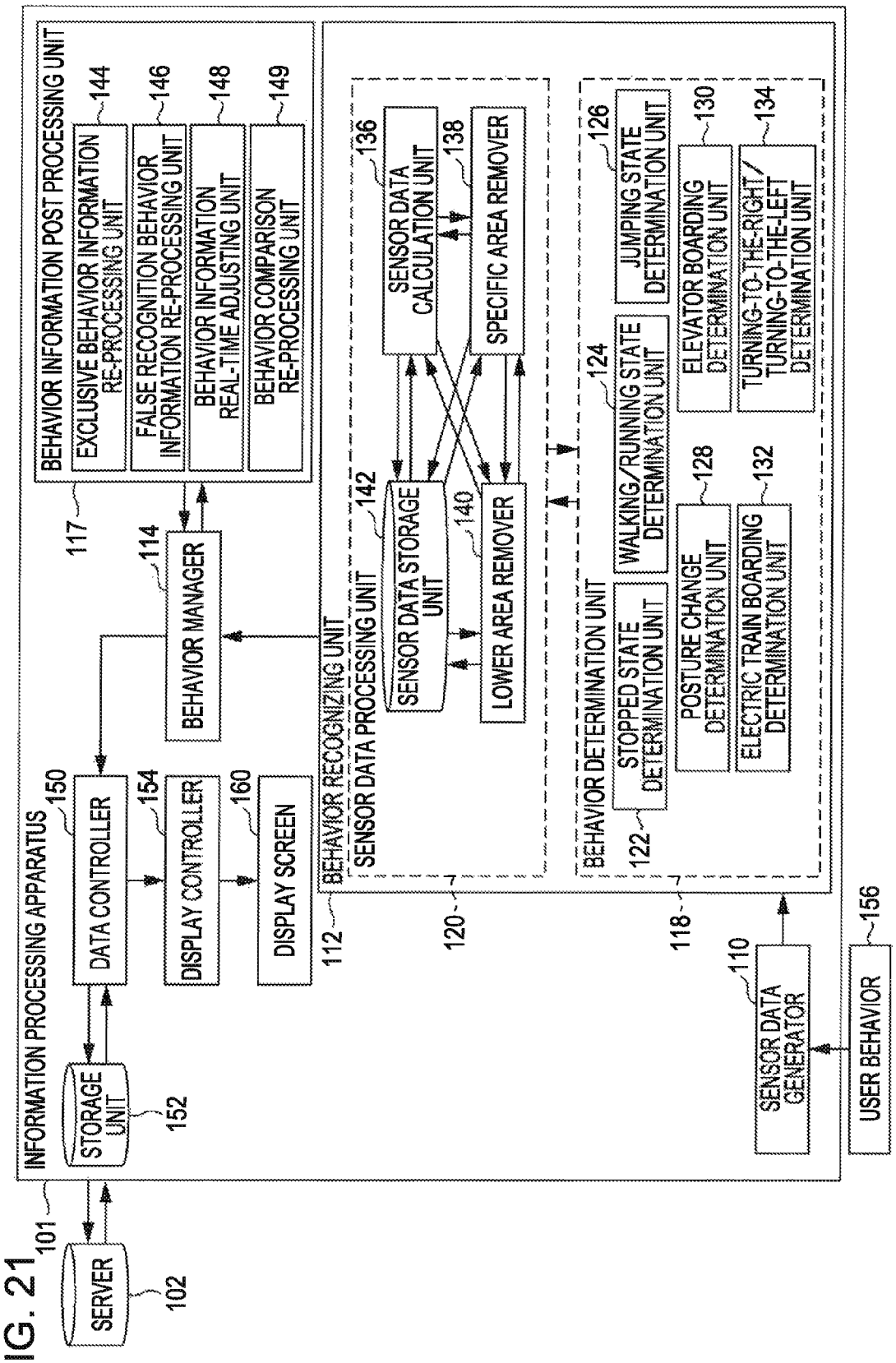
FIG. 21 is a diagram illustrating a functional configuration of a modified example of the information processing apparatus according to the embodiment of the invention.

The functions of the components of the apparatus may be implemented, for example, by a computer program for implementing the functions in the information processing apparatus having a hardware configuration shown in FIG. 21. FIG. 21 is a diagram illustrating the hardware configuration of the information processing apparatus capable of implementing the functions of the components of the apparatus. The information processing apparatus has an arbitrary form. For example, a portable information terminal such as a personal computer, a mobile phone, a PHS (Personal Handy-phone System), and a PDA (Personal Digital Assistant), a game machine, or various information electronic appliances are included in the form.

As shown in FIG. 21, the information processing apparatus mainly includes a CPU (Central Processing Unit) 902 and a ROM (Read Only Memory) 904. In addition, the information processing apparatus also includes a RAM (Random Access Memory) 906, a host bus 908, a bridge 910, an external bus 912, and an interface 914. In addition, the information processing apparatus further includes an input unit 916, an output unit 918, a storage unit 920, a drive 922, a connection port 924, and a communication unit 926.

The CPU 902 functions as, for example, a calculation processing apparatus or a control apparatus to control the ROM 904, the RAM 906, the storage unit 920, or the entire operations of the components or a portion thereof based on various types of programs recorded in a removable recording medium 928. The ROM 904 stores, for example, programs read by the CPU 902 or data used for calculation. The RAM 906 temporarily or permanently stores, for example, programs read by the CPU 902 or various parameters that are suitably changed at the time of executing the programs. The components are connected to each other, for example, via a host bus 908 capable of implementing high-rate data transmission. In addition, the host bus 908 is connected to an external bus 912, of which data transmission rate is relatively low, for example, through a bridge 910.

The input unit 916 is, for example, a manipulator such as a mouse, a keyboard, a touch panel, a button, a switch, and a lever. In addition, the input unit 916 may be a remote controller (so-called "remocon") capable of transmitting a control signal by using an infrared ray or other electromagnetic waves. In addition, the input unit 916 is configured to have an input control circuit for transmitting information input by using the manipulator as an input signal to the CPU 902.

The output unit 918 is, for example, a display apparatus such as a CRT (Cathode Ray Tube) and an LCD (Liquid Crystal Display). In addition, the output unit 918 may be a display apparatus such as a PDP (Plasma Display Panel) and an ELD (Electro-Luminescence Display). In addition, the output unit 918 may be an apparatus capable of visually or auditorily notifying the acquired information to the user such as an audio output apparatus including a speaker and a headphone, a printer, a mobile phone, and a facsimile.

The storage unit 920 is constructed with an apparatus for storing various types of data, for example, a magnetic storage device such as a hard disk drive (HDD), a semiconductor storage device, an optical storage device, or an opto-magnetic storage device.

The drive 922 is an apparatus for reading information recorded in, for example, a removable recording medium 928 such as a magnetic disk, an optical disk, an opto-magnetic disk, or a semiconductor memory or writing information in the removable recording medium 928. The removable recording medium 928 is, for example, a DVD media, a Blu-ray media, an HD DVD media, a memory stick, or an SD memory card (Secure Digital memory card). The removable recording medium 928 may be, for example, an IC card (Integrated Circuit Card) embedded with a non-contact IC chip or an electronic apparatus.

The connection port 924 is, for example, a port for connecting an external connection apparatus 930 such as a USB (Universal Serial Bus) port and an IEEE1394 port. In addition, the connection port 924 is, for example, a port for connecting the external connection apparatus 930 such as a SCSI (Small Computer System Interface), an RS-232C port, or an optical audio port. The external connection apparatus 930 is, for example, a printer, a portable music player, a digital camera, a digital video camera, or an IC recorder.

The communication unit 926 is a communication device for connecting to the network 932 and is, for example, a wired or wireless LAN (Local Area Network or a WUSB (Wireless USB) communication card. In addition, the communication unit 926 is an optical communication router, an ADSL (Asymmetric Digital Subscriber Line) router, or various communication modems. In addition, the network 932 connected to the communication unit 926 is configured to a network connected in a wired or wireless manner and is, for example, the Internet, an indoor LAN, an infrared communication, a visible communication, a broadcast, or a satellite broadcast.

10. Statistics

Finally, the functional configurations of the information processing apparatuses according to the embodiments and the effects obtained from the functional configurations will be described in brief.

First, the functional configurations of the information processing apparatus according to the embodiment may be expressed as follows. The information processing apparatus includes a sensor data generator, a behavior recognizing unit, a behavior manager, and a behavior information post-processing unit. The sensor data generator senses the user behavior to generate the sensor data corresponding to the user behavior. The behavior recognizing unit recognizes the behavior exhibited by the user by performing a predetermined threshold value process on the sensor data and generates the behavior information that is the information indicating the behavior exhibited by the user. The behavior manager manages the behavior information generated by the behavior recognizing unit in correspondence with the time point at which the behavior corresponding to the behavior information is exhibited. The behavior information post-processing unit performs a predetermined post-process on the behavior information managed by the behavior manager. The behavior recognizing unit further includes a plurality of behavior determination units specified to specific behaviors exhibited by the user and generates the behavior information based on the determination results of the plurality of behavior determination units. In this manner, since the plurality of behavior determination units specified to specific behaviors exhibited by the user are included and the behavior determination units generate the behavior information, the behaviors may be recognized with good accuracy, so that false recognition may be reduced.

In addition, the functions of the information processing apparatus according to the embodiment may be expressed as follows. The behavior recognizing unit includes a stopped state determination unit, a walking/running state determination unit, a jumping state determination unit, a posture change determination unit, an elevator boarding determination unit, an electric train boarding determination unit, and a turning-to-the-right/turning-to-the-left determination unit. The stopped state determination unit determines whether or not the user is in the stopped state. The walking/running state determination unit determines whether the user is in the walking state or in the running state. The jumping state determination unit determines whether or not the user is in the jumping state or in the non-jumping state. The posture change determination unit determines whether or not the user is in the sitting state or in the standing state. The elevator boarding determination unit determines whether or not the user is in the boarding-elevator state. The electric train boarding determination unit determines whether or not the user is in the boarding-electric train state. The turning-to-the-right/turning-to-the-left determination unit determines whether or not the user turns to the right or the left. In this manner, since the plurality of behavior determination units specified to specific behaviors exhibited by the user are included and the behavior determination units generate the behavior information, the behaviors may be recognized with a good accuracy, so that false recognition may be reduced.

In addition, the functions of the information processing apparatus according to the embodiment may be expressed as follows. In the information processing apparatus, the behavior recognizing unit includes as the behavior determination unit a vehicle boarding determination unit that determines whether or not the user boards the vehicle by using the sensor data and a predetermined identification function set in advance. In this manner, in design of a digital filter, since an identification function that can be easily designed is set, there is no problem that the apparatus has to have a large size, and the types of vehicles to be determined may be increased. In addition, since the vehicle boarding determination unit determines based on the identification function specified to each vehicle whether or not the vehicle is boarded, although the change in the acceleration of the vehicle that the user boards is not large, the vehicle boarding determination unit may determine with a better accuracy whether or not each vehicle is boarded.

In addition, the functions of the information processing apparatus according to the embodiment may be expressed as follows. The sensor data storage unit records the sensor data in the FIFO manner. The sensor data calculation unit performs a predetermined calculation by using the sensor data. The specific area remover removes a value excluding a specific area from the input data. The lower area remover removes a range smaller than a predetermined threshold value from the input data. Each of the behavior determination units determines the behavior exhibited by the user based on the calculation result output from the sensor data processing unit. In this manner, the plurality of behavior determination units specified to specific behaviors exhibited by the user are included, and the behavior determination units allow the sensor data processing unit to perform predetermined calculations corresponding to the behaviors. Therefore, the behaviors may be recognized with a good accuracy, so that false recognition may be reduced.

In addition, the functions of the information processing apparatus according to the embodiment may be expressed as follows. The behavior information post-processing unit further includes an exclusive behavior information re-processing unit that detects whether or not an exclusive characteristic representing that the user exhibits exclusive behaviors that are difficult to simultaneously perform exists in the behavior information. In the case where two or more behaviors have the exclusive characteristic, the exclusive behavior information re-processing unit excludes the behavior information corresponding to at least one behavior among the two or more behaviors. In this manner, since the behavior information having the exclusive characteristic is excluded from the behavior information that is subject to the process performed by the behavior recognizing unit, the behavior information of the user is generated with a good accuracy, so that false recognition is reduced.

In addition, the functions of the information processing apparatus according to the embodiment may be expressed as follows. The behavior information post-processing unit includes a false recognition behavior information re-processing unit that re-processes the behavior information every unit time based on a behavior information necessary condition necessary for the user to exhibit each behavior. In the case where the behavior information does not satisfy the behavior information necessary condition, the false recognition behavior information re-processing unit corrects the behavior information corresponding to the behavior. In this manner, since the behavior information having no behavior information necessary condition is excluded from the behavior information that is subject to the process performed by the behavior recognizing unit, the behavior information of the user is generated with a good accuracy, so that false recognition is reduced.

In addition, the functions of the information processing apparatus according to the embodiment may be expressed as follows. The behavior information post-processing unit includes a behavior information real-time adjusting unit that determines that the user exhibits each behavior at the time point that is earlier than the time point at which the behavior recognizing unit transmits the behavior information to the behavior manager by the time necessary for the behavior recognizing unit to generate the behavior information corresponding to each behavior. In this manner, with respect to the behavior information after the process performed by the behavior recognizing unit, since a time necessary for the behavior recognition process is corrected, the time point at which the user behavior is exhibited may be recognized with good accuracy.

In addition, the functions of the information processing apparatus according to the embodiment may be expressed as follows. In the information processing apparatus, the behavior information post-processing unit includes a behavior comparison re-processing unit. In the case where two or more behaviors performed within a predetermined time are similar to each other, the behavior comparison re-processing unit includes a behavior comparison re-processing unit that compares summed times of the behavior information corresponding to the two or more behaviors. In addition, the behavior comparison re-processing unit selects the behavior information having the longest summed time as the behavior information for the predetermined time. In the case where the predetermined time is, for example, a shot time of about tens of seconds, in practice it is difficult to consider that the user boards a plurality of the vehicles. However, in this manner, the behavior comparison re-processing unit performs the post-process, so that the result of the behavior recognition may reflect the actual user behavior with a better accuracy.

In addition, the functions of the information processing apparatus according to the embodiment may be expressed as follows. The sensor data include first to third acceleration sensor data that are data associated with accelerations according to the predetermined coordinate axes. First, the sensor data calculation unit calculates variance values of the first acceleration sensor data, the second acceleration sensor data, and the third acceleration sensor data in the first predetermined time range, which are recorded in the sensor data storage unit. Next, the behavior determination unit determines whether or not the maximum variance value that is the largest variance value is smaller than the stop recognition value for recognizing that the user stops. In addition, the behavior determination unit determines whether or not the time, in which the maximum variance value is smaller than the stop recognition value, continues to be longer than the stop recognition time for recognizing that the user stops. In this case, the behavior determination unit generates the behavior information indicating that the user stops. In addition, the behavior determination unit determines whether or not the maximum variance value is smaller than the stop recognition value. In addition, the behavior determination unit determines whether or not the time, in which the maximum variance value is smaller than the stop recognition value, continues to be longer than the stop recognition time. In this case, the behavior determination unit generates the behavior information indicating that the user temporarily stops. In this manner, since the stopped state determination unit allows the sensor data processing unit to perform a unique process specified to the behavior, it may be recognized with a good accuracy whether the user stops or temporarily stops.

In addition, the functions of the information processing apparatus according to the embodiment may be expressed as follows. The sensor data calculation unit calculates variance values of the first acceleration sensor data, the second acceleration sensor data, and the third acceleration sensor data in the second predetermined time range, which are recorded in the sensor data storage unit. Next, the sensor data calculation unit calculates the maximum variance value among the variance values. Next, the specific area remover removes a frequency in a range excluding the walking/running recognition frequency area, in which the user is recognized as walking or running. Next, the autocorrelation function of the acceleration sensor data recorded in the sensor data storage unit is calculated, so that the maximum value of the autocorrelation function is calculated. As a result, the sensor data calculation unit also calculates the walking/running frequency data at the time when the user walks or runs.

Next, the sensor data calculation unit multiplies the walking/running frequency data with the maximum variance value. Next, the lower area remover removes a frequency area, in which the user may be falsely recognized as walking or running, from the walking/running frequency data that are subject to the predetermined calculation and the maximum variance value. In this manner, the noise of the behavior information generated later is reduced by the process of the lower area remover, so that the behavior may be recognized with a better accuracy. Next, as a result, the walking/running determination data for determining that the user walks or runs are calculated. Next, the walking/running state determination unit determines whether or not the value of the walking/running determination data is larger than the minimum walking recognition value that is a lower limit value for recognizing that the user walks. In addition, the walking/running state determination unit determines whether or not the value of the walking/running determination data is smaller than the maximum walking recognition value that is an upper limit value for recognizing that the user walks. In this case, the walking/running state determination unit generates the behavior information indicating that the user walks. In addition, in the case where the value of the walking/running determination data is larger than the maximum walking recognition value, the walking/running state determination unit generates the behavior information indicating that the user runs. In this manner, since the walking/running state determination unit allows the sensor data processing unit to perform a unique process specified to the behavior, it may be recognized with a good accuracy whether the user walks or runs. In addition, the sensor data calculation unit integrates the walking/running frequency data, and the walking/running state determination unit may generate the behavior information regarding the number of steps of the user from the result of the integration.

In addition, the functions of the information processing apparatus according to the embodiment may be expressed as follows. First, the sensor data calculation unit calculates the jumping acceleration represented by the magnitudes of the first acceleration sensor data, the second acceleration sensor data, and the third acceleration sensor data to recognize the user's jumping. Next, the specific area remover removes a range excluding a jumping recognition area, in which the user is recognized to jump, from the jumping acceleration and calculates the corrected jumping acceleration. In this manner, the noise of the behavior information generated later is reduced by the process of the specific area remover, so that the behavior may be recognized with a better accuracy. Next, the lower area remover removes an area, in which the user may be falsely recognized as jumping, from the corrected jumping acceleration and calculates the jumping state determination value for determining whether or not to jump. In this manner, the noise of the behavior information generated later is reduced by the process of the lower area remover, so that the behavior may be recognized with a better accuracy. Next, the jumping state determination unit determines whether or not the jumping state determination value is larger than the minimum jumping recognition value that is a lower limit value for recognizing that the user jumps. In this case, the jumping state determination unit generates the behavior information indicating that the user jumps. In this manner, since the jumping state determination unit allows the sensor data processing unit to perform a unique process specified to the behavior, it may be recognized with a good accuracy whether the user jumps.

In addition, the functions of the information processing apparatus according to the embodiment may be expressed as follows. First, the lower area remover removes an area, in which the user may be falsely recognized to change posture, from the first acceleration sensor data, the second acceleration sensor data, and the third acceleration sensor data. In this manner, the noise of the behavior information generated later is reduced by the process of the lower area remover, so that the behavior may be recognized with a better accuracy. Next, as a result, the first gravity data based on the first acceleration sensor data, the second gravity data based on the second acceleration sensor data, and the third gravity data based on the third acceleration sensor data capable of determining whether or not there is a change in posture are calculated. The sensor data calculation unit calculates the posture change determination value for allowing the change in the user's posture to be recognized based on the result.

Next, the lower area remover removes an area, in which the user may be falsely recognized as changing posture, from the posture change determination value and calculates the corrected posture change determination value for determining whether or not the posture is changed. In this manner, the noise of the behavior information generated later is reduced by the process of the lower area remover, so that the behavior may be recognized with a better accuracy. Next, the posture change determination unit determines whether or not the corrected posture change determination value is larger than the minimum posture change recognition value that is a lower limit value for recognizing that the user changes the posture. In addition, in the case where the user is already standing, the posture change determination unit generates the behavior information indicating that the user sits. On the other hand, the posture change determination unit also determines whether or not the corrected posture change determination value is larger than the minimum posture change recognition value. In addition, in the case where the user is already sitting, the posture change determination unit generates the behavior information indicating that the user stands. In this manner, since the posture change determination unit allows the sensor data processing unit to perform a unique process specified to the behavior, it may be recognized with a good accuracy whether the user sits or stands.

In addition, the functions of the information processing apparatus according to the embodiment may be expressed as follows. First, the lower area remover removes an area, in which the acceleration in the gravity direction of the first acceleration sensor data, the second acceleration sensor data, and the third acceleration sensor data may be falsely recognized. In this manner, the noise of the behavior information generated later is reduced by the process of the lower area remover, so that the behavior may be recognized with a better accuracy. The sensor data calculation unit calculates the gravity direction acceleration sensor data based on the first acceleration sensor data, the second acceleration sensor data, and the third acceleration sensor data, from which the area is removed. The sensor data calculation unit calculates the gravity adjusting data represented by the magnitudes of the first acceleration sensor data, the second acceleration sensor data, and the third acceleration sensor data of allowing the value of the gravity to be adjusted. Next, the sensor data calculation unit records the gravity adjusting data in the sensor data storage unit. Next, the sensor data calculation unit calculates the gravity adjusting variance value that is the variance value of the gravity adjusting data and the gravity adjusting average data that are the average value of the gravity adjusting data that are recorded in the sensor data storage unit. The sensor data calculation unit determines whether or not the gravity adjusting variance value is smaller than the maximum allowable gravity adjusting variance value that is the maximum variance value for allowing the gravity adjusting. In addition, the sensor data calculation unit determines whether or not the gravity adjusting average data is larger than the minimum allowable gravity average value that is the minimum average value for allowing the gravity adjusting and whether or not the gravity adjusting average data is smaller than the maximum allowable gravity average value that is the maximum average value for allowing the gravity adjusting. In this case, the sensor data calculation unit considers the value according to the gravity adjusting average data to be the gravity after the adjusting. In this manner, since the gravity is adjusted, the problem of the change in the gravity that occurs in the case where the user carries the information processing apparatus in a slanted state thereof may not easily occur, so that erroneous behavior information may not be easily generated.

Next, the lower area remover removes an area, in which the gravity may be falsely recognized, from the gravity adjusting average data and calculates the corrected gravity adjusting average data. In this manner, the noise of the behavior information generated later is reduced by the process of the lower area remover, so that the behavior may be recognized with a better accuracy. Next, the sensor data calculation unit calculates a difference between the gravity direction acceleration sensor data and the corrected gravity adjusting average data. Next, the lower area remover removes an area, in which the user may be falsely recognized as boarding the elevator, from the difference. In this manner, the noise of the behavior information generated later is reduced by the process of the lower area remover, so that the behavior may be recognized with a better accuracy. Next, as a result, the lower area remover calculates the elevator rising determination data for determining whether or not the user boards the elevator. The elevator boarding determination unit determines whether or not the elevator rising determination data is larger than the predetermined value $D_\alpha$ at first and smaller than the predetermined value $D_\beta$ after that. In this case, the elevator boarding determination unit generates the behavior information indicating that the user is rising in the elevator. In the case where the elevator rising determination data is smaller than the predetermined value $D_\beta$ at first and, after that, larger the predetermined value $D_\alpha$, the elevator boarding determination unit generates the behavior information indicating that the user is descending in the elevator. In addition, the $D_\alpha$ is the minimum elevator rising recognition value that is a lower limit value for recognizing that the user starts to rise in the elevator. The $D_\beta$ is the maximum elevator descending recognition value that is an upper limit value for recognizing that the user starts to descend in the elevator. In this manner, since the elevator boarding determination unit allows the sensor data processing unit to perform a unique process specified to the behavior, it may be recognized with a good accuracy whether or not the user boards the elevator.

In addition, the functions of the information processing apparatus according to the embodiment may be expressed as follows. First, the lower area remover removes a frequency area, in which the user may be falsely recognized as boarding the electric train, from the first acceleration sensor data, the second acceleration sensor data, and the third acceleration sensor data. In this manner, the noise of the behavior information generated later is reduced by the process of the lower area remover, so that the behavior may be recognized with a better accuracy. Next, the sensor data calculation unit calculates horizontal direction acceleration sensor data and vertical direction acceleration sensor data based on the first acceleration sensor data, the second acceleration sensor data, and the third acceleration sensor data, from the frequency area is removed. Next, the sensor data calculation unit records the horizontal direction acceleration sensor data and the vertical direction acceleration sensor data in the sensor data storage unit. Next, the sensor data calculation unit calculates the horizontal direction variance value based on the horizontal direction acceleration sensor data recorded in the sensor data storage unit.

Next, the sensor data calculation unit calculates the vertical direction variance value based on the vertical direction acceleration sensor data recorded in the sensor data storage unit. The sensor data calculation unit integrates the small variance value among the horizontal direction variance value and the corrected vertical direction variance value. As a result, the sensor data calculation unit calculates the electric train boarding determination data for determining whether or not to board the electric train. Next, the electric train boarding determination unit determines whether or not the electric train boarding determination data is larger than the minimum electric train boarding recognition value that is a lower limit value for recognizing that the user boards the electric train. In this case, the electric train boarding determination unit generates the behavior information indicating that the user boards the electric train. In addition, the sensor data calculation unit determines whether or not the vertical direction variance value is equal to or smaller than the minimum allowable vertical variance value that is the minimum allowable vertical direction variance value. In addition, the sensor data calculation unit determines whether or not the vertical direction variance value is equal to or larger than the maximum allowable vertical variance value that is the maximum allowable vertical direction variance value. In this case, the sensor data calculation unit calculates the electric train boarding determination data as zero. In this manner, since the electric train boarding determination unit allows the sensor data processing unit to perform a unique process specified to the behavior, it may be recognized with a good accuracy whether or not the user boards the electric train.

In addition, the functions of the information processing apparatus according to the embodiment may be expressed as follows. First, the lower area remover removes an area, in which the user may be falsely recognized as turning to the right or to the left, from the first acceleration sensor data, the second acceleration sensor data, and the third acceleration sensor data. In this manner, the noise of the behavior information generated later is reduced by the process of the lower area remover, so that the behavior may be recognized with a better accuracy. Next, the sensor data calculation unit calculates an angular velocity in the gravity direction based on the first to third acceleration sensor data, from which the above-described areas are removed, and the first to third gyro sensor data. Next, the specific area remover removes an area in a range excluding the curve recognition area, in which the user may be recognized as turning to the right or to the left, from the angular velocity and calculates the corrected angular velocity. In this manner, the noise of the behavior information generated later is reduced by the process of the specific area remover, so that the behavior may be recognized with a better accuracy. The turning-to-the-right/turning-to-the-left determination unit determines whether or not the corrected angular velocity is smaller than the maximum turning-to-the-right recognition value that is an upper limit value for recognizing that the user turns to the right. In this case, the turning-to-the-right/turning-to-the-left determination unit generates the behavior information indicating that the user turns to the right. In addition, in the case where the corrected angular velocity is larger than the minimum turning-to-the-left recognition value that is a lower limit value for recognizing that the user turns to the left, the turning-to-the-right/turning-to-the-left determination unit generates the behavior information indicating that the user turns to the left. In this manner, since the electric train boarding determination unit allows the sensor data processing unit to perform a unique process specified to the behavior, it may be recognized with a good accuracy whether the user turns to the right or to the left.

In addition, the functions of the information processing apparatus according to the embodiment may be expressed as follows. First, the sensor data calculation unit calculates a value of the identification function by using the characteristic vectors, which are generated based on the first to third acceleration sensor data, and the identification function set for each types of vehicles. Next, in the case where the calculated value of the identification function is larger than the vehicle boarding recognition value that is used to recognize that the user boards the vehicle corresponding to the identification function, the vehicle boarding determination unit generates the behavior information indicating that the user boards the vehicle corresponding to the identification function. In this manner, in the information processing apparatus, since the simply and easily designed identification functions are set according to the vehicles, there is no problem that the apparatus has to have a large size, and the types of the vehicles to be determined may be increased. In addition, since the vehicle boarding determination unit determines based on the identification function specified to each vehicle whether or not each vehicle is boarded, although the change in the acceleration of the vehicle that the user boards is not large, it may be determined with a better accuracy whether or not each vehicle is boarded. In addition, since the behavior information post-processing unit of the behavior comparison re-processing unit or the like performs the post-process, there is no problem that the result of the behavior recognition of exchanging a plurality of the vehicles any number of times for a short time of about tens of seconds is generated, and the result of the behavior recognition may be obtained with a better accuracy.

It should be understood by those skilled in the art that various modifications, combinations, sub-combinations and alterations may occur depending on design requirements and other factors insofar as they are within the scope of the appended claims or the equivalents thereof.

What is claimed is:

1. An information processing apparatus comprising:
a processor configured to
execute a recognition of a behavior of a user based on a processing of sensor data, wherein the processing of sensor data includes determining horizontal acceleration of the user and vertical acceleration of the user, determining a horizontal direction variance value of the horizontal acceleration of the user over a predetermined period of time and a vertical direction variance value of the vertical acceleration of the user over the predetermined period of time, comparing the horizontal direction variance value and the vertical direction variance value to determine a smaller variance value, and comparing an integration value representing integration over the predetermined period of time of the smaller variance value resulting from the comparison between the horizontal direction variance value and the vertical direction variance value with a minimum determination threshold for the behavior; and
obtain, based on the recognized behavior, a behavior information of a vehicle boarding state indicating whether or not the user has boarded a vehicle, wherein the behavior information indicates that the user has boarded the vehicle when the integration value is greater than the minimum determination threshold; and
a storage unit configured to store the obtained behavior information.

2. The information processing apparatus according to claim 1, wherein the processing of sensor data further includes comparing the horizontal direction variance value and the vertical direction variance value to determine which is smaller, integrating the smaller of the horizontal direction variance value and the vertical direction variance value over a period of time, and determining whether the integrated variance value is above a minimum vehicle boarding recognition value, and further wherein the obtained behavior information indicates that the user has boarded the vehicle when the integrated variance value is above the minimum vehicle boarding recognition value.

3. The information processing apparatus according to claim 2, wherein the vehicle is determined to be a car, a bus, a train, or a bicycle based on a unique combination of thresholds and minimum boarding recognition values associated with each type of vehicle.

4. The information processing apparatus according to claim 1, wherein when the obtained behavior information indicates that the user has boarded the vehicle, the processor further determines whether the user is in a stop state, a walking state, a running state, a standing state, or a sitting state in the vehicle.

5. The information processing apparatus according to claim 1, wherein information corresponding to the obtained behavior information is provided to the user.

6. The information processing apparatus according to claim 1, wherein information corresponding to the obtained behavior information is shared to another user.

7. The information processing apparatus according to claim 1, wherein the processor is further configured to correlate the behavior information to at least one corresponding time point.

8. The information processing apparatus according to claim 1, wherein the processing of sensor data includes comparing the vertical direction variance value with a low vertical variance value threshold and a high vertical variance value threshold, and the obtained behavior information indicates that the user has not boarded the vehicle when the vertical direction variance value is below the low vertical variance value threshold or above the high vertical variance value threshold for the vehicle.

9. The information processing apparatus according to claim 1, wherein the determining of the horizontal acceleration of the user and the vertical acceleration of the user is performed on a predetermined amount of sensor data corresponding to the predetermined period of time, and the predetermined amount of sensor data is processed in a first in first out (FIFO) manner.

10. An information processing method comprising:
recognizing a behavior of a user based on a processing of sensor data, wherein the processing of sensor data includes determining horizontal acceleration of the user and vertical acceleration of the user, determining a horizontal direction variance value of the horizontal acceleration of the user over a predetermined period of time and a vertical direction variance value of the vertical acceleration of the user over the predetermined period of time, and comparing an integration value representing integration over the predetermined period of time of the smaller variance value resulting from the comparison between the horizontal direction variance value and the vertical direction variance value with a minimum determination threshold for the behavior;
obtaining, based on the recognized behavior, a behavior information of a vehicle boarding state indicating whether or not the user has boarded a vehicle, wherein the behavior information indicates that the user has boarded the vehicle when the integration value is greater than the minimum determination threshold; and
storing the obtained behavior information in a memory, wherein the recognizing of the behavior of the user, the obtaining of the behavior information of the vehicle boarding state, and the storing of the obtained behavior information are performed by at least one processor.

11. A non-transitory computer-readable medium having embodied thereon a program, which when executed by a computer causes the computer to perform an information processing method, the method comprising:
recognizing a behavior of a user based on a processing of sensor data, wherein the processing of sensor data includes determining horizontal acceleration of the user and vertical acceleration of the user, determining a horizontal direction variance value of the horizontal acceleration of the user over a predetermined period of time and a vertical direction variance value of the vertical acceleration of the user over the predetermined period of time, comparing the horizontal direction variance value and the vertical direction variance value to determine a smaller variance value, and comparing an integration value representing integration over the predetermined period of time of the smaller variance value resulting from the comparison between the horizontal direction variance value and the vertical direction variance value with a minimum determination threshold for the behavior;

obtaining, based on the recognized behavior, a behavior information of a vehicle boarding state indicating whether or not the user has boarded a vehicle, wherein the behavior information indicates that the user has boarded the vehicle when the integration value is greater than the minimum determination threshold; and storing the obtained behavior information in a memory.

* * * * *